United States Patent [19]
Kawagoe et al.

[11] Patent Number: 5,305,233
[45] Date of Patent: * Apr. 19, 1994

[54] SPECTROPHOTOMETER FOR ACCURATELY MEASURING LIGHT INTENSITY IN A SPECIFIC WAVELENGTH REGION

[75] Inventors: Nobukazu Kawagoe, Toyonaka; Masahito Inaba, Ikeda; Masami Sugiyama, Toyonaka, all of Japan

[73] Assignee: Minolta Camera Kabushiki Kaisha, Osaka, Japan

[*] Notice: The portion of the term of this patent subsequent to Dec. 29, 2009 has been disclaimed.

[21] Appl. No.: 951,732

[22] Filed: Sep. 25, 1992

Related U.S. Application Data

[63] Continuation of Ser. No. 697,928, May 2, 1991, Pat. No. 5,175,697, which is a continuation of Ser. No. 395,201, Aug. 15, 1989, abandoned, which is a continuation of Ser. No. 57,517, Jun. 1, 1987, abandoned.

[30] Foreign Application Priority Data

Jun. 2, 1986 [JP] Japan .................. 61-129013
Jun. 2, 1986 [JP] Japan .................. 61-129014
Jun. 2, 1986 [JP] Japan .................. 61-129015
Jun. 9, 1986 [JP] Japan .................. 61-133442

[51] Int. Cl.⁵ .............................. G01J 3/28
[52] U.S. Cl. ................... 364/526; 356/319; 356/328
[58] Field of Search ......... 364/524, 526, 581; 356/303, 319, 320, 326, 327, 328, 432, 433, 435

[56] References Cited

U.S. PATENT DOCUMENTS 3,804,531  4/1974  Kosaka et al. ............... 356/176
4,322,807  3/1982  Chamran et al. ............. 364/524
4,560,275  12/1985 Goetz ........................... 356/328
4,568,186  2/1986  Yoshimura et al. .......... 356/319
4,669,880  6/1992  Nelson et al. ................ 356/319
4,685,071  8/1987  Lee ............................... 364/526
4,703,437  10/1987 Nishimura .................... 356/319

FOREIGN PATENT DOCUMENTS 0081702  11/1982  European Pat. Off. .
56-79922   6/1981  Japan .
57-166532 10/1982  Japan .
59-20804   2/1984  Japan .
59-67429   4/1984  Japan .
59-206765 11/1984  Japan .
60-79248   5/1985  Japan .
60-113124  6/1985  Japan .
60-135730  7/1985  Japan .
2119086    4/1982  United Kingdom .

OTHER PUBLICATIONS

Color: Theory and Imaging Systems, Dr. Gunther Wyszechi, 1973 Society of Photographic Scientists and Engineers, Wash. D.C. pp. 24–29.
Chroma Meter CR-100/CR-110, Operational Manual, Minolta 1984, Japan.
Waveform Data Processing for the Scientific Measurement, Shigeo Minami, Chapter 7, issued Apr. 30, 1986; pp. 122–131.

Primary Examiner—Thomas G. Black
Assistant Examiner—Michael Zanelli
Attorney, Agent, or Firm—Price, Gess & Ubell

[57] ABSTRACT

A spectrophotometer utilizes a band-pass filter array for splitting incident light into a plurality of light components of different wavelengths, a plurality of silicon photodiodes for receiving the respective light components, and a memory for storing spectral sensitivity information. The spectral sensitivity information is obtained by integrating the spectral sensitivities of spectrodetectors relative to each sectionalized wavelength regions sectionally generated from a measurement wavelength region. Each of the spectrodetectors include a band-pass filter array and a silicon photodiode in combination. A central processing unit calculates simultaneous equations representing the relation between the output from each of the silicon photodiodes, the spectral sensitivity information stored in memory and the light intensity of the sectionalized wavelength region, to obtain the light intensity.

2 Claims, 54 Drawing Sheets

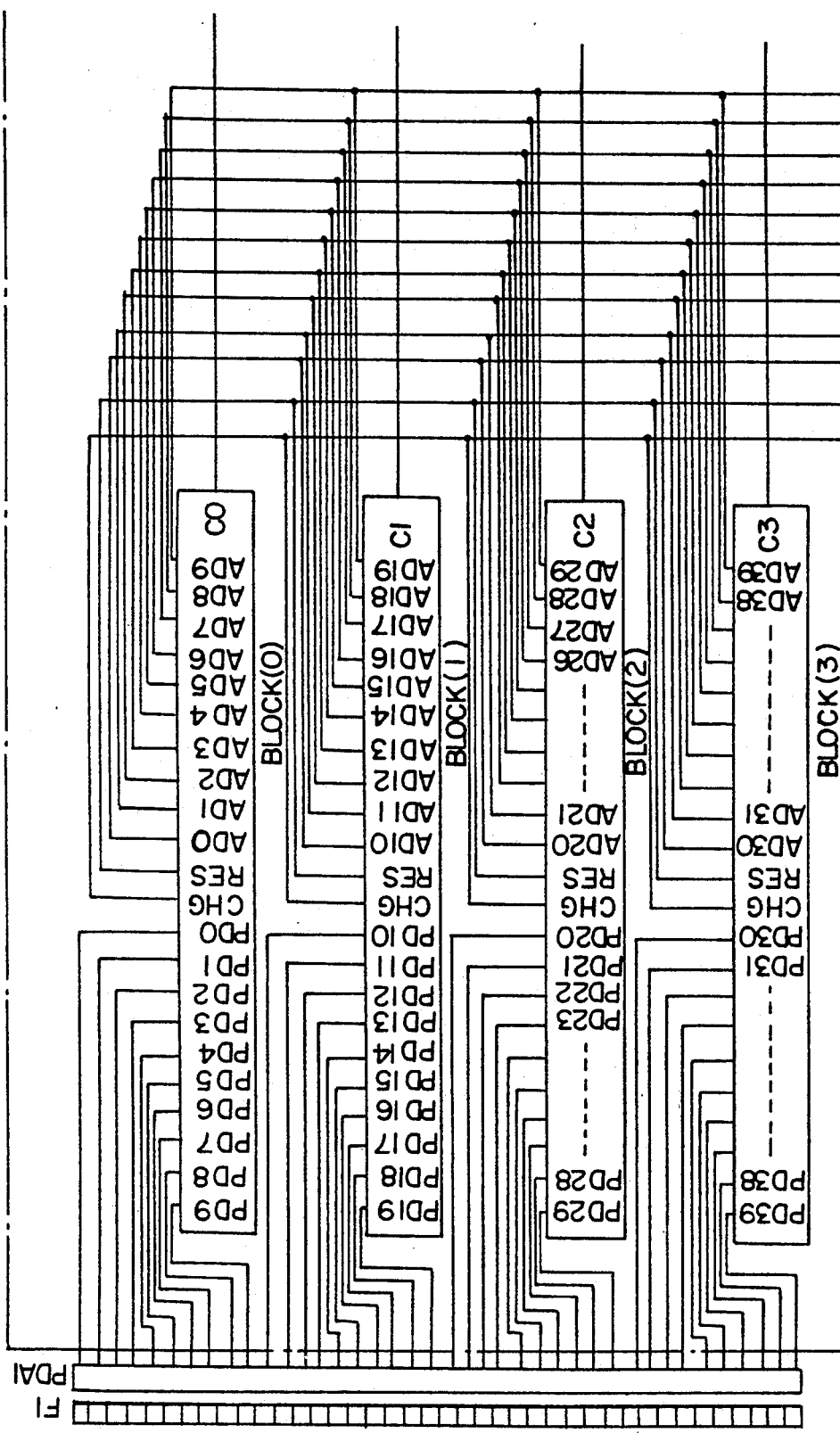
Fig. 4 (a1)

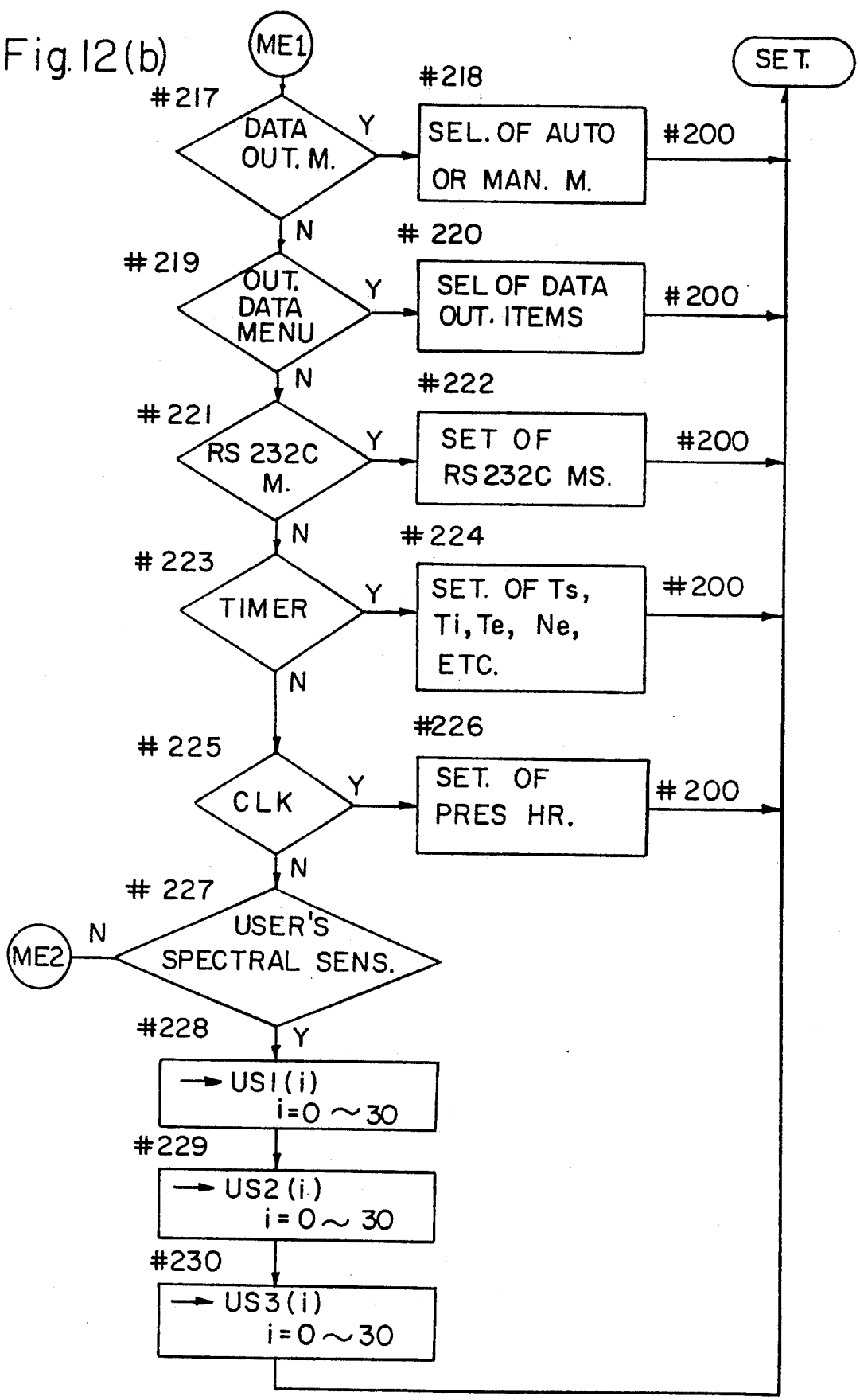

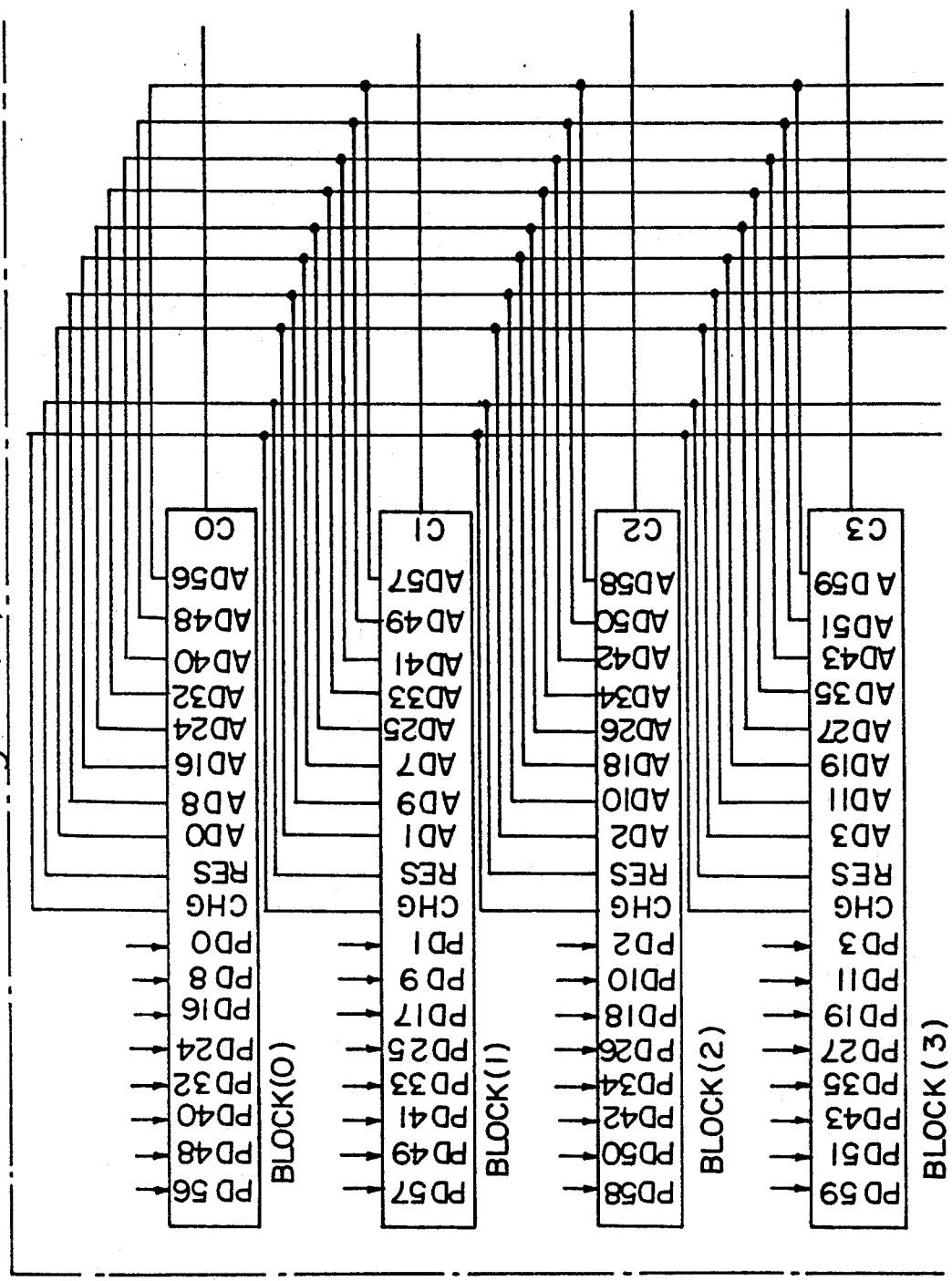
Fig. 31(a)
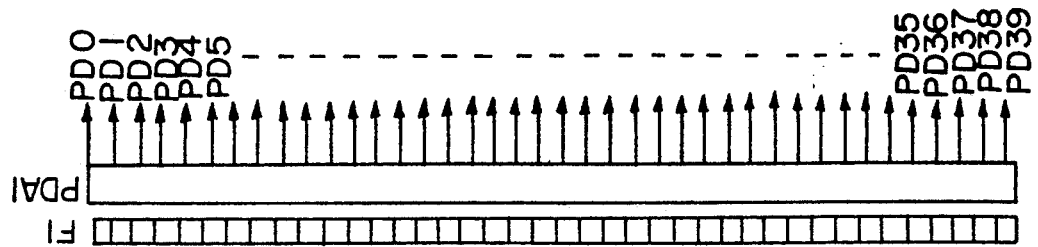

DARK OFFSET CORRECTION

SPECTRAL SENSITIVITY CORRECTION

SPECTROPHOTOMETER FOR ACCURATELY MEASURING LIGHT INTENSITY IN A SPECIFIC WAVELENGTH REGION

This is a continuation of application Ser. No. 07/697,928 filed on May 2, 1991 and issued as U.S. Pat. No. 5,175,697 on Dec. 29, 1992 for A spectrophotometer for accurately measuring light intensity in a specific wavelength region which is a continuation of application Ser. No. 07/395,201 filed on Aug. 15, 1989, now abandoned, which was a continuation of application Ser. No. 07/057,517, filed on Jun. 1, 1987, now abandoned.

BACKGROUND OF THE INVENTION

The present invention relates to an improved spectrophotometer.

A conventional a spectrophotometer is adapted to split incident light into a plurality of light components of different wavelengths and measure the light intensity of each wavelength. These spectrophotometers calculate the sum of the products of the isochromatic function ($\bar{x}\lambda$, $\bar{y}\lambda$, $\bar{z}\lambda$) of CIE standard colorimetric system with the respective measured spectral values to convert the measured spectral values into trisimulus values.

However, in the case of measuring color density of a colored picture, for example, other spectral sensitivities than the isochromatic function are used. Moreover, there may be individuals who want to use their own spectral sensitivities in evaluating color. In such a case, it would be of great benefit if operators can set their own spectral sensitivities (referred to as user's spectral sensitivities) for color evaluation.

Conventionally, elements consisting of a band-pass interference filter array in combination with a photodiode array have been used as spectrodetectors for measuring the light intensity of wavelengths separated at equal intervals. The respective band-pass interference filters are subject to deviation of a few nm due to the manufacturing process used to make them. So, it is impossible to make the intervals of wavelengths exactly equal. Moreover, the values of wavelengths having peak spectral sensitivity often deviate in some degree due to errors caused by the positional relation between the filter array and the photodiode array.

As described above, wavelengths at which outputs from spectrodetectors peak do not have completely equal intervals to each other due to the errors caused during the manufacturing process. However, measured spectral values for wavelengths at equal intervals are often required. A small pitch of the order of 10 nm is often required as a pitch between each adjacent wavelength for the respective peak output. As a result, the output from such a conventional spectrodetector can not be used without regulation.

In depositing an optical film using a vacuum deposition device, the spectral reflectance of the optical film is measured in real time. In order to carry out the measurement, a film thickness monitoring device of the following type is proposed as shown in Japanese Patent Laid-open Publicatin No. 59-20804. In the monitoring device, light emitted from an illumination light source irradiates a test piece. Its reflected light is detected by a spectrodetector while the intensity of the emitted light of the light source is measured by one light receiving element. This prior art device has only one light receiving element for measuring light from the light source; and measures only luminosity of the light source. Variations in spectral energy distribution of the light source for illumination can not be measured by this device.

Use of a pulse xenon lamp for the light source may be preferable, because less electric power is required. The pulse xenon lamp, however, has a spectral energy distribution that is variable in each flash and therefore, the measured spectral value is subject to errors.

A spectrophotometer of the following type is known. Incident light is split into its components according to their wavelength by an interference filter, a spectral prism or a diffraction grating. A light receiving element is disposed a position corresponding to, each wavelength. The output from the light receiving elements provide the measurement result.

The conventional spectrophotometer, however, has disadvantages. The splitting means used, such as a spectral prism, diffraction grating or the like, do not always lead a light component to a light receiving element corresponding to the wavelength of the light component. Therefore, there is a possibility that a light receiving element will also receive light components of other wavelengths. For example, assume a light receiving element is disposed to measure a light component of 500 nm in wavelength. The splitting means conducts a light component of 500 nm, and may also leak light components of other wavelengths to the same light receiving element. The importance of this disadvantage increases or decreases with the degree of resolvability of the splitting means, possibility of the occurrence of stray light in the optical system, the half-width of the light receiving element, etc.

As can be understood from the above, it is impossible to obtain a correct spectral measurement with a conventional spectrophotometer because the output of each of the light receiving elements includes errors, so the output of each light receiving element is not identical with the measured light component of corresponding wavelength.

OBJECTS AND SUMMARY OF THE INVENTION

Accordingly, an object of the present invention is therefore to substantially eliminating the above described disadvantage inherent in the prior art. Another object is to provide a spectrophotometer which can evaluate color with a spectral sensitivity set by an operator.

In order to accomplish these objects the spectrophotometer utilizes a splitting means for splitting incident light into a plurality of light components of different wavelengths, a plurality of light receiving means for receiving the respective light components and outputting measured spectral values R(i), a coefficient setting means for setting a set of arbitrary coefficients US1(11), US1(2), . . . , US1(i), . . . one for each wavelength, a memory for memorizing the coefficients, and a calculating means for calculating the sum $\Sigma US1(i) \cdot R(i)$ of products, for the respective wavelengths, of the measured spectral values R(i) times the coefficients US1(i) of the set.

Operators can set at least one set of weighting coefficients US1(i) one for each wavelength by the coefficient setting means as they desire, so that spectral sensitivities for their own use can be defined using the set of coefficients. The calculating means calculates the sum $\Sigma US1(i) \cdot R(i)$ of products, for the respective wavelengths, of the measured spectral values R(i) times the coefficients US1(i) of the at least one set. The sum obtained by the calculating means is a value of the measured spectral value R(i) evaluated by the user's spectral sensitivity. This spectrophotometer can be used for color evaluation of non-luminous object color and light source color.

Another spectrophotometer according to the invention, which is adapted to measure either a spectral reflectance or spectral transmissivity of a test piece by irradiating it with a light source, uses a coefficient setting means for setting a set of arbitrary coefficients US1(1), US1(2), ..., US1(i), ... one for each wavelength and a calculating means for calculating the sum $\Sigma P(i).US1(1).R(i)$ of products, for the respective wavelengths, of the measured spectral values R(i) times spectral energy distributions P(i) of the light source used for color evaluation times the coefficients US1(i) of the set.

This spectrophotometer is used for measuring the color of a test piece under the illumination of an arbitrary light source. Therefore, the product of R(i) and US(i) for each wavelength is multiplied by the spectral energy distribution P(i), for each wavelength, of the light source used for color evaluation in calculating the sum of products by the sum calculating means. Accordingly, the sum obtained by the calculating means is a value of reflection color or transmission color of the test piece evaluated by the user's spectral sensitivity, taking the spectral distribution of the light source used for color evaluation into consideration.

Another spectrophotometer according to the present invention can be constructed, if necessary, so that the coefficient setting means may be adapted to set further sets of coefficients US2(i), US3(i) and the sum relative to those sets of coefficients can be also calculated by the calculating means.

Another object of the present invention is to provide a spectrophotometer which can calculate a measured spectral value for a predetermined wavelength by the interpolation method even though there is scattering in the intervals of the wavelengths corresponding to the respective spectral sensitivity peaks of spectro-detectors (such wavelengths will be referred to as "peak wavelengths" hereafter).

In order to accomplish this object, the spectrophotometer includes a plurality of spectrodetectors. Each of the spectrodetectors includes an optical band-pass filter in combination with a light receiving element for splitting incident light into a plurality of light components of different wavelengths and outputting spectral values. It uses a first memory for memorizing a value corresponding to the wavelength for the spectral sensitivity peak of each spectrodetector, a second memory for memorizing the spectral value measured by each spectrodetector and an interpolating means for calculating a measured spectral value for a predetermined wavelength by an interpolation method from the contents stored in the first memory and in the second memory.

The spectrophotometer according and the present invention with the above construction functions as follows. A plurality of optical band-pass filters transmit light to split it into light components of different wavelengths. The light components are received by a plurality of light receiving elements. Spectral sensitivities of spectrodetectors, each of which consists of the band-pass filter in combination with the light receiving element, do not necessarily have their respective peak wavelengths which are spaced equally. Such peak wavelengths are memorized in the first memory. The values measured by the light receiving elements are stored in the second memory. The interpolating means calculates a measured value for a predetermined wavelength by the interpolation method, using the contents stored in the first and second memories. Accordingly, the measured value for the predetermined wavelength can be obtained even though there is scatter in the peak wavelengths of the spectrodetectors.

A further object of the present invention is to provide a spectrophotometer in which errors caused by the variation of the spectral energy distribution of the light source can be removed from the measured spectral values of the test piece so that correct measured spectral values may be obtained.

In order to accomplish this object, the spectrophotometer uses a light source for irradiating a test piece; a first splitting means for splitting light coming from the test piece into a plurality of light components of different wavelengths; a first light receiving element array for receiving the respective light components obtained by the splitting with the first splitting means; a second splitting means for splitting light emitted from the light source into a plurality of light components of different wavelengths; a second light receiving element array for receiving the respective light components obtained by the splitting with the second splitting means; analog-to-digital converters (A/D converters) for analog-to-digital conversion of the outputs from both the first and second light receiving element arrays; and a calculating means for calculating the ratio of the analog-to-digital converted value of the output from the first light receiving element array to that from the second light receiving element array.

The spectrophotometer with the above construction functions as follows. The test piece to be measured is illuminated by the light source. Light coming from the test piece is split by the first splitting means into a plurality of light components. These light components are received by the first light receiving element array. Measured spectral values obtained as output from the first light receiving element array have been affected by the variation of the spectral energy distribution of the light souce, which causes measurement errors. In the present invention, the spectral energy distribution of the light source is measured simultaneously with each measurement of the test piece. For the measurement of the light source, light emitted therefrom is split into a plurality of light components of different wavelengths by the second splitting means. The light components obtained in this way are received by the second light receiving element array. Measured spectral values obtained as output from the second light receiving element array are considered as the spectral energy distribution of the light source. The output from each of the first and second light receiving element arrays is A/D converted by the A/D converters. The ratio of both outputs is calculated by the calculating means. The ratio obtained is a measured spectral value, of the test piece, without any influence of the variation of the spectral energy distribution. Accordingly, measurment errors caused by the variation of the spectral energy distribution of the light source can be removed and correct measured spectral values can be obtained.

A still further object of the present invention is to provide a spectrophotometer which can improve the poor measurement accuracy due to the measurement errors described above.

In order to accomplish this object, the spectrophotometer uses a splitting means for splitting incident light into a plurality of light components of different wavelengths; a plurality of light receiving means for receiving the respective light components; a memory for memorizing spectral sensitivity information aij corresponding to values obtained by integrating spectral sensitivities Si(λ) of spectrodetectors relative to each of sectionalized wavelength regions sectionally generated from a measurement wavelength region, each of the spectrodetectors including the splitting means and one of the receiving means in combination; and a mathematical operation means for calculating simultaneous equations holding for the relation between output Oi from each of the light receiving means, the spectral sensitivity information aij stored in the memory and light intensity Pi of the sectionalized wavelength region so that the light intensity Pi can be obtained.

The spectrophotometer with the above construction functions as follows. Incident light is split into light components of different wavelengths by the splitting means and those light components are received by the plurality of light receiving means. The output Oi of each of the light receiving means does not necessarily represent a true light intensity Pi of wavelength corresponding to itself because there is a possibility that the output Oi may have been affected by light components of other wavelengths. For the purpose of deriving the true light intensity Pi from the output Oi affected by light components of neighboring wavelengths, spectral sensitivity information $a_{ij}$ is stored in the memory. The spectral sensitivity information $a_{ij}$ corresponds to a value obtained by intergrating spectral sensitivities Si(λ) of a spectrodetector including the splitting means and each of the receiving means, relative to each of sectionalized wavelength regions sectionally generated from a measurement wavelength region. The mathematical operation means calculates each light intensity Pi by solving simultaneous equations holding for the output Oi of each light receiving means, the spectral sensitivity information $a_{ij}$ stored in the memory and the light intensity Pi of the sectionalized wavelength region, whereby the true light intensity Pi is obtained with each wavelength without any influence of light components of other wavelengths.

BRIEF DESCRIPTION OF THE DRAWINGS

The present invention will be described with reference to the accompanying drawings, provided purely by way of non-limiting example, in which:

FIGS. 12(a) through 12(c) are flow charts of a setting subroutine in said embodiment;

DETAILED DESCRIPTION OF THE PREFERRED EMBODIMENT

Figure 1:
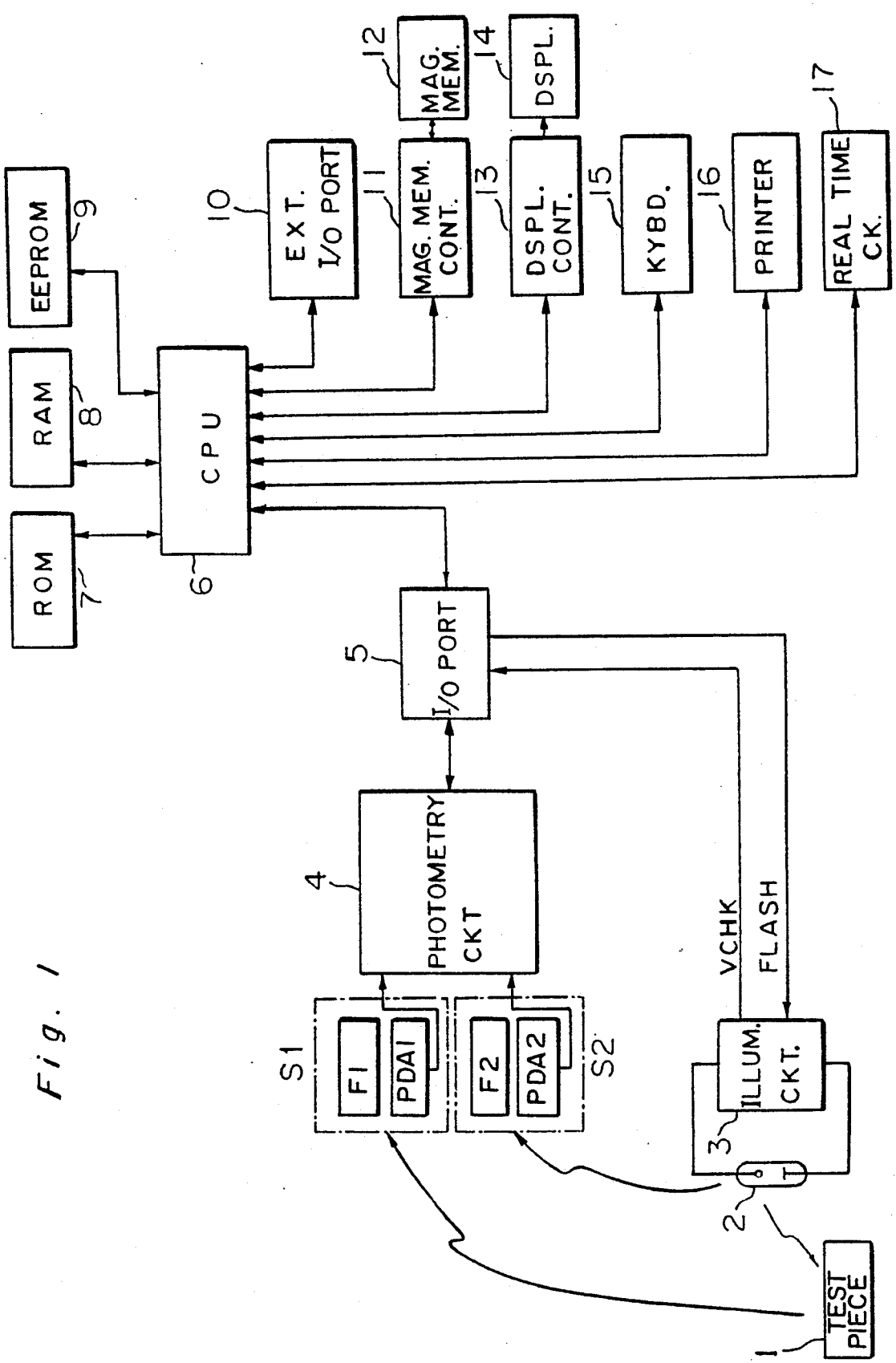
FIG. 1 is a block diagram showing the whole construction of a spectrophotometer according to an embodiment of the present invention.

In FIG. 1, which is a block diagram of an embodiment of the present invention, S1 and S2 designate spectral sensors which split incident light to light components of different wavelengths and output in parallel photoelectric currents in proportion to the intensities of light components of respective wavelengths. The sensors contain band-pass filter arrays F1 and F2 and silicon photodiode arrays PDA1 and PDA2, respectively. Each of the silicon photodiode arrays PDA1, PDA2 consists of 40 silicon photodiodes disposed in a line. The band-pass filter arrays F1, F2 are disposed in the light paths to the respective silicon photodiode arrays PDA1, PDA2. Each of the band-pass filter arrays F1, F2 consists of a large number of optical band-pass filters of different transmissible wavelengths which are arranged in a line so that the wavelengths of transmitted light components may be changed continuously from a shorter wavelength to a longer wavelength. The wavelength of light incident on the silicon photodiode arrays PDA1, PDA2 through the respective band-pass filter arrays F1, F2 is continuously changed from short to long.

Figure 27A:
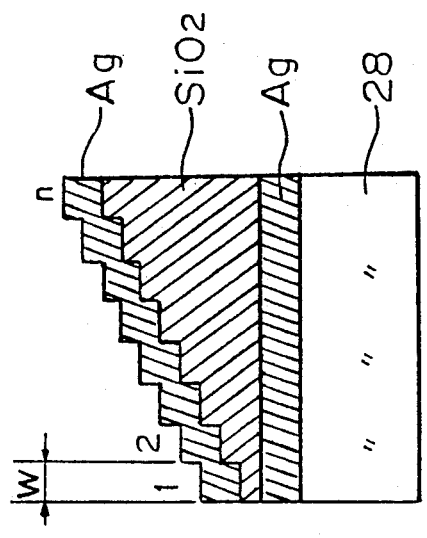
FIGS. 27(a) and (b) are a sectional view showing interference filters and a graph showing transmissivity of the interference filters, respectively.
Figure 27B:
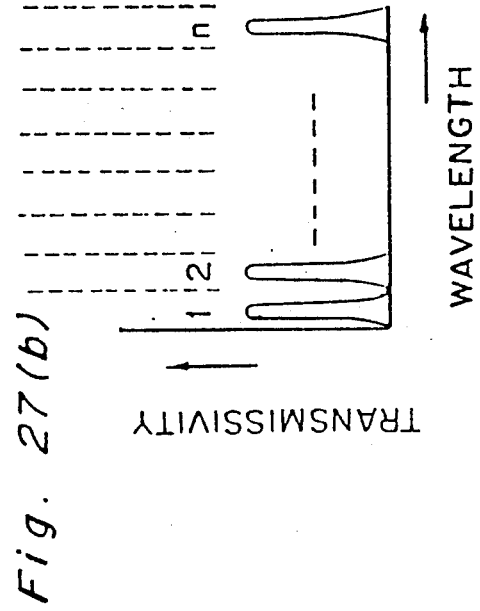
Figure 26:
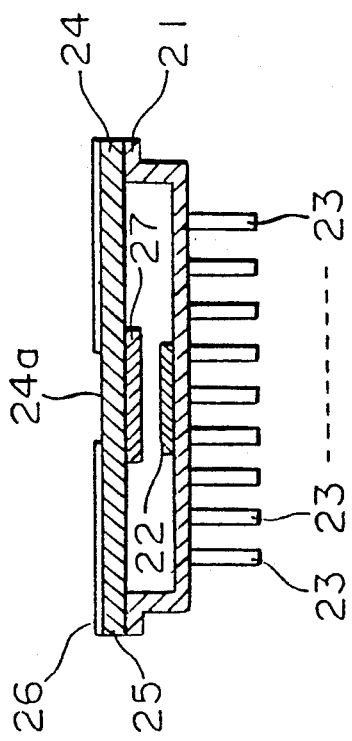
FIG. 26 is a sectional view showing the construction of the light receiving portion in said embodiment.
Figure 28:
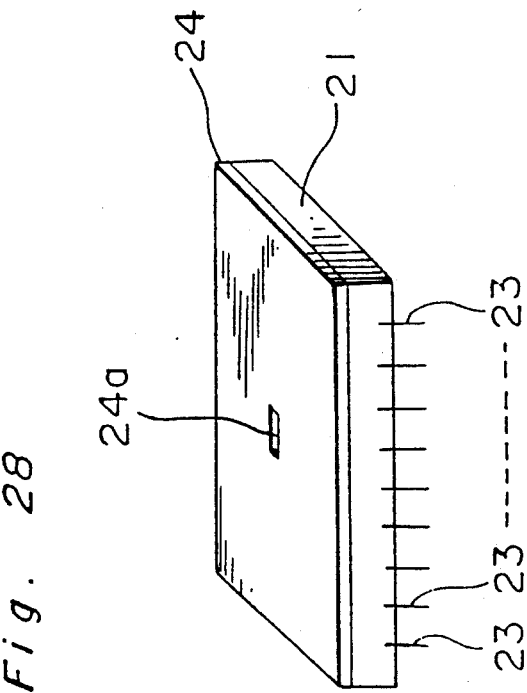
FIG. 28 is a perspective view of the light receiving portion in said embodiment.

The construction of the spectral sensors of this embodiment are shown in detail in FIGS. 26 through 28. In FIG. 26, reference numeral 21 designates an IC ceramic package. Reference numeral 22 designates an array sensor consisting of a number of very small silicon photodiodes stuck to the inner side of the IC ceramic package 21 The photodiodes are connected with a number of terminal pins 23 by a plurality of gold wires, respectively. A slit 24a is formed in a mask plate 24 for limiting the light bundle incident on the array sensor 22. The mask plate 24 having the slit 24a is manufactured by making a metal layer 26 on a glass plate 25 and forming the slit 24a in the metal layer in a known edging method. An interference filter 27 is attached to the rear surface of the glass plate 25 by a transparent bonding agent for transmitting the light having different wavelengths in its positions.

FIG. 27(a) shows an enlarged cross-sectional view of the interference filter 27. The interference filter 27 is manufactured by forming, on a glass plate 28, a silver layer Ag, a silicon dioxide layer $SiO_2$, and another silver layer Ag in turn, by a known vacuum deposition method. The thickness of the silicon dioxide layer $SiO_2$ is varied in steps. The number of steps correspond to the number of wavelengths to be detected. Accordingly, the portion of the interference filter 27 having the thinnest silicon dioxide layer permits transmission of the shorterst wavelength of light, as shown is FIG. 27(b). The wavelength of light passing through the interference filter 27 is lengthened by increasing the thickness of the silicon dioxide layer $SiO_2$. The thickness of the silver layers Ag and that of the silicon dioxide layer $SiO_2$ are determined in accordance with the wavelength of light to be detected. The width of each step of the interference filter 27 is determined in accordance with the width of each silicon photodiode of the array sensor 22.

Part of light emitted from a pulse xenon lamp 2 by an illumination circuit 3 is incided into the spectral sensor S2 for light source measurement so as to measure scattering in the spectral energy distribution. Another part of the light illuminates a test piece 1. Light reflected from the test piece 1 falls onto the spectral sensor S1 for sample measurement. Photoelectric current generated in proportion to energy of each wavelength of the incident light into the spectral sensors S1, S2 is outputted from each of the silicon photodiodes of the spectral sensors S1, S2. The outputted photoelectric currents from the silicon photodiode arrays PDA1, PDA2 are inputted into a photometry circuit portion 4, where each time each of the silicon photodiodes outputs the photoelectric current, the output is integrated and analog-to-digital converted. The A/D converted integration values are inputted into a control and operation portion 6 through I/O port 5. The illumination circuit 3 is controlled by the control and operation portion 6 through the I/O port 5. The construction and operation of the photometry circuit portion 4 and of the illumination circuit 3 will be described later in detail.

The control and operation portion 6 consists of CPU which carries out the control of the whole system and the operation. To the control and operation portion 6 are connected a program storage portion or read only memory (ROM) 7 which stores programs to be carried out by the control and operation portion 6; a data storage portion or random access memory (RAM) 8 which memorizes operation data, condition of the system, etc.; a spectral sensor data storage portion or electrically erasable and programmable read only memory (EEPROM) 9 which stores wavelengths detected by the spectral sensors S1, S2, various kinds of correction constants, etc. which can be erased electrically; an external I/O port 10 for inputting or outputting data into or from external devices such as an external personal computer, etc.; a magnetic memory control portion 11 for controlling magnetic memory devices 12 such as a floppy disk, a hard disk, or the like; a display control portion 13 for controlling a display portion 14 made of liquid crystal or CRT; a keyboard 15; a printer 16; and a real time clock for counting current hours, all of which are controlled by the control and operation portion 6.

Figure 2:
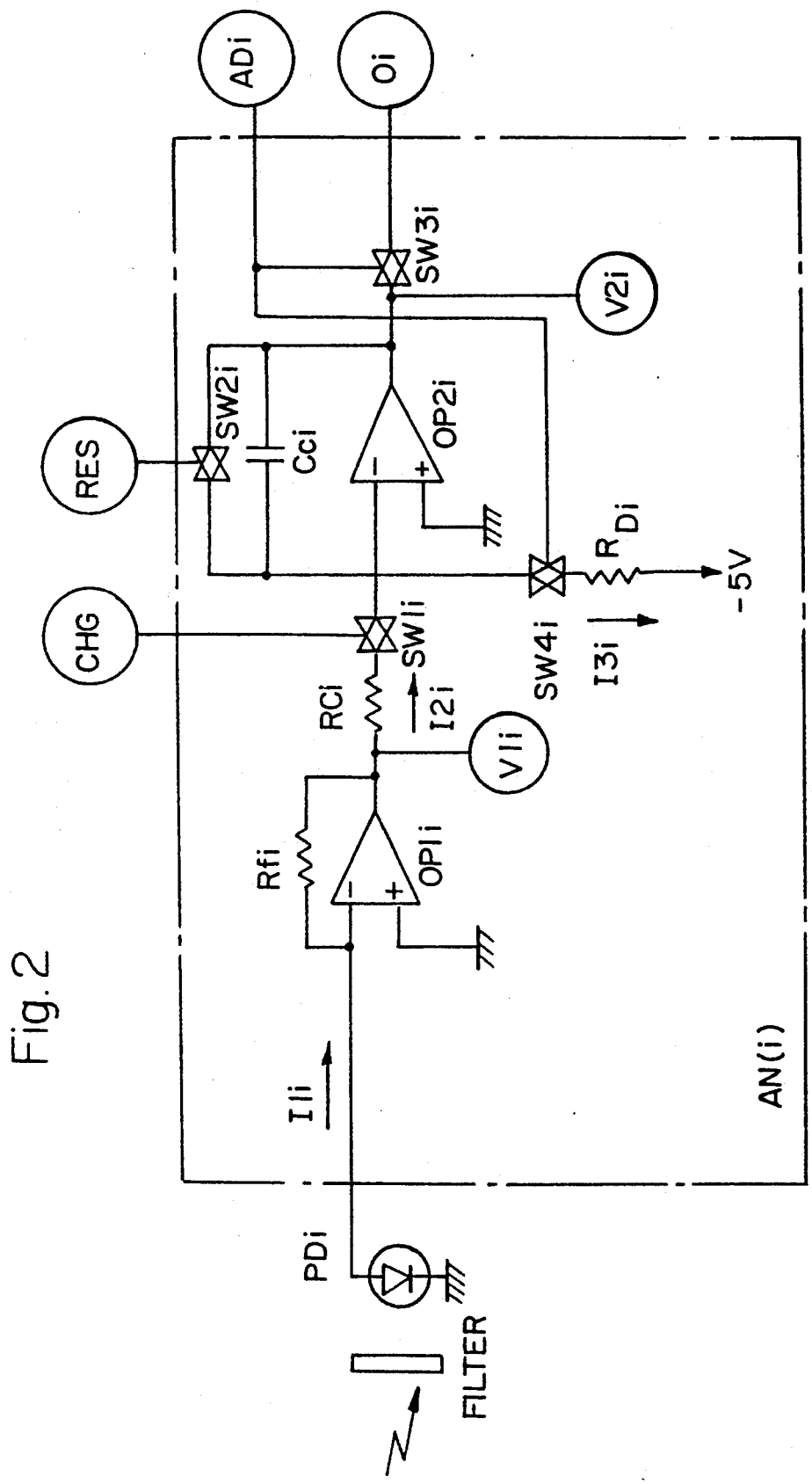
FIG. 2 is a circuit diagram of a current voltage conversion and integration circuit used in said embodiment.
Figure 3:
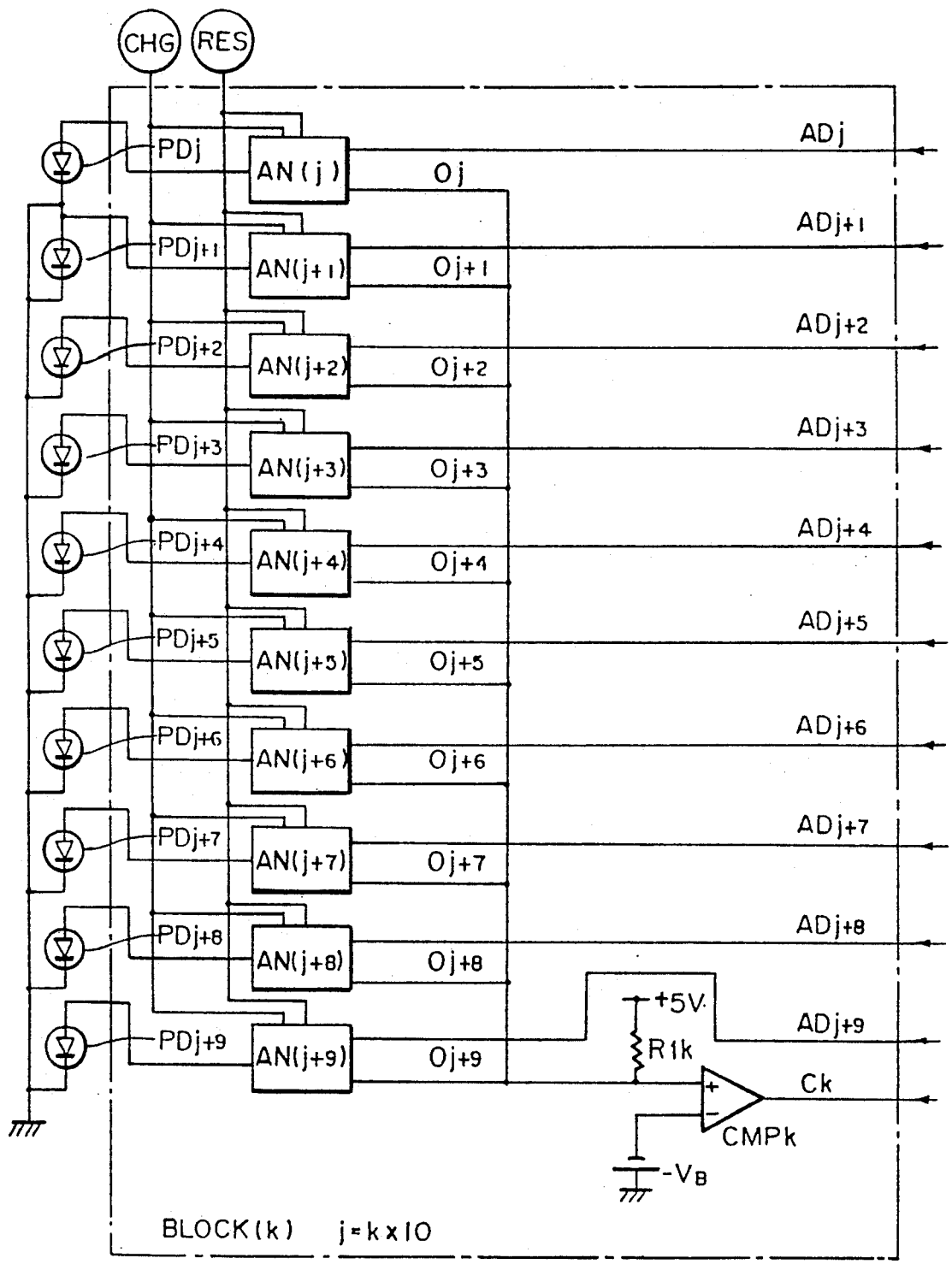
FIG. 3 is a circuit diagram showing a block of a photometry circuit used in said embodiment.
Figure 4:
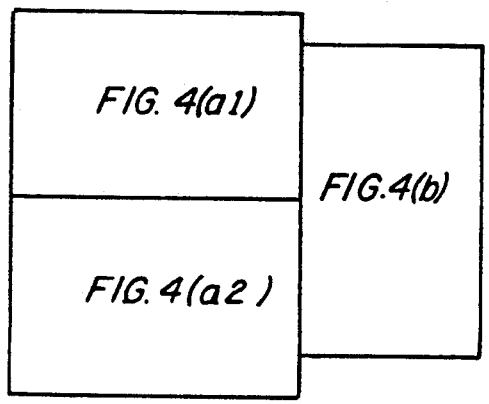
FIGS. 4(a1), 4(a2), and 4(b), taken together as shown in FIG. 4, are circuit diagrams of the photometry circuit used in said embodiment.
Figure 5:
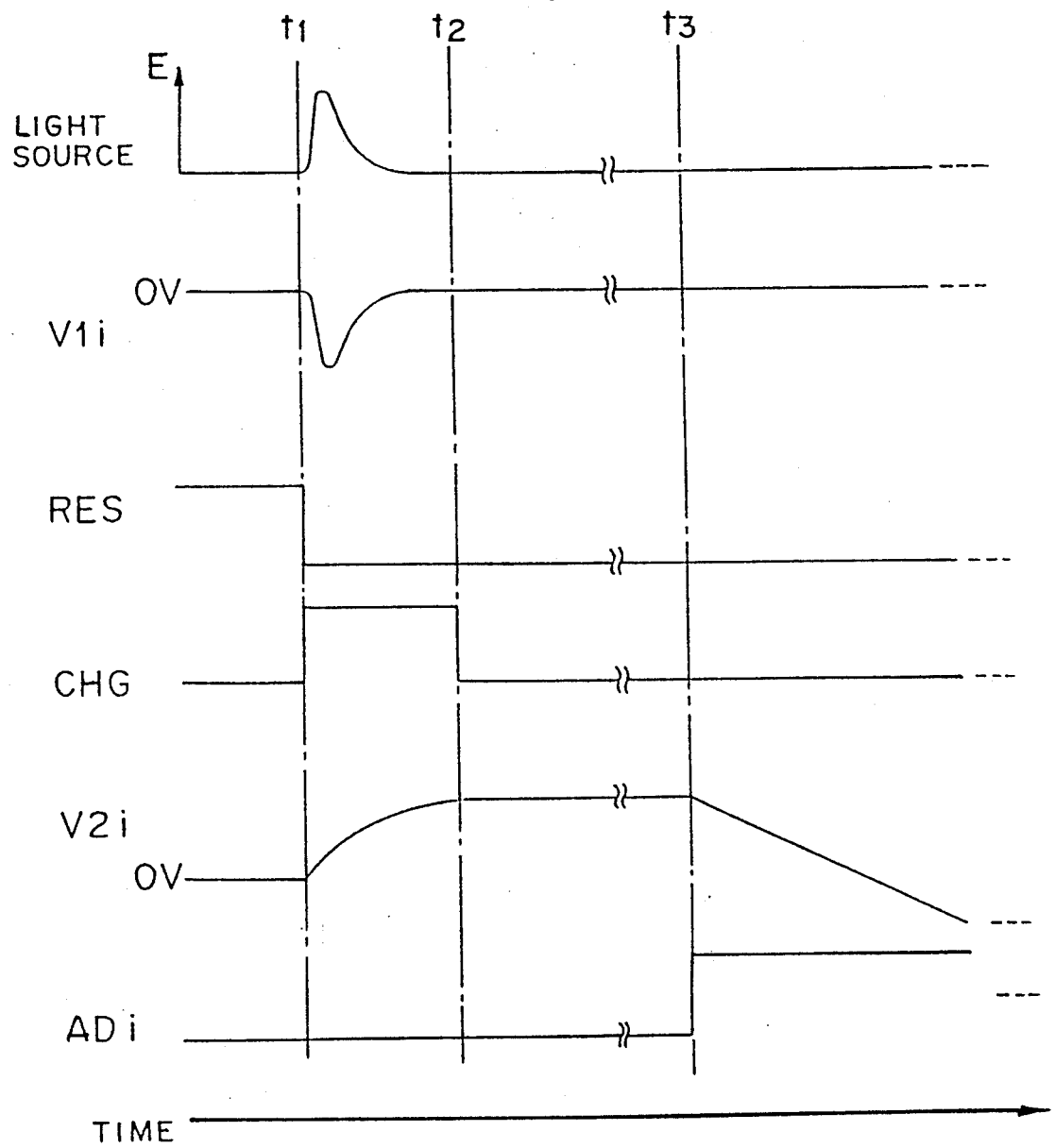
FIG. 5 is a timing chart for explaining the operation of the circuit of FIG. 2.
Figure 7:
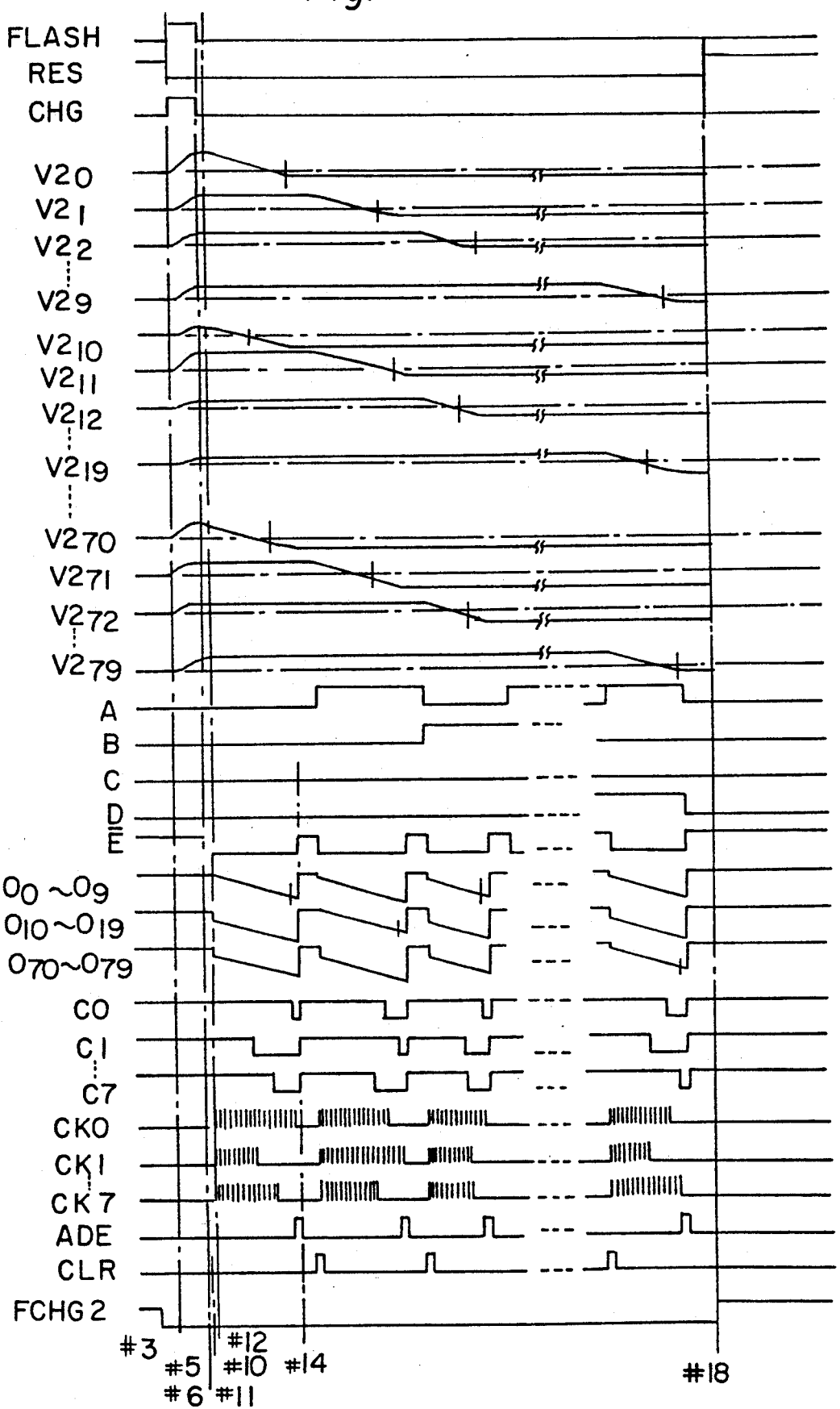
FIG. 7 is a timing chart showing photometry timing in said embodiment.

FIGS. 2, 3 and 4 are circuit diagrams of the photometry circuit 4, FIGS. 5 and 7 are timing charts of the photometry and FIG. 8 is a flow chart of the photometry control program.

FIG. 2 shows a current to voltage conversion circuit and an integration circuit which are connected to a silicon photodiode PDi selected arbitrarily from among the silicon photodiode arrays PDA1, PDA2. The circuit of FIG. 2 is connected to each of the silicon photodiodes of the silicon photodiode arrays PDA1, PDA2. In FIG. 2, OP1i designates an operational amplifier and between its inverting input terminal and output terminal is connected a feedback resistor Rfi. The noninverting input terminal of the operational amplifier OP1i is connected to the ground. The anode of the silicon photodiode PDi is connected to the inverting input terminal of the operational amplifier OP1i and the cathode thereof is connected to the ground. The output terminal of the operational amplifier OP1i is connected to an end of a resistor Rci for integration and the other end thereof is connected to the input terminal of an analog switch SW1i. The output terminal of the analog switch SW1i is connected to the inverting input terminal of an operational amplifier OP2i. A control terminal of the analog switch SW1i is connected to integration control signal CHG which will be described later. A capacitor Cci for integration and an analog switch SW2i for integration reset are connected in parallel between the inverting input terminal and the output terminal of the operational amplifier OP2i. Control terminal of the analog switch SW2i is connected to signal RES which will be described later. The inverting input terminal of the operational amplifier OP2i is connected to the input of an analog switch SW4i for electric discharge, output of which is connected to an end of a resistor $R_{Di}$ for electric discharge and the other end thereof is connected to −5 V. The control signal of the analog switch SW4i is named ADi for the description convenience. The noninverting input terminal of the operational amplifier OP2i is connected to the ground and the output terminal thereof is connected to the input terminal of an analog switch SW3i. The output terminal of the analog switch SW3i is named Oi for the description convenience. Control signal of the analog switch SW3i is connected to the control signal ADi of the analog switch SW4i. The whole circuits just mentioned are named AN(i) for the description convenience.

FIG. 5 is a timing chart for explaining the operation of the circuit of FIG. 2. Hereinafter, the operation of the circuit of FIG. 2 will be described by way of the timing chart of FIG. 5. At time t1, the signal RES is at low level and the signal CHG at high level, then the analog switch SW2i is in an OFF-state and the analog switch SW1i is in an ON-state. At the same time or a little later, the pulse xenon lamp 2 is caused to flash by the illumination circuit 3 and light incides into the silicon photodiode PDi through the band-pass filter array F1 or F2. When the light incides into the silicon photodiode PDi, photoelectric current I1i in proportion to the intensity of the incident light flows from the anode of the silicon photodiode PDi to the inverting input terminal of the operational amplifier OP1i and most of the photoelectric current flows into the feedback resistor Rfi. Output voltage V1i of the operational amplifier OP1i is expressed as follows:

$$V1i = -I1i \cdot Rfi \quad (1)$$

As the analog switch SW1i is in an ON-state and SW2i in an OFF-state, electric current I2i expressed by the following equation (2) flows from the output terminal of the operational amplifier OP1i toward the capacitor Cci for integration through the resistor Rci for integration.

$$I2i = \frac{V1i}{Rci} \quad (2)$$

Output voltage V2i from the operational amplifier OP2i for integration is obtained by integrating electric current I2i relative to time as follows:

$$V2i = -\frac{1}{Cci} \int_{t1}^{t} I2i\, dt \quad (3)$$

Accordingly, the output voltage V2i is in proportion to the integrated value of the intensity of the incident light into the silicon photodiode PDi relative to time. At time t2, after the pulse xenon lamp 2 has flashed, the signal CHG is set to low level and the analog switch SW1i is turned off. At this time, the output voltage V2i of the operational amplifier OP2i for integration is held. Thereafter, at time t3, the signal ADi gets to high level and the analog switches SW4i, SW3i are turned on. The electric charge in the capacitor Cci for integration is discharged to −5 V through the analog switch SW4i and the resister $R_Di$ for discharge in the form of fixed current I3i defined in the following equation:

$$I3i = -\frac{5}{R_Di} \quad (4)$$

Accordingly, the output voltage V2i of the operational amplifier OP2i for integration reduces linearly. Signal Oi and further operation after time t3 will be described later.

FIG. 3 is a circuit diagram showing a block (the kth block) in the photometry circuit 4. The eighty silicon photodiodes in all in the silicon photodiode arrays PDA1 and PDA2 together are divided by ten into eight blocks. In this embodiment, the silicon photodiodes are divided so that ten silicon photodiodes in each block may be continuous. As shown in FIG. 3, the anodes of the ten silicon photodiodes $PD_j \sim PD_{j+9}$ (j=k×10) in the kth block (k=0,1, ..., 7) are connected to the respective current-voltage conversion and integration circuits $AN(j) \sim AN(j+9)$. Their cathodes are connected to the ground. All outputs $O_j \sim O_{j+9}$ of analog switches $SW3_j \sim SW3_{j+9}$ in the circuits AN(j) through AN(j+9) are connected to the noninverting input terminal of a comparator CMPk, which terminal is connected to +5 V through the resistor R1k. The inverting input terminal of the comparator CMPk is connected to a negative reference voltage $-V_B$. Output from the comparator CMPk is assumed to be Ck. ADj through $AD_{j+9}$ designate control signals for the analog switches $SW4_j$ through $SW4_{j+9}$, $SW3_j$ through $SW3_{j+9}$ in the respective circuits AN(j) through AN(j+9). The circuit block of FIG. 3 is named BLOCK(k) (k=0,1,2, ..., 7) for description convenience.

FIG. 4 is a circuit diagram of the whole photometry circuit of this embodiment. F1 and F2 are the band-pass filter arrays and PDA1 and PDA2 are the silicon photodiode arrays. As described above, the silicon photodiodes in each of silicon photodiode arrays PDA1, PDA2 are divided by 10 into four blocks, or eight blocks in all. The silicon photodiodes in the eight blocks are all connected to the respective circuit blocks BLOCK(0) through BLOCK(7). The cathodes of all the silicon photodiodes are connected to the ground.

IC1 designates a decoder having four inputs and sixteen outputs. An input terminal $\overline{E}$ of the decorder IC1 is an enable terminal. When the input terminal $\overline{E}$ is at high level, all the outputs $Q_0$ through $Q_{15}$ are low. When the input terminal $\overline{E}$ is at low level, one of the outputs $Q_0$ through $Q_{15}$ becomes high and the others become low according to a four-bit signal inputted into the input terminals A, B, C, and D. Outputs $Q_{10}$ through $Q_{15}$ are not used in this embodiment, and so, they are omitted from the circuit diagram. The relation between the inputs A, B, C, D and $\overline{E}$ and the outputs $Q_0$ through $Q_9$ is shown in Table 1 at the end of this specification. As a unit which can carry out such function, CMOS-IC 4514 may be given, for example.

The output $Q_0$ of the decoder IC1 is connected with terminals $AD_0$, $AD_{10}$, $AD_{20}$, $AD_{30}$, $AD_{40}$, $AD_{50}$, $AD_{60}$, and $AD_{70}$ of the blocks BLOCK (0)~(7). The output $Q_1$ is connected with $AD_1$, $AD_{11}$, $AD_{21}$, $AD_{31}$, $AD_{41}$, $AD_{51}$, $AD_{61}$, and $AD_{71}$. The output Q2 is connected with terminals $AD_2$, $AD_{12}$, $AD_{22}$, $AD_{32}$, $AD_{42}$, $AD_{52}$, $AD_{62}$, and $AD_{72}$. The output $Q_3$ is connected with terminals $AD_3$, $AD_{13}$, $AD_{23}$, $AD_{33}$, $AD_{43}$, $AD_{53}$, $AD_{63}$, and $AD_{73}$. The output $Q_4$ is connected with terminals $AD_4$, $AD_{14}$, $AD_{24}$, $AD_{34}$, $AD_{44}$, $AD_{54}$, $AD_{64}$, and $AD_{74}$. The output $Q_5$ is connected with terminals $AD_5$, $AD_{15}$, $AD_{25}$, $AD_{35}$, $AD_{45}$, $AD_{55}$, $AD_{65}$, and $AD_{75}$. The output $Q_6$ is connected with terminals $AD_6$, $AD_{16}$, $AD_{26}$, $AD_{36}$, $AD_{46}$, $AD_{56}$, $AD_{66}$, and $AD_{76}$. The output $Q_7$ is connected with terminals $AD_7$, $AD_{17}$, $AD_{27}$, $AD_{37}$, $AD_{47}$, $AD_{57}$, $AD_{67}$, and $AD_{77}$. The output $Q_8$ is connected with terminals $AD_8$, $AD_{18}$, $AD_{28}$, $AD_{38}$, $AD_{48}$, $AD_{58}$, $AD_{68}$, and $AD_{78}$. The output $Q_9$ is connected with terminals $AD_9$, $AD_{19}$, $AD_{29}$, $AD_{39}$, $AD_{49}$, $AD_{59}$, $AD_{69}$, and $AD_{79}$.

Comparator outputs C0 through C7 in all the circuit blocks BLOCK(0) through BLOCK(7) are inputted into a circuit IC2 which is an eight-input NOR gate. The comparator outputs C0, C1, C2, C3, C4, C5, C6, C7 are also connected to respective terminals of two-input AND gates IC4, IC5, IC6, IC7, IC8, IC9, IC10, IC11, the other input terminals of all of which are connected to the output terminal of a two-input NOR gate IC3. IC12 through IC19 are 16-bit counters, whose values are cleared to zero at the positive edge of input CLR and increase by one at the positive edge of input CK. OSC designates an oscillator for outputting a reference clock signal for A/D conversion. The output of oscillator OSC is connected to one of the two inputs of the two-input NOR gate IC3. The I/O port 5 has been described referring to FIG. 1. The signals RES and CHG described referring to FIG. 2 are outputs of the I/O port 5. The inputs $\overline{E}$, A, B, C, D of the decoder IC1 are outputs of the I/O port 5. The output of the eight-input NOR gate IC2 is inputted into the input ADE of the I/O port 5. The output CLR of the I/O port 5 is connected to the input CLR of each of the counters IC12 through IC19. The output $\overline{E}$ of the I/O port 5 is connected to an input of the two-input NOR gate IC3. To the other input of the gate IC3 is inputted the output from the oscillator OSC, and accordingly, when the signal $\overline{E}$ is "Low", the two-input NOR gate IC3 outputs an inversion signal from the oscillator OSC, and when the signal $\overline{E}$ is "High", output of the gate IC3 is always "Low". The counters IC12 through IC19 send their respective outputs CT0, CT1, CT2, CT3, CT4, CT5, CT6, CT7 to the I/O port 5.

Figure 6:
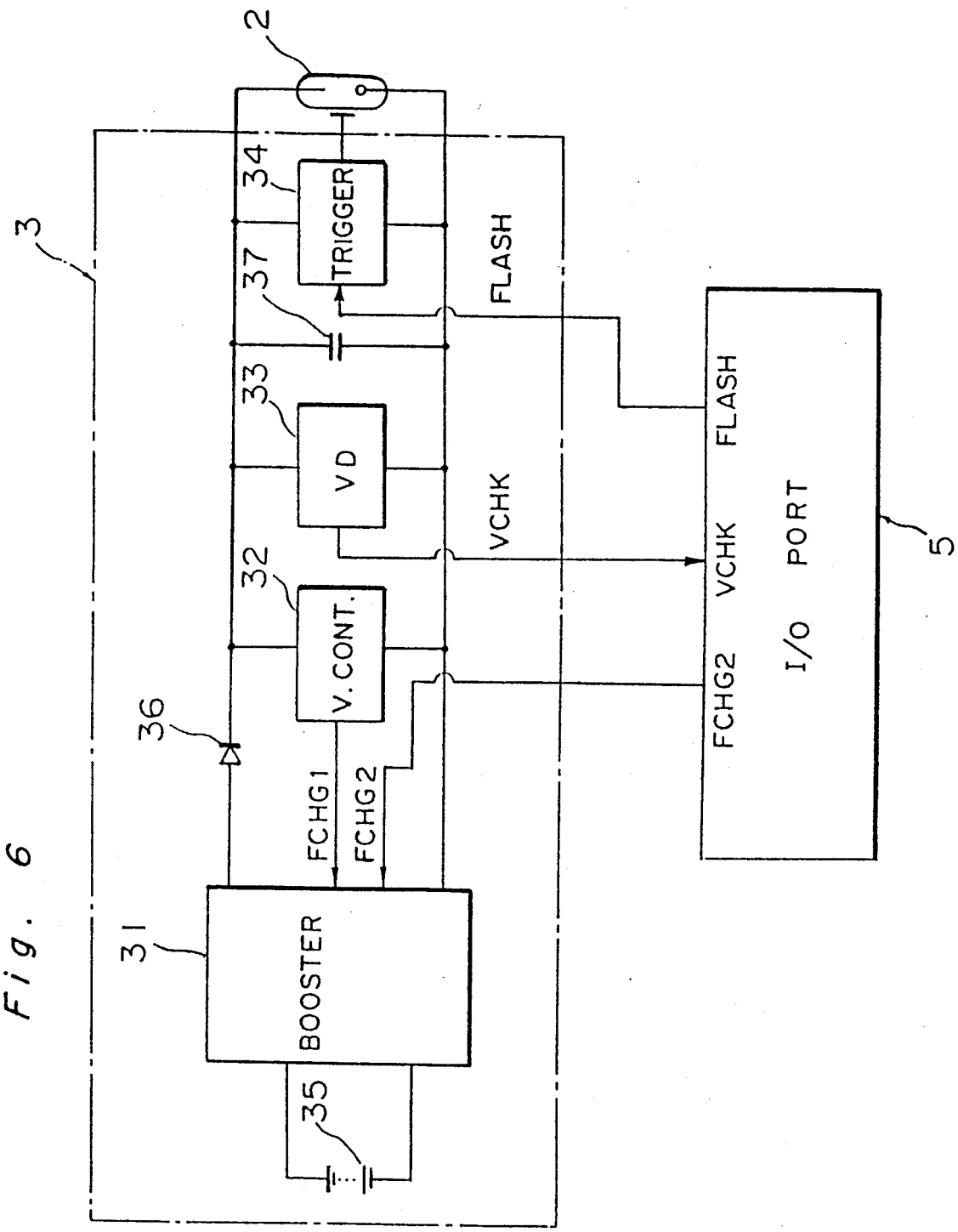
FIG. 6 is a circuit diagram of an illumination circuit used in said embodiment.

FIG. 6 is a block diagram for explanation of the illumination circuit 3. Reference numerals 2, 3, and 5 in FIG. 6 correspond to those of FIG. 1. Reference numeral 35 designates power supply for the illumination circuit 3 which is a DC power source of low voltage of the order of 9 V. Reference numeral 31 designates a booster making use of blocking oscillation, which booster supplies a source power for charging a main capacitor 37 which accumulates electric charge for flashing the pulse xenon lamp. Reference numeral 32 designates a voltage control circuit. Detecting voltage of charged electricity in the main capacitor 37, when the voltage detected is higher than a predetermined maximum voltage, the voltage control circuit 32 outputs FCHG1 at "Low" level. On the other hand, when the detected voltage of the main capacitor 37 gets lower than a predetermined minimum voltage, the circuit 32 outputs FCHG1 at "High" level. When the detected voltage is between the maximum and the minimum, the circuit 32 keeps the output level of FCHG1. The voltage control circuit 32 has such a hysteresis characteristic.

The booster 31 inputs the signal FCHG1 from the voltage control circuit 32 and a booster control signal FCHG2 outputted from the I/O port 5. The signal FCHG2 is a signal which CPU 6 makes to control the power source supply from the booster circuit 31 through the I/O port 5. In the booster 31, the signals FCHG1 and FCHG2 are inputted and when both of them are at high level, source power is supplied. Numeral 36 designates a diode which prevents electric current from counterflowing from the main capacitor 37 to the booster 31. Accordingly, while the output FCHG2 from the I/O port 5 is at "High" level, the booster 31 is controlled by the output FCHG1 from the voltage control circuit 32, and then, the charge voltage of the main capacitor 37 is controlled to be between the aforementioned maximum level and minimum level. Reference numeral 33 designates a voltage detection circuit. Comparing the charge voltage of the main capacitor 37 with a predetermined voltage at charging completion, which is either the same or lower than the minimum voltage, the voltage detection circuit 33 outputs signal VCHK "High" level to the I/O port 5 when the charge voltage is higher, and at "Low" level when it is lower. The maximum voltage, the minimum voltage and the voltage at charging completion are set within a voltage with which the pulse xenon lamp 2 can flash. CPU 6 inputs therein the output signal VCHK from the voltage detection circuit 33 through the I/O port 5, and determines whether or not the illumination circuit 3 is ready for flashing. Reference numeral 34 designates a trigger circuit for flashing the pulse xenon lamp 2. This circuit 34 makes the pulse xenon lamp 2 flash at the positive edge of signal FLASH from the I/O port 5. CPU 6 controls the signal FLASH through the I/O port 5 so as to control the flash timing of the illumination circuit 3

FIG. 7 is a timing chart showing the photometry timing according to this embodiment. FIGS. 8(a) through 8(d) are flow charts procedure to control the photometry circuit portion 4 and to calculate measured values with CPU 6. Hereinafter, the photometry operation will be described by way of FIGS. 7 and 8. At step #1 in FIG. 8(a), CPU 6 inputs therein the charging completion signal VCHK from the illumination circuit 3 through the I/O port 5. Then, CPU 6 discriminates whether or not the illumination circuit 3 can flash by detecting the output level of the signal VCHK. If VCHK is "Low", preparation for flashing has not been completed, so that the program proceeds to step #2 in which an error flag ERRF is set to be 1, and the program returns. If VCHK is at high level, preparation for flashing has been completed, so that the program proceeds to step #3 where the booster control signal FCHG2 is turned to "Low" level. When the signal FCHG2 turns low, the booster 31 stops the source power supply. It takes about 100 microseconds to stop the source power supply completely, so that time is counted at step #4. The reason for stopping of the source power supply of the booster 31 prior to the photometry is that the high voltage oscillation generated by the booster 31 during the source power supply causes noise harmful to the photometry circuit portion 4. Next, the program proceeds to step #5 at which CPU 6 makes the signal RES "Low" and the signal CHG "High" to start the integration operation. Immediately after that, CPU 6 makes the FLASH signal "High" so that the pulse xenon lamp 2 may flash at step #6. As described above, a part of the light emitted from the pulse xenon lamp 2 incides into the spectral sensor S2 for light source measurement and another part of light irradiates the test piece 1. Light reflected by the test sample 1 irradiates the spectral sensor S1 for test sample measurement. The incident light into the spectral sensors S1 and S2 is split into a plurality of light components by the band-pass filter arrays F1 and F2, and then, those light components incide into the silicon photodiode arrays PDA1 and PDA2. Each silicon photodiode in the silicon photodiode arrays PDA1, PDA2 outputs photoelectric current in proportion to the intensity of each light component. The photoelectric current outputted from each of the silicon photodiodes is converted to voltage according to the equation (2) and integrated according to the equation (3), as described in reference to the timing chart of FIG. 5. Therefore, output voltages $V2_0$ through $V2_{79}$ from the integration circuits increase in the positive direction as shown in FIG. 7. At step #7 CPU 6 counts some time (3 msec. in this embodiment) until the flashing has been finished. At step #8, the integration operation is finished with the signal CHG "Low". In this state, each of the integrated output voltages $V2_0$ through $V2_{79}$ keeps a value proportional to the time-integrated value of the intensity of the incident light into each of the silicon photodiodes. At this time, the signal FLASH is turned to a low level to prepare for next flash.

The program of CPU 6 proceeds to step #9, at which a variable N is set to be zero. The variable N is a value which is to be outputted to the input terminals A, B, C, D of the decoder IC1 shown in FIG. 4 through the I/O port 5. When the variable N is expressed by the binary notation, the 1st bit corresponds to A, the 2nd bit B, the 3rd bit C, and the 4th bit D. Next, at step #10, the output CLR of the I/O port 5 is set to high level and values of the counters IC12 through IC19 are cleared to zero. Thereafter, at step #11, the value of the variable N (N=0) is outputted from the I/O port 5 to the input terminals A, B, C, D of the decoder IC1. Then at step #12, the signal CLR is turned to low level and the signal $\overline{E}$ is turned low. As all the input signals A, B, C, D are at low level now, the signal $Q_0$ and $ADi$(i=0, 10, 20, 30, 40, 50, 60, 70) are set to high level, and accordingly, the analog switches $SW3i$, $SW4i$ (i=0,10,20,... , 60,70) are turned on so that electric current passes. Accordingly, the integrated output voltage $V2i$ (i=0, 10, 20, ..., 70) decreases linearly. At this time, the noninverting input terminals of the comparators CMP0 through CMP7 are connected to $V2_0$, $V2_{10}$, $V2_{20}$, $V2_{30}$, $V2_{40}$, $V2_{50}$, $V2_{60}$, and $V2_{70}$ through the respective analog switches $SW3_0$, $SW3_{10}$, $SW3_{20}$, $SW3_{30}$, $SW3_{40}$, $SW3_{50}$, $SW3_{60}$, and $SW3_{70}$. Let us pay attention to the voltage $V_0$. The voltage $V2_0$ is inputted to the noninverting input terminal of the comparator CMP0 through the analog switch $SW3_0$. Though the output $V2_0$ decreases linearly as mentioned above, where the output voltage $V2_0$ is higher than the reference voltage $-V_B$ of the inverting input terminal of the comparator CMP0, output C0 of the comparator CMP0 is at high level. The signal C0 is outputted to an input terminal of the two-input AND gate IC4, and NOR of the output signal of the oscillator OSC and the signal $\overline{E}$ is inputted into the other input terminal of the AND gate IC4. Therefore, into the clock input terminal CK0 of the counter IC12 is inputted a signal which is expressed by the following equation:

$$CK0 = \overline{(OSC + \overline{E})} \cdot C0 = OSC \cdot E \cdot C0 \qquad (5)$$

Accordingly, the clock pulse signal is inputted into the clock input terminal CK0 of the counter IC12 only when the comparator output C0 is at high level and the $\overline{E}$ signal at low level. Actually, the signal $\overline{E}$ is "Low" and the comparator output C0 is "High" at step #12, so, the counter IC12 is counting clock pulses. The voltage $V2_0$ decreases linearly with time to a value lower than the reference voltage $-V_B$, when the comparator output C0 is switched from "High" to "Low". When the output C0 gets to low level, the clock pulse signal input to the clock input terminal CK0 is stopped by the equation (5) and the counter IC12 also stops counting.

Accordingly, counted value CT0 of the counter IC12 is in proportion to time from that the signal $\overline{E}$ is set to low level till the output C0 is set to low level, that is, in proportion to voltage value $(V2_0 + V_B)$. With the above-mentioned procedure, the integrated value of the photoelectric current of the silicon photodiode PD0 has been analog-to-digital (A/D) converted. The voltages $V2_{10}$, $V2_{20}$, $V2_{30}$, $V2_{40}$, $V2_{50}$, $V2_{60}$, $V2_{70}$ are also A/D converted similarly to the above. Then, the counters IC13 through IC19 will have value CTk which is expressed by the following equation:

$$CTk = C_1(V2j + V_B) \qquad (6)$$

where
$C_1$ is a proportional constant,
k=0, 1, 2, ..., 7
j=k×10

As described above, each of the output terminals C0 through C7 of the comparators CMP0 through CMP7 is connected with an input of the eight-input NOR gate IC2, output ADE of which will be at high level only when all the comparator outputs C0 through C7 are at low level. In other cases than that, the output ADE will be at low level. That all of the outputs C0 through C7 get low means that A/D conversion of $V2_0$, $V2_{10}$, $V2_{20}$, $V2_{30}$, $V2_{40}$, $V2_{50}$, $V2_{60}$, $V2_{70}$ is all finished.

At step #13, CPU 6 inputs therein the signal ADE from the I/O port 5 and checks whether the signal ADE is high or low. If the signal ADE is not high, input of the ADE signal and its check are repeated. When the signal ADE gets high, the program proceeds to step #14 at which the signal $\overline{E}$ is set to high level. Then, all the outputs $Q_0$ through $Q_9$ get low and the analog switches SW4i and SW3i (i=0, 10, 20, 30, 40, 50, 60, 70) are turned off, so that the voltage of the integration output V2i (i=10, 20, 30, ..., 70) stops its linear decrease and holds its voltage level. The noninverting input of the comparator CMPk (K=0, 1, 2, ..., 7) is made high by pull-up resistor R1k and its output Ck becomes high. But, as the signal $\overline{E}$ is also high, the counters IC12 through IC19 do not carry out counting due to the equation (5) and counted values are not changed.

At step #15, CPU 6 inputs therein the counted values CT0, CT1, CT2, ..., CT7 of the counters IC12 through IC19 through the I/O port 5 and stores them in configuration variables CM1(N), CM1(N+10), CM1(N+20), ... CM1(N+70). As N is zero now, the above variables are CM1(0), CM1(10), CM1(20), ..., CM1(70). It means that A/D converted value of V2i has been stored in CM1(i) (i=0, 10, 20, ..., 70). Next, at step #16, N is given an increment of "1". Thereafter, at step #17, discrimination of N is carried out. If N is not 10, the program returns to step #10. The programs from step 10 through step #15 being carried out again, as N=1, the integration outputs $V2_1$, $V2_{11}$, $V2_{21}$, $V2_{31}$, $V2_{41}$, $V2_{51}$, $V2_{61}$, $V2_{71}$ are A/D converted and their converted values are stored in their respective configuration variables CM1(1), CM1(11), CM1(21), CM1(31), CM1(41), CM1(51), CM1(61), CM1(71) similarly to the case that N=0. At step #16, "1" is added to N, and thereafter, steps #10 through #17 are repeated till N becomes "10", during which all the integration outputs V2i are A/D converted and stored in CM1(i). The relation between V2i and CM1(i) is as follows:

$$CM1(i) = C_1(V2i + V_B) \qquad (7)$$

When it is judged that N=10 at step #17, the A/D conversion of all the integration outputs is considered to be finished. Therefore, at step #18, the signal RES is set to high level, the analog switch SW2i in parallel with the integration capacitor Cci (i=0, 1, 2, ..., 79) is turned on and electric charge of the integration capacitor Cci is turned "0". Moreover, at the same step, "0" is outputted to the input terminals A, B, C and D of the decoder IC1 so that they may be at the initial state.

Figure 8A:
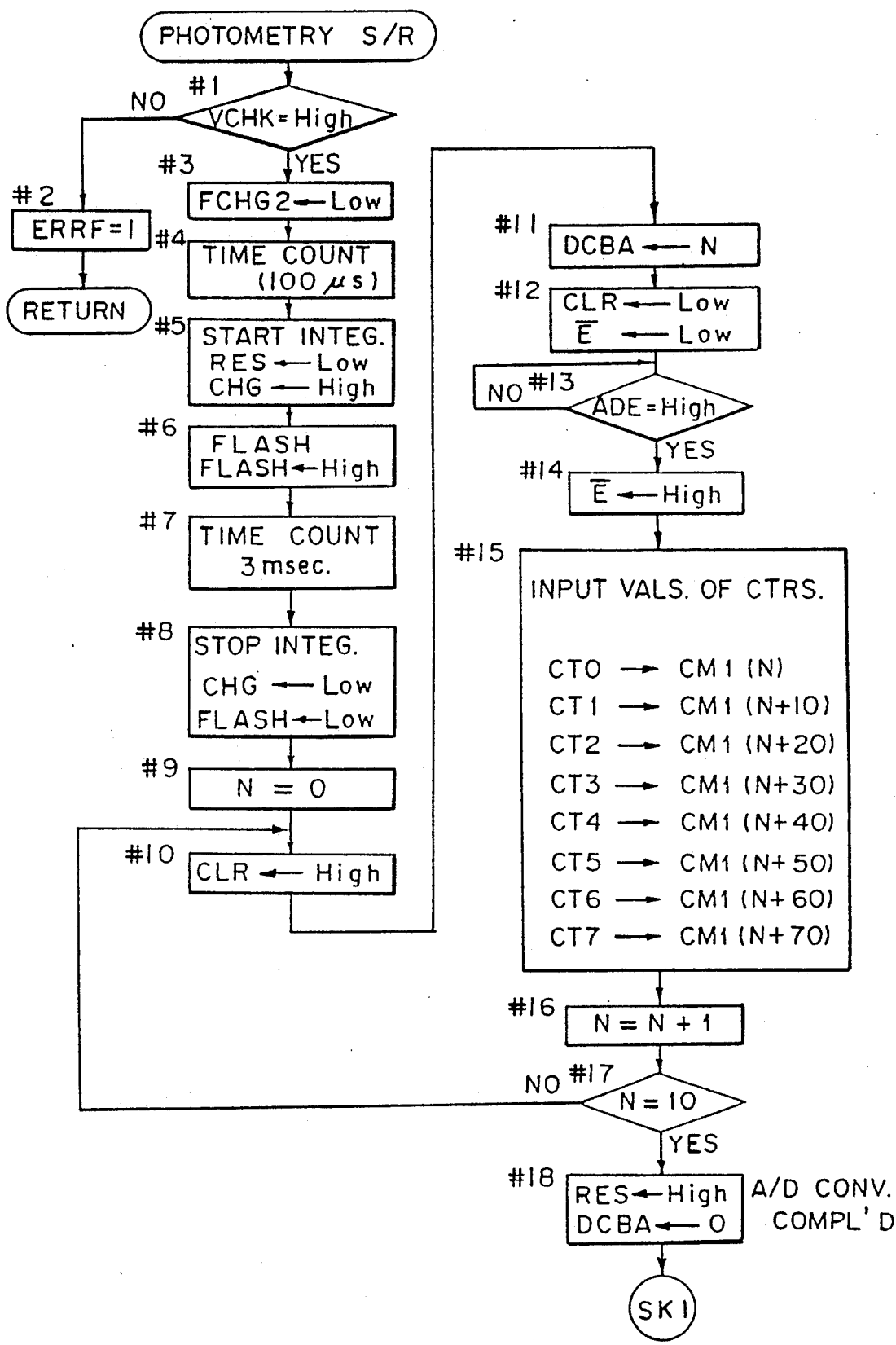
FIGS. 8(a) through 8(d) are flow charts showing a photometric operation in said embodiment.
Figure 8B:
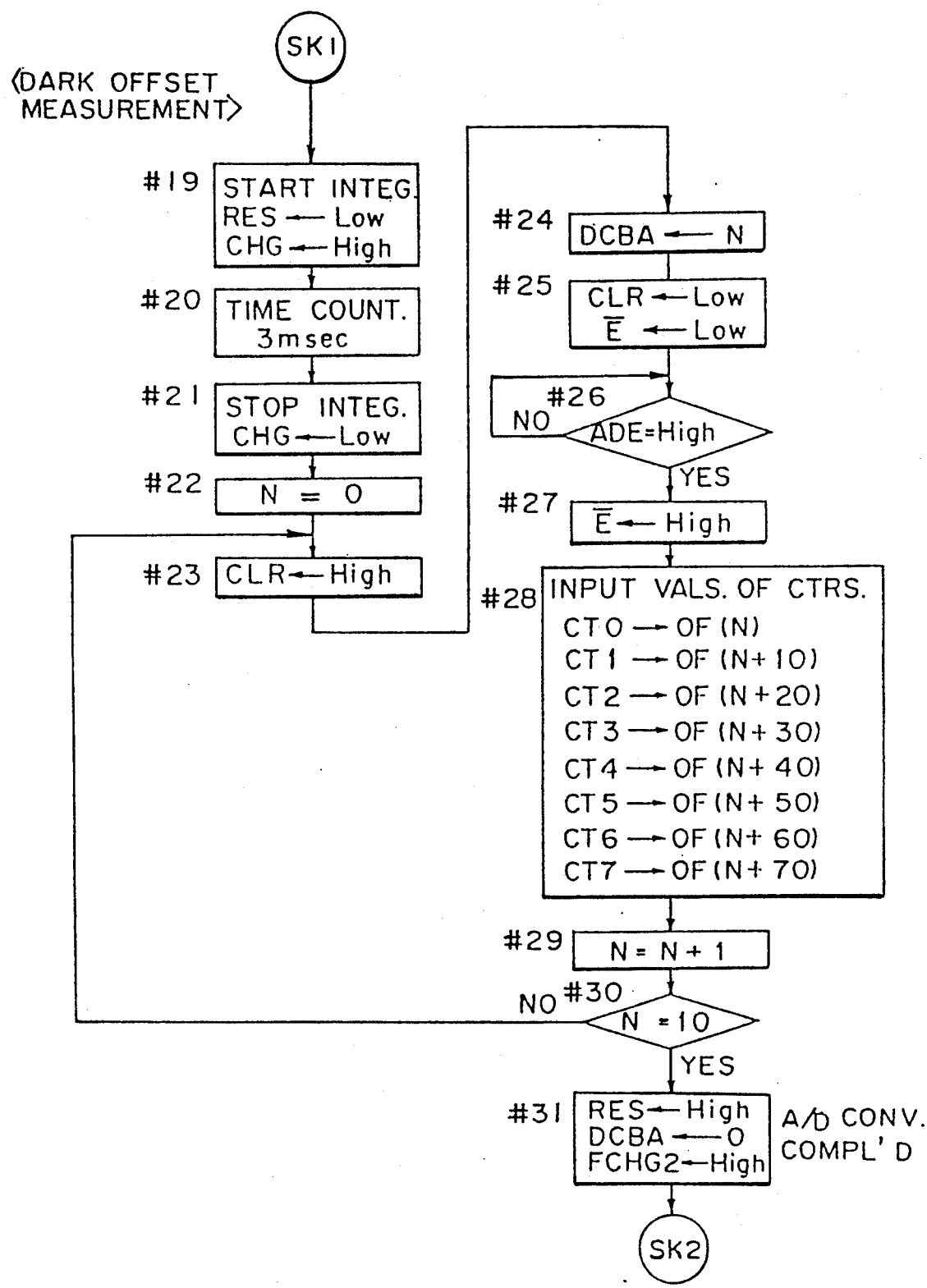

The program proceeds to step #19 of FIG. 8(b), at which measurement of a dark offset is started. Timing chart for the dark offset measurement is omitted because its process is almost the same as the above-mentioned steps #5 through #18 where the measurement is done by flashing the pulse xenon lamp 2, except for that, in this case, the pulse . xenon lamp 2 does not flash and that source power supply by the booster 31 is started again after the measurement by making the booster control signal FCHG2 "High" at step #31. At steps #19 through #21, the integration output V2i (i=0, 1, 2, ..., 79) is obtained in the state where the pulse xenon lamp 2 does not flash and at steps #22 through #31 all the integration outputs are A/D converted and stored in their respective configuration variables OF(i). OF(i) is a value which contains influences of an offset of the operational amplifier, external light, dark current of the silicon photodiodes, leakage current of the analog switches, etc.. Errors due to the influences of those factors can be removed by subtracting OF(i) from CM1(i) which is a measured value obtained with the pulse xenon lamp 2 flashing. As the pulse xenon lamp 2 is used as a light source in this embodiment, the dark offset can be measured without chopping light as usually done with light source having constant intensity, and accordingly, there is an advantage that a mechanical drive portion is not required.

Figure 8C:
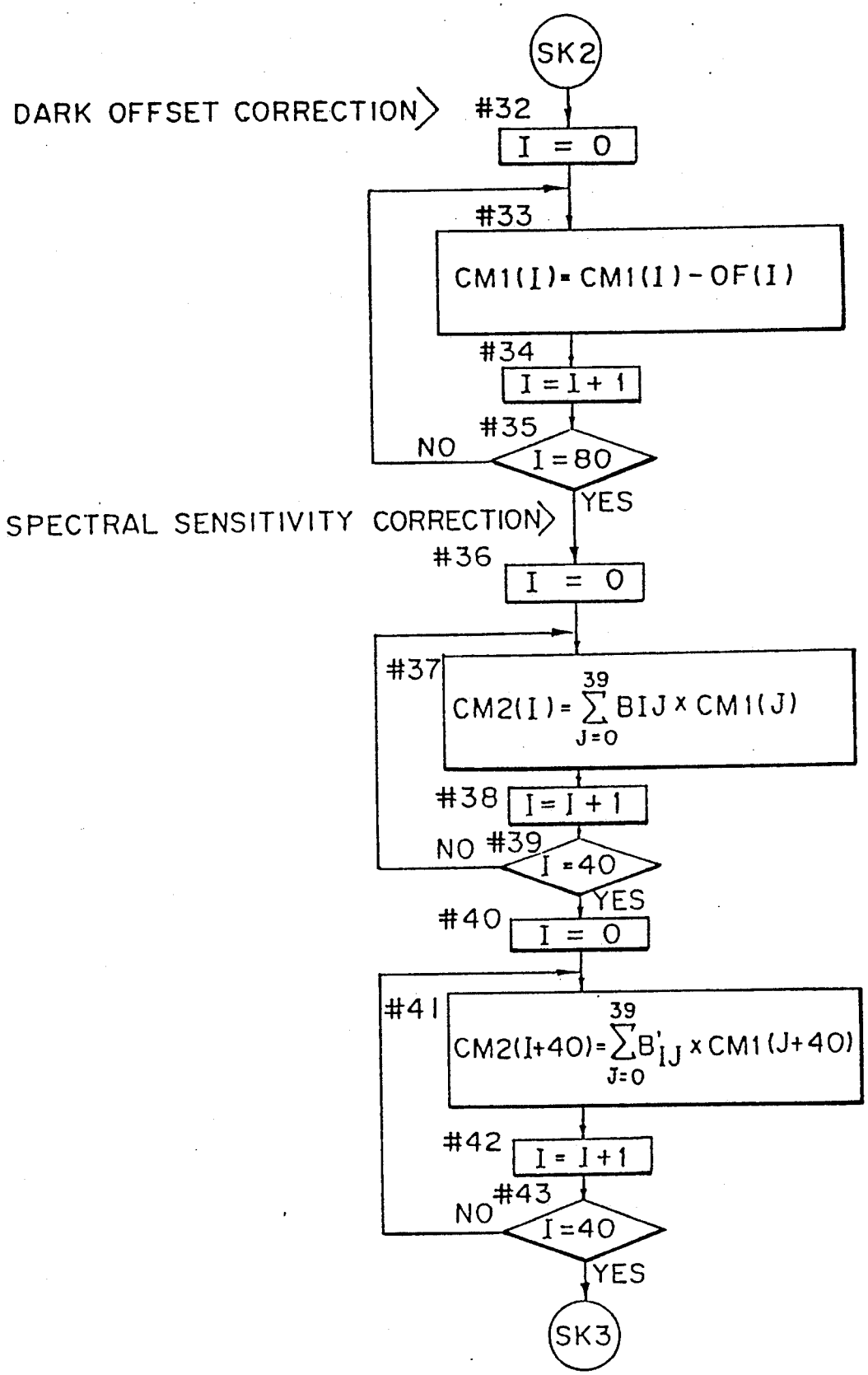

At steps #32 through #35 of FIG. 8(c), correction of the above dark offset is carried out. A value obtained by subtracting OF(i), a measured value of the dark offset, from CM1(i), a measured value with the pulse xenon lamp 2 flashing, is stored in CM1(i). From step #36 on, calculation of the spectral sensitivity correction is carried out.

Figure 9A:
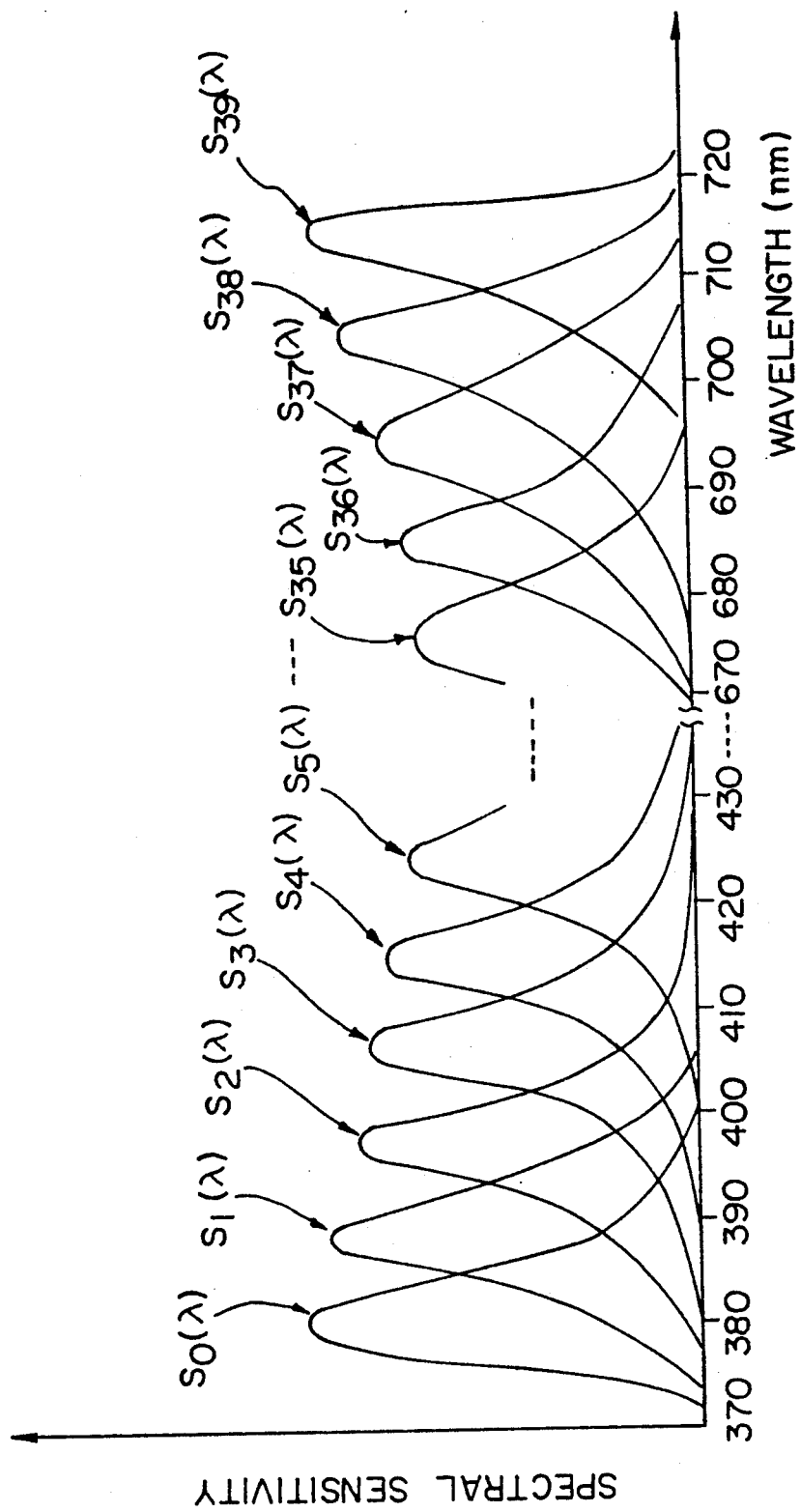
FIG. 9(a) is a diagram showing spectral sensitivity of the photometry circuit in said embodiment.

Now, the signification and principle of the spectral sensitivity correction will be described. FIG. 9(a) shows a chart where the spectral sensitivity $Si(\lambda)$ (i=0, 1, 2, ..., 39) as a photometry circuit system is plotted. The spectral sensitivity $Si(\lambda)$ is a value obtained by multiplying the photoelectric current I1i of each silicon photodiode in the spectral sensor S1 used in this embodiment by the amplification factor of the corresponding current-voltage conversion and integration circuit AN(i) (i=0, 1, 2, 3, ..., 39), where $\lambda$ is wavelength of light. The band-pass filter arrays F1, F2 of the spectral sensors S1, S2 have been treated so that they may cut off the infrared and ultraviolet rays. So, each of the spectral sensitivities $S0(\lambda)$ through $S39(\lambda)$ is almost zero in the wavelength range shorter than 370 nm and longer than 720 nm. According to the chart, $S0(\lambda)$ through $S39(\lambda)$ are located with a pitch of 10 nm and the half-width of the band-pass filters is wider than 10 nm. The spectral sensors have sensitivity even in the wavelength region remote from the peak wavelength because of the influence of the internal reflection between the band-pass filter array and the photodiode array, etc., which we call "skirt" of the spectral sensitivity. Measured values have errors due to the "skirt" of the spectral sensitivity and the wide half-width. Calculation for the spectral sensitivity correction is to obtain correct measured values from the output from a sensor with such properties.

Figure 9B:
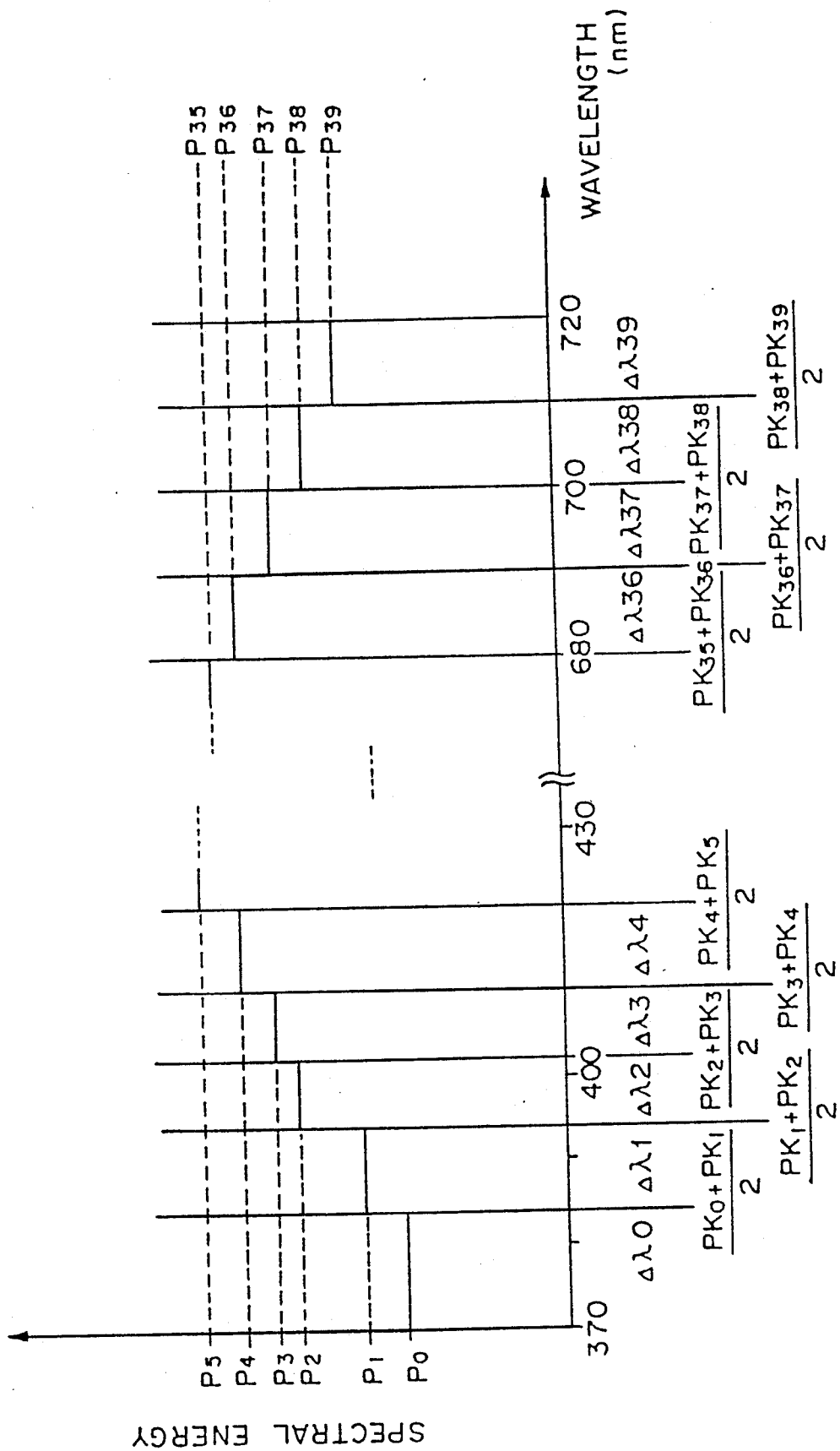
FIG. 9(b) is an explanatory diagram for explaining division of the wave length region in said embodiment.

Assume that the peak wavelength of the spectral sensitivity $Si(\lambda)$ (i=0, 1, 2, ..., 39) is PKi (i=0, 1, 2, ..., 39). Measurement wavelength region (in this embodiment, it is from 370 to 720 nm) is divided into 40 regions $\Delta\lambda i$ (i=0, 1, 2, ..., 39) at the wavelengths of (PKi+PKi+1)/2 (i=0, 1, 2, ..., 39). Assume that the spectral energy distribution of the light inciding into the spectral sensor S1 is substantially flat in each of the forty wavelength regions as shown in FIG. 9(b) and that the light intensity (spectral energy) in the region $\Delta\lambda i$ is Pi. Then, assuming that the output of a sensor having the spectral sensitivity $Si(\lambda)$ is Oi (i=0, 1, 2, ..., 39), Oi is expressed with the following equation:

$$Oi = P_0 \int_{370}^{\frac{PK_0 + PK_1}{2}} Si(\lambda)d\lambda + \sum_{j=1}^{38} P_j \int_{\frac{PK_{j-1} + PK_j}{2}}^{\frac{PK_j + PK_{j+1}}{2}} Si(\lambda)d\lambda + P_{39} \int_{\frac{PK_{38} + PK_{39}}{2}}^{720} Si(\lambda)d\lambda \quad (8)$$

$a_{ij}$ is defined as follows:

$$a_{i0} = \int_{370}^{\frac{PK_0 + PK_1}{2}} Si(\lambda)d\lambda \quad (9)$$

$$a_{ij} = \int_{\frac{PK_{j-1} + PK_j}{2}}^{\frac{PK_j + PK_{j+1}}{2}} Si(\lambda)d\lambda \quad (j = 1, \ldots, 38)$$

$$a_{i39} = \int_{\frac{PK_{38} + PK_{39}}{2}}^{720} Si(\lambda)d\lambda$$

With this definition, the equation (8) is expressed as follows:

$$Oi = \sum_{j=0}^{39} p_j \cdot a_{ij} \quad (10)$$

As the above equation holds for $i = 0 \sim 39$, the following equation using a matrix also holds:

$$\begin{bmatrix} O_0 \\ O_1 \\ O_2 \\ \cdot \\ \cdot \\ O_n \end{bmatrix} = \begin{bmatrix} a_{00} & a_{01} & \cdots & a_{0n} \\ a_{10} & a_{11} & \cdots & a_{1n} \\ a_{20} & a_{21} & \cdots & a_{2n} \\ \cdot & \cdot & & \cdot \\ \cdot & \cdot & & \cdot \\ a_{n0} & a_{n1} & \cdots & a_{nn} \end{bmatrix} \begin{bmatrix} P_0 \\ P_1 \\ P_2 \\ \cdot \\ \cdot \\ P_n \end{bmatrix} \quad (11)$$

where $n = 39$.

Expressing the above matrix as follows:

$$O = A \cdot P \quad (12)$$

where, $$O = \begin{bmatrix} O_0 \\ O_1 \\ O_2 \\ . \\ . \\ O_n \end{bmatrix}, \quad A = [a_{ij}], \quad P = \begin{bmatrix} P_0 \\ P_1 \\ P_2 \\ . \\ . \\ P_n \end{bmatrix}$$

From the equation (12):

$$P = A^{-1} \cdot O \tag{13}$$

where $A^{-1}$ is an inverse matrix of the matrix A. Accordingly, if $A^{-1}$ is obtained, the spectral energy distribution P of the incident light can be obtained from the output O of the spectral sensor S1 by the equation (13). $A^{-1}$ is calculated in the following way. First, the spectral sensitivity $S0(\lambda) \sim S39(\lambda)$ of the spectral sensor is measured using a spectroscope. Then, matrix $A = [a_{ij}]$ is calculated according to the equation (9) so as to obtain the inverse matrix $A^{-1}$ of the matrix A.

The above description was given about the spectral sensor S1 for test piece measurement as an example, though it is similar with the spectral sensor S2 for light source measurement. As mentioned above, the spectral energy values are approximate in each wavelength region $\Delta\lambda i$ so that the spectral energy distribution is flat in each wavelength region. This embodiment is for measuring a spectral reflectance of a reflective object. Generally, many of spectral reflectances of reflective objects such as paint, print, and the like describe gentle curves and do not have acute absorption. This is why the spectral energy distribution in each wavelength approximates to be flat.

Now again, description will be done according to the flow chart of FIG. 8(c). $A^{-1}$ in the equation (13) with the spectral sensor S1 for test piece measurement (sensor for samples) is assumed to be $B = [B_{ij}]$. Similarly, $A^{-1}$ in the same equation with the spectral sensor S2 for light source measurement (sensor for a reference) is assumed to be $B' = [B'_{ij}]$. Calculation for the spectral sensitivity correction according to the equation (13) is carried out with the spectral sensor S1 for test piece measurement at steps #36 through #39, and with the spectral sensor S2 for light source measurement at steps #40 through #43. The equation (13) will be as follows, with the spectral sensor S1:

$$Pi = \sum_{j=0}^{39} B_{ij} \cdot Oj \tag{14}$$

The output $Oi$ ($i = 0, 1, 2, \ldots, 39$) of the spectral sensor S1 is stored in CM1(i). Now, assuming that Pi calculated by the equation (14) is stored in CM2(i):

$$CM2(i) = \sum_{j=0}^{39} B_{ij} \cdot CM1(j) \tag{15}$$

$(i = 0, 1, 2, \ldots, 39)$

With respect to the spectral sensor S2, the equation (13) is expressed as follows:

$$Pi = \sum_{j=0}^{39} B'_{ij} \cdot Oj \tag{16}$$

The output of the spectral sensor S2 is now stored in CM1(i+40) (i=0, 1, 2, ..., 39). Then, if Pi calculated by the equation (16) is stored in CM2(i+40):

$$CM2(i + 40) = \sum_{j=0}^{39} B'_{ij} \cdot CM1(j + 40) \tag{17}$$

$(i = 0, 1, 2, \ldots, 39)$

Values $B_{ij}$ and $B'_{ij}$ are stored in the data storage portion 9 of the spectral sensors in advance.

Figure 8D:
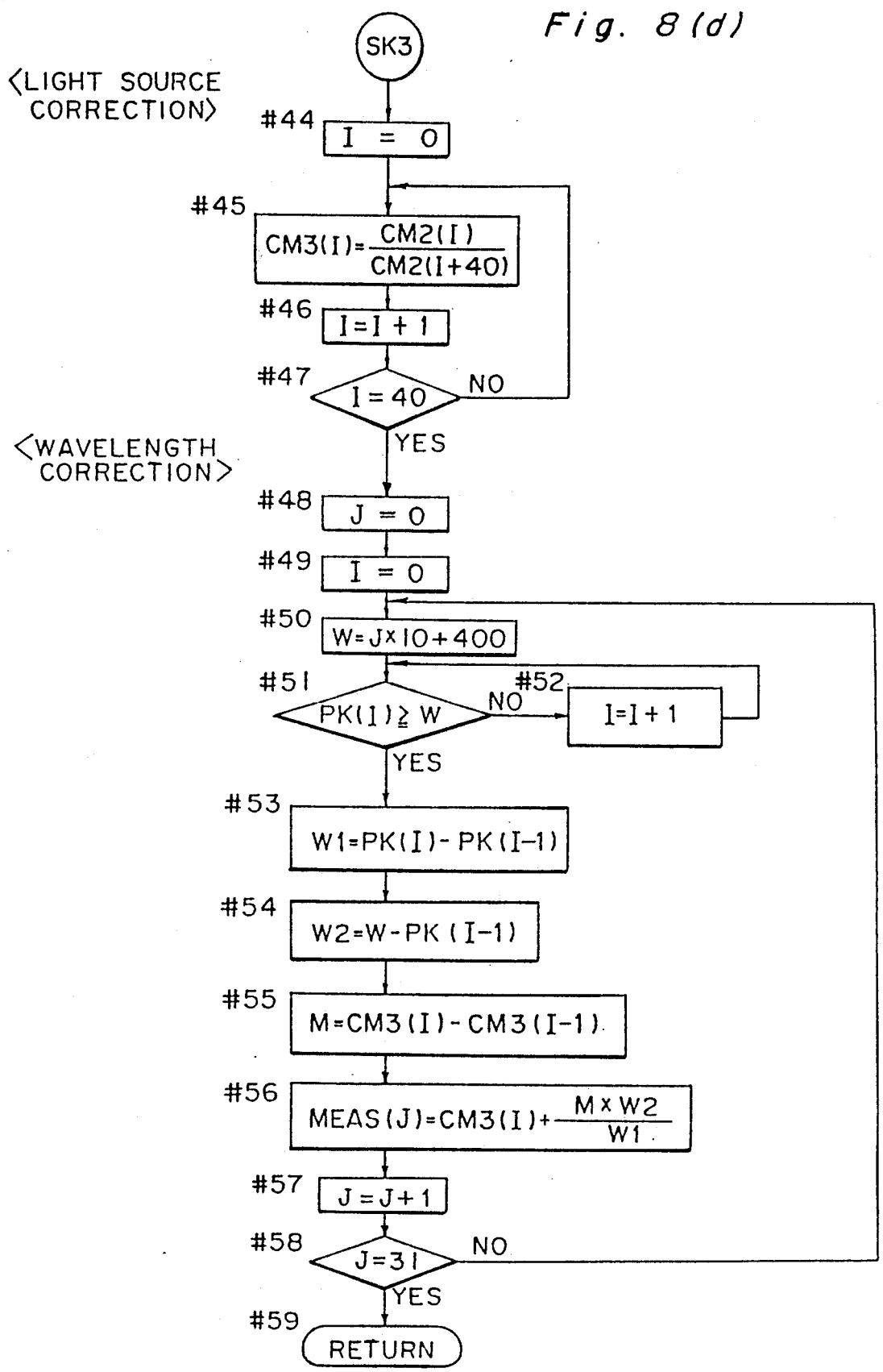

Now, the program proceeds to step #44 of FIG. 8(d), at which calculation for light source correction is carried out. Light source for illumination is the pulse xenon lamp 2 in this embodiment. Its spectral energy distribution varies a little at each time of illumination. The spectral sensor S2 for light source measurement measures spectral energy distribution of the pulse xenon lamp 2 with almost the same wavelength regions as those of the spectral sensor S1 for test piece measurement. Therefore, if the spectral energy distribution of the sample light measured by the spectral sensor S1 is divided by the spectral energy distribution of the light source measured by the spectral sensor S2 in every corresponding wavelength region and values so obtained are considered as measured values, errors caused by the variation of the spectral energy distribution of the light source can be removed. Such calculation is carried out at steps #44 through #47. Referring to step 45, CM2(I) is a measured value relative to Ith silicon photodiode of the spectral sensor S1 and CM2(I+40) is a measured value relative to Ith silicon photodiode of the spectral sensor S2. Value obtained by dividing CM2(I) by CM2(I+40) is put in CM3(I). This operation is repeated from I=0 to I=39 until correction of all measured values and storage thereof into CM3(I) are completed. With the above procedure, correction of the spectral energy distributional variation of the light source for illumination has been completed and the corrected values have been stored in CM3(i) (i=0, 1, 2, ..., 39).

Next, the program proceeds to step #48 to start calculation of wavelength correction. First of all, it will be described what the calculation of wavelength means. In the spectral sensors S1 and S2 of this embodiment, the bandpass filter arrays are used. Peak wavelengths of the bandpass filters are at intervals of about 10 nm, though there exists a little variation in the pitch of wavelengths. Correction of scattering of the wavelength pitch to 10 nm is carried out by the linear interpolation method. This is what the calculation of wavelength correction means.

Figure 10:
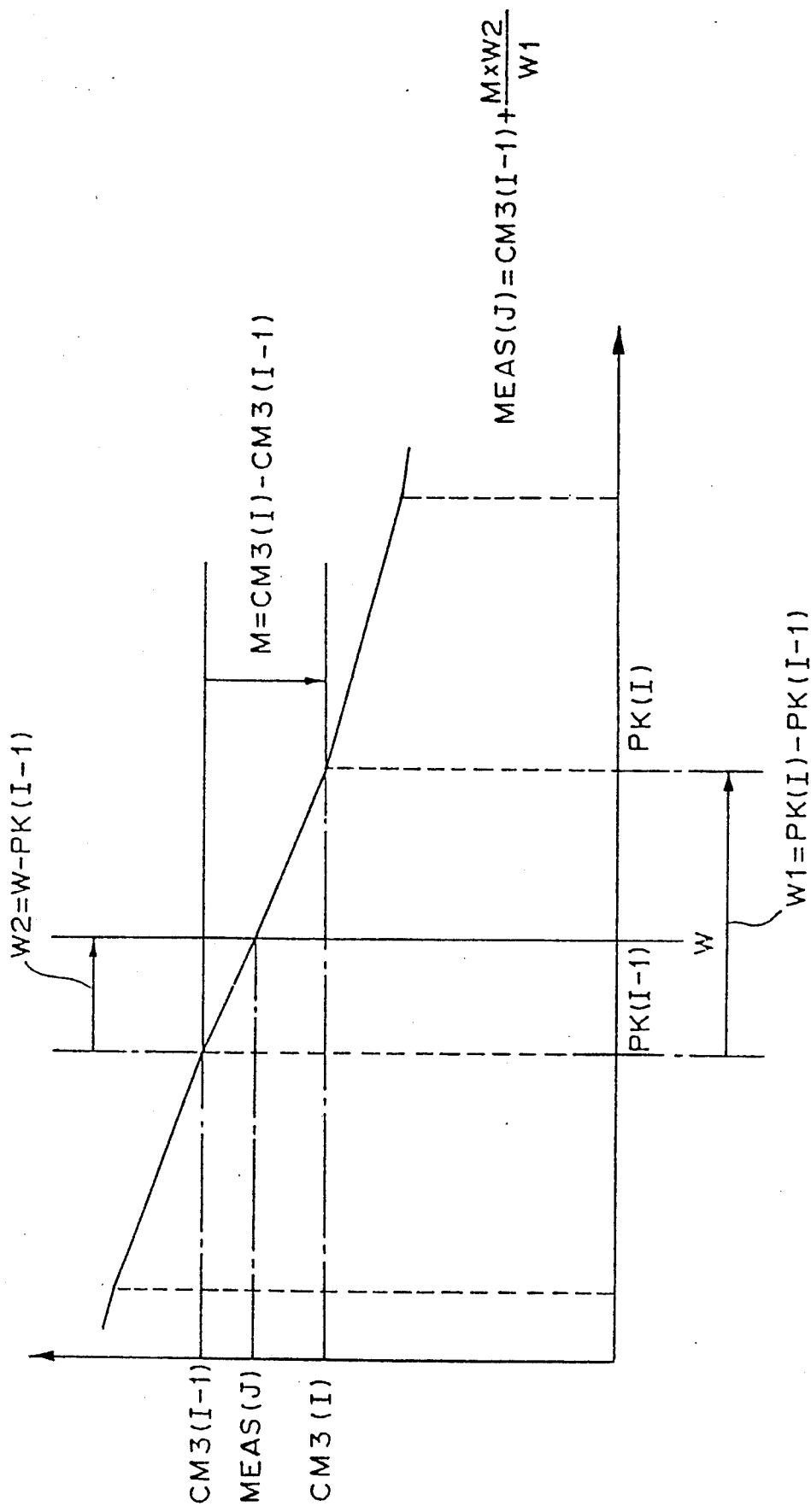
FIG. 10 is an explanatory diagram for explaining correction of the wave length in said embodiment.

At step #48 of FIG. 8(d), let J (wavelength No.) be 0. J is a wavelength number for wavelengths at intervals of 10 nm in the wavelength region from 400 to 700 nm, that is, when the wavelength is 400 nm, J=0, and value of J increases by 1 each time the wavelength increases by 10 nm. I is sensor No. and this number is initialized to zero at step #49. I=0 is given to number of a sensor which has the minimum peak wavelength, and sensors which have longer peak wavelengths are given sensor numbers I which increase by one in order. At step #50, wavelength W corresponding to the wavelength No. J is calculated. At step #51, the peak wavelength PK(I) of the Ith sensor is compared with the Jth wavelength W. If PK(I)<W, increment of "1" is given to I at step #52 and the program returns to step #51. If PK(I)≧W, the program proceeds to step #53. In short, at steps #51 and #52 is detected the number of a sensor whose peak wavelength is longer than the Jth wavelength W but approximates that W most. At steps #53 through #55, calculation of values W1, W2, and M is carried out as shown in FIG. 10. The value W1 is a difference between PK(I), the peak wavelength of the sensor detected at steps #51 and #52, and PK(I-1), the peak wavelength of the (I-1)th sensor. W2 is a difference between W and PK(I-1). M is a difference between the measured value CM3(I) of the Ith sensor and that CM3(I-1) of the (I-1)th sensor. At step #56, measured value for the wavelength W is calculated through the linear interpolation using the measured values of the Ith sensor and of the (I-1)th sensor and let the value obtained be MEAS(J). At step #57, increment of "1" is given to the wavelength No. J. Thereafter, at step #58, it is discriminated whether or not J is 31 to discriminate whether or not the process of steps #50 through #56 with all the range from 400 to 700 nm has been completed. If the result of the discrimination is that J is not 31, the program returns to step #50 and measured value for the next wavelength is calculated by the interpolation method. J=31 means that measured values for every 10 nm in the range from 400 to 700 nm have been obtained by the interpolation method. So, the program proceeds to the next step #59, at which the photometry subroutine is completed and the program returns. Process from step #49 to step #54 in this embodiment is for help of understanding. But the steps #49, #51~#54 may be omitted if sensor No. corresponding to wavelength W, values W1, W2, etc. are calculated in advance and stored in the spectral sensor data storage portion 9.

Figure 25:
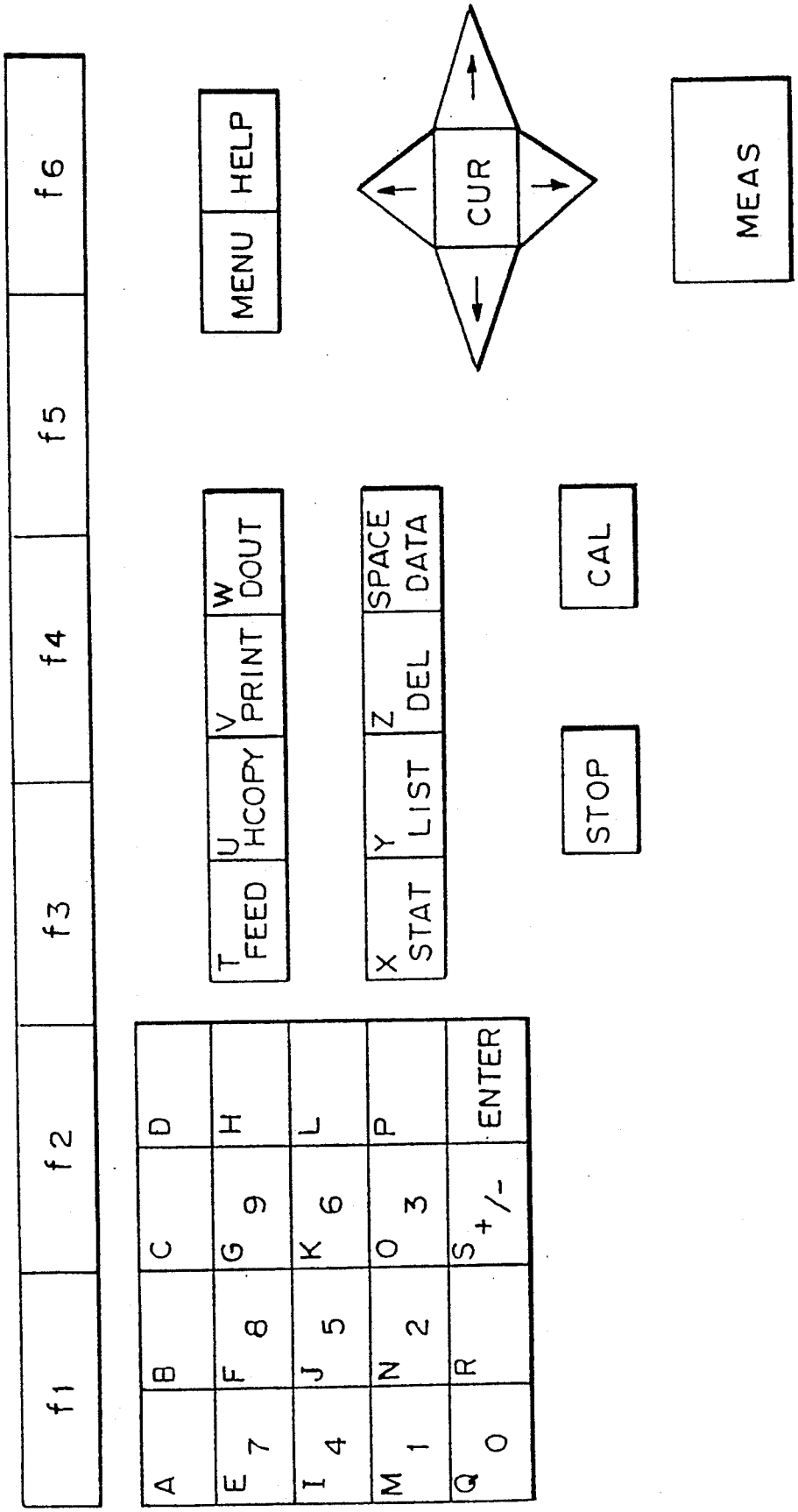
FIG. 25 is a diagram showing an example location of a keyboard to be used in said embodiment.

Apart from the photometry circuit operation and the operation processing for correction which have been described, the function and action of the whole system will be described hereinafter with reference to the flow chart shown in FIGS. 11(a) through 17. Turning the power switch of the system on, the program proceeds to step #100 of FIG. 11(a), at which initial setting is carried out with I/O port 5, the external I/O port 10, the magnetic memory control portion 11, the display control portion 13, the keyboard 15, and the printer 16. Then at step #101, memories in the data storage portion 8 and data set are initialized. Thereafter, at step #102, a display subroutine is carried out and at step #103, it is discriminated whether or not a key has been depressed. The display subroutine will be described in detail later. If a key has been depressed, the program proceeds to step #105 of FIG. 11(b). If not, a present hour is inputted from the real time clock 17 and displayed at step #104. After that, the program returns to step #103. FIG. 25 shows an example of key configuration on the keyboard to be used for this embodiment.

Figure 11A:
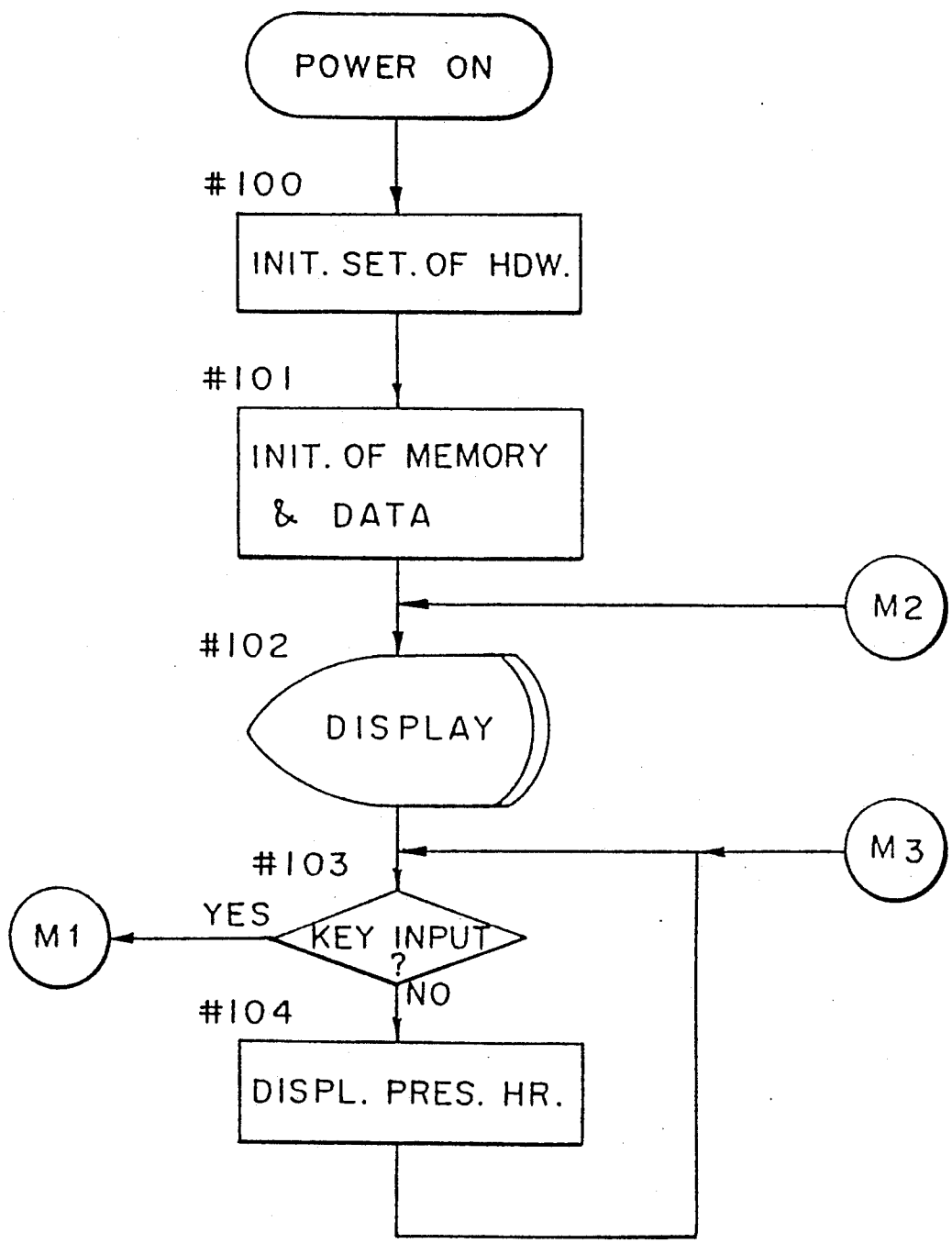
FIGS. 11(a) through 11(c) are flow charts for explaining the operation of the whole system in said embodiment.
Figure 11B:
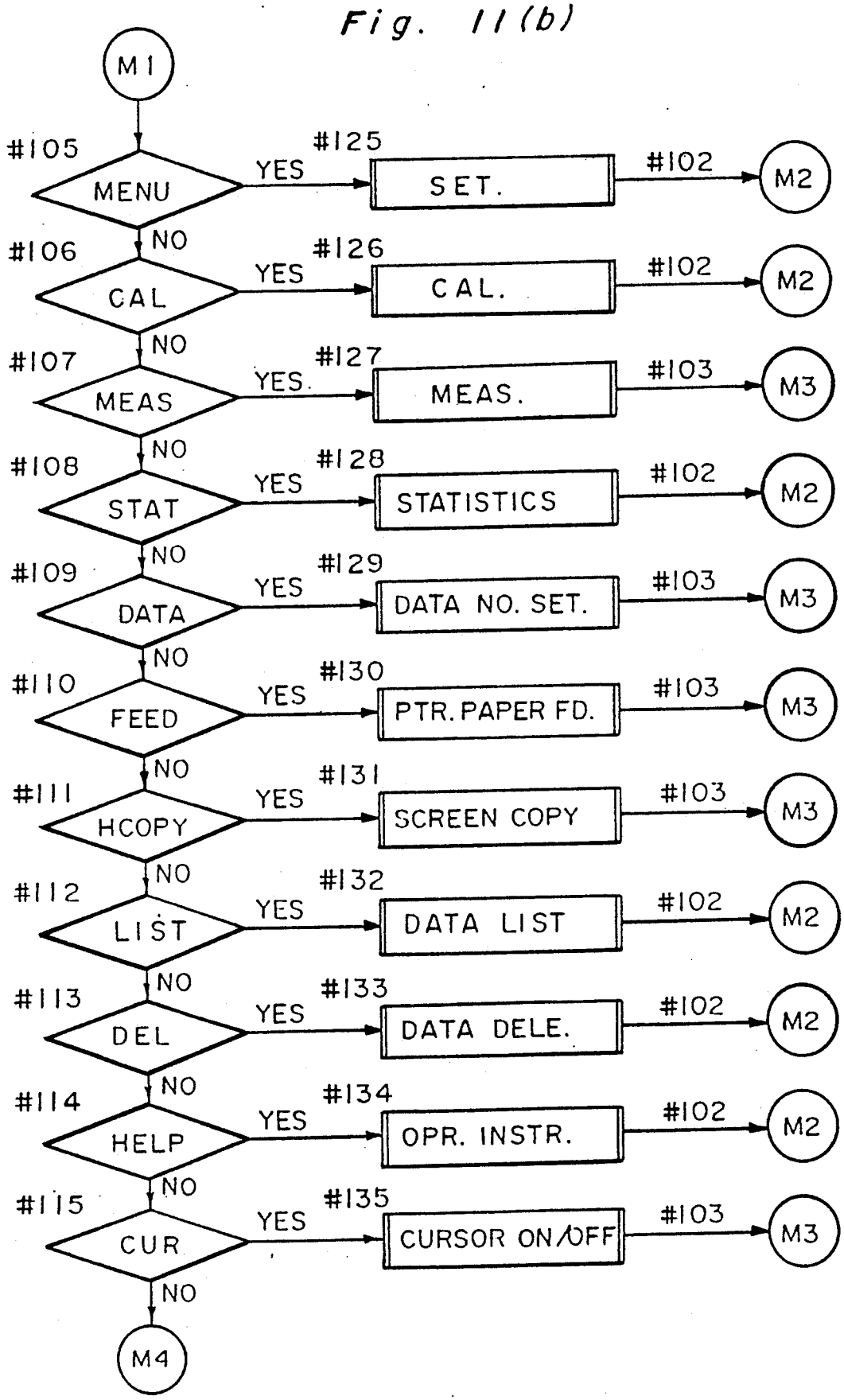

At step #105 of FIG. 11(b), it is discriminated whether or not the key being depressed is "MENU" key. If so, a setting subroutine for the process related to setting is carried out at step #125, and then, the program returns to step #102. If the key is not "MENU", the program proceeds to step #106, at which it is discriminated whether or not the depressed key is "CAL". If so, a calibration subroutine for the process related to calibration by means of a standard reflection plate and the program returns to step #102 If the depressed key is not "CAL", the program proceeds to step #107, at which it is discriminated whether or not the depressed key is "MEAS". If it is, a measurement subroutine for the process related to measurement is carried out at step #127 and the program returns to step #103. It is noted that the measurement subroutine here is different from the photometry subroutine above-mentioned, which will be described later. If the key is not "MEAS", the program proceeds to step #108, at which it is discriminated whether or not the depressed key is "STAT". If it is so, the program proceeds to step #128, at which a statistics subroutine for the process related to statistical calculation of measured values is carried out and then, the program returns to step #102. If the key is not "STAT", the program proceeds to step #109, at which it is discriminated whether or not the depressed key is "DATA". If it is, the program proceeds to step #129, at which a data number setting subroutine for the process related to setting of the data No. of measured data to be displayed is carried out, and then, the program returns to step #103. If the key is not "DATA", the program proceeds to step #110, at which it is discriminated whether or not the depressed key is "FEED". If it is so, the program proceeds to step #130, at which a paper feeding subroutine for feeding paper in the printer 16 is carried out and after that, the program goes back to step #103. If the key is not "FEED", the program proceeds to step #111, at which discrimination whether or not the depressed key is "HCOPY" is performed. If the answer is yes, the program proceeds to step #131, at which a screen copy subroutine is carried out for copying display on the screen into the printer 16 and then, the program returns to step #103. Unless the key is "HCOPY", the program proceeds to step #112, where it is discriminated whether or not the depressed key is "LIST". If it is "LIST", the program proceeds to step #132, at which a data list subroutine is carried out for the process of displaying a list of numerical data of measured values on the display portion 14, or printing it out by the printer 16, or outputting it to the external I/O port 10. Thereafter, the program returns to step #102. If not, the program proceeds to step #113, at which it is discriminated whether or not the depressed key is "DEL". If it is, the program proceeds to step #133, at which a data deleting subroutine is carried out for the process of deleting the measurement data on display. Then the the program returns to step #102. If the key is not "DEL", the program proceeds to step #114, at which it is discriminated whether or not the depressed key is "HELP". If the answer is affirmative, the program proceeds to step #134, at which an operation instructions subroutine is carried out for displaying the instructions for the operation of the system. Then, the program returns to step #102. If the answer is negative, the program proceeds to step #115, at which it is discriminated whether or not the depressed key is "CUR". If it is "CUR", the program proceeds to step #135, at which a cursor ON/OFF subroutine is carried out for the process of deciding to display or not to display a cursor on a graph of spectral measurement values. Thereafter, the program returns to step #103. If the key is not "CUR", the program proceeds to step #116 of FIG. 11(c), at which it is discriminated whether or not the depressed key is "→". If it is, the program proceeds to step #136, at which a cursor right shifting subroutine is carried out for shifting the above-mentioned cursor to be displayed on the graph of the measured spectral values in the right direction, and then, the program returns to step #103. If the key is not "→", the program proceeds to step #117, at which it is discriminated whether or not the depressed key is "←". If the answer is affirmative, the program proceeds to step #137, at which a cursor left shifting subroutine is carried out for shifting a cursor to be displayed on the graph of spectral reflectance in the left direction. Thereafter the program returns to step #103 If the answer is negative, the program proceeds to step #118, at which it is discriminated whether or not the depressed key is "DOUT". With the affirmative answer, the program proceeds to step #138, at which a data output subroutine is carried out for the process of outputting the measured data to the external I/O port 10. After that, the program returns to step #103. If the key is not "DOUT", the program proceeds to step #119, at which it is discriminated whether or not the depressed key is "PRINT". If it is, the program proceeds to step #139, at which a data print subroutine is carried out for the process of printing out the measured data by the printer 16, and then the program returns to step #103. If not, the program proceeds to step #120, at which it is discriminated whether or not the depressed key is "f1". With the affirmative answer, the program proceeds to step #140, where a range setting subroutine is carried out for setting a scale and a graph display range for the graphs indicating spectral measurement values or measured chromaticity values. Thereafter, the program returns to step #103. On the other hand, with the negative answer, the program proceeds to step #121, at which it is discriminated whether or not the depressed key is "f2". With the affirmative answer, the program proceeds to step #141, at which a grid ON/OFF subroutine is carried out for deciding to or not to display a grid serving as a scale cover the above-mentioned graphs. Then, the program returns to step #103. If the key is not "f2", the program proceeds to step #122, at which it is discriminated whether or not the depressed key is "f3". If the answer is "yes", the program proceeds to step #142, at which a colorimetric system setting subroutine is carried out for setting which colorimetric system should be used for the color value calculation. Thereafter the program returns to step #10. The key not being "f3", the program proceeds to step #123, at which it is discriminated whether or not the depressed key is "f4". If it is, the program proceeds to step #143, at which a reference value ON/OFF subroutine is carried out for deciding either to or not to display a reference value along with the measured value. After the completion of the subroutine, the program returns to step #103. If the key is not "f4", the program proceeds to step #124, at which it is discriminated whether or not the depressed key is "f6". If the answer is "yes", the program proceeds to step #144, at which a display mode setting subroutine for the process of setting the style of a graph to be displayed and the unit of the measured value is carried out. Thereafter the program returns to step #102. If the key is not "f6", the program returns to step #103.

That is all for the brief description about the various processes to be carried out at the time of corresponding key pushing. Of the above processes, principal ones will be described in detail hereinafter.

Figure 12A:
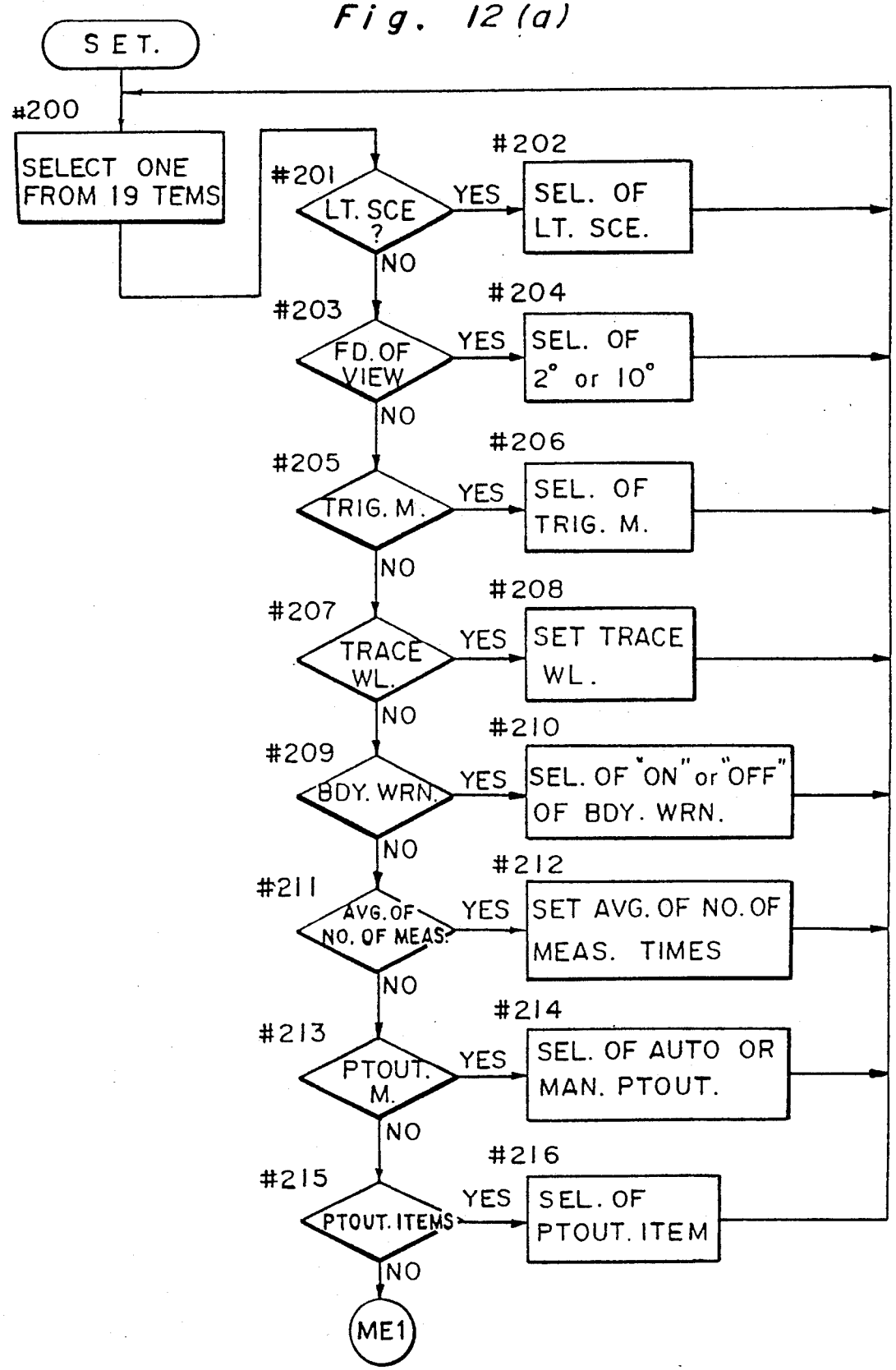
Figure 12C:
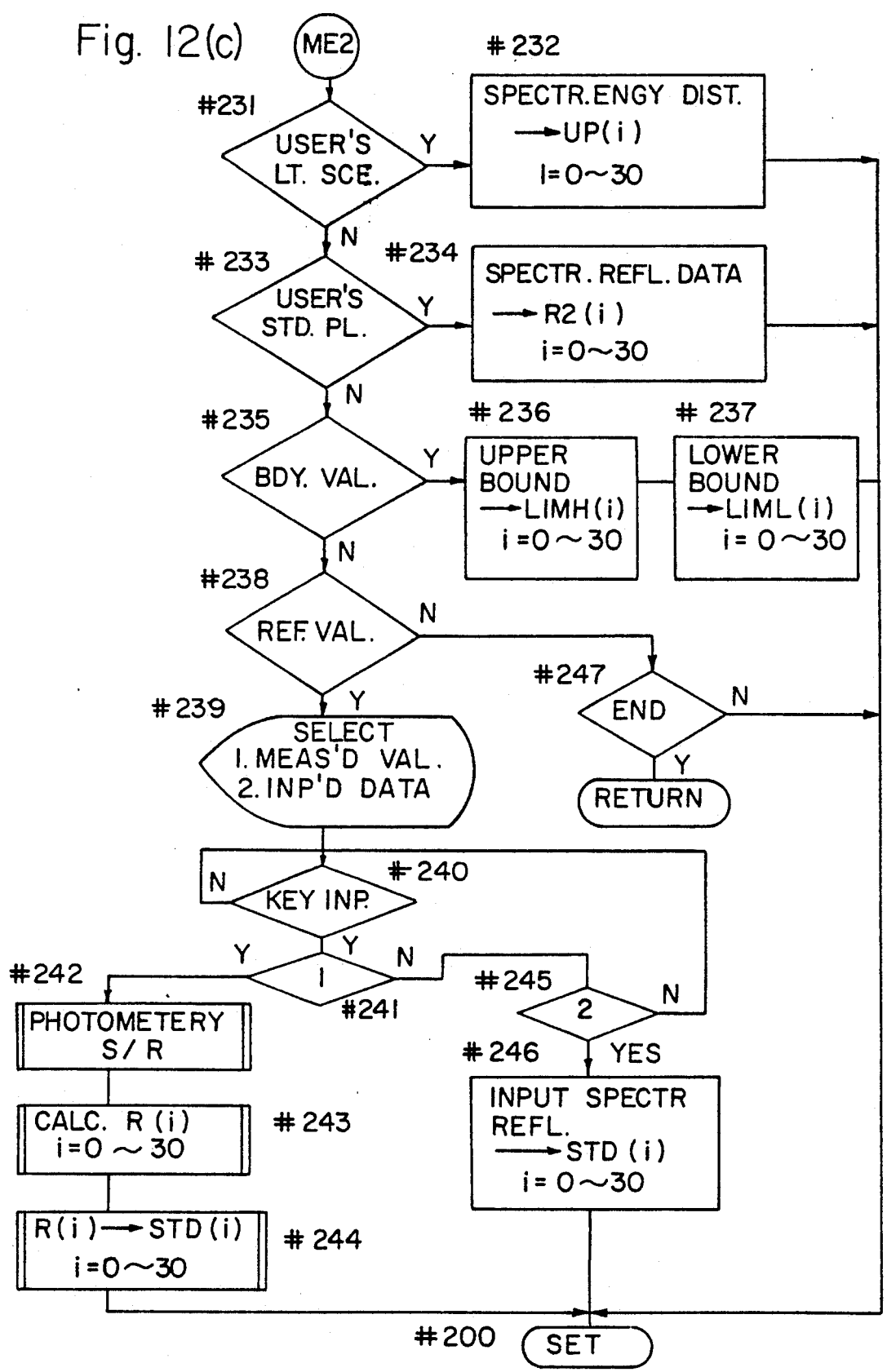

FIGS. 12(a), (b) and (c) are flow charts of the above-described setting subroutine for carrying out the process related to setting. At step #200, an operator selects one of the following nineteen kinds of items of the menu:

1. LIGHT SOURCE; 2. FIELD OF VISION; 3. TRIGGER MODE; 4. TRACE WAVELENGTH; 5. BOUNDARY WARNING; 6. AVERAGE OF NUMBER OF MEASUREMENTS; 7. PRINTOUT MODE; 8. PRINTOUT MENU; 9. DATA OUTPUT MODE; 10. OUTPUT DATA MENU; 11. RS232C MODE; 12. TIMER; 13. CLOCK; 14. USER'S SPECTRAL SENSITIVITY; 5. USER'S LIGHT SOURCE; 16. USER'S STANDARD PLATE; 17. BOUNDARY VALUE; 18. REFERENCE VALUE; and 19. END.

Then, the program proceeds to step #201, at which it is discriminated whether or not the selected item is "LIGHT SOURCE". With the affirmative answer, the program proceeds to step #202, at which the operator is let to select one of five classes of light source D65, A, B, C, and USER for the color value calculation. After that, the program returns to step #200. If the selected item is not "LIGHT SOURCE", the program proceeds to step #203, at which it is discriminated whether or not the selected item is "FIELD OF VISION". If it is "FIELD OF VISION", the operator is let to select either 2° or 10° of field of vision, and then, the program returns to step #200. If the item selected is not "FIELD OF VISION", the program proceeds to step #205, at which it is discriminated whether or not the selected item is "TRIGGER MODE", which is a mode for deciding how to start the measurement. If it is, at step #206, the operator selects one of the following four items: "manual", "single external trigger", "continuous external trigger" and "timer". Then, the program returns to step #200. If not "TRIGGER MODE", the program proceeds to step #207, at which it is discriminated whether or not the selected item is "TRACE WAVELENGTH". If it is "TRACE WAVELENGTH", the program proceeds to step #208, at which the operator is let to select a wavelength for which to indicate the change with time in the spectral reflectance on the graph. After that, the program returns to step #200. Unless it is "TRACE WAVELENGTH", the program proceeds to step #209, at which it is discriminated whether or not the selected item is "BOUNDARY WARNING". When it is "BOUNDARY WARNING", the program proceeds to step #210, at which the operator is let to set whether or not to carry out the warning in case that the difference between a reference value and a measured value exceeds the boundary value. Thereafter the program returns to step #200. If the item selected is not "BOUNDARY WARNING", the program proceeds to step #211, at which it is discriminated whether or not the selected item is "AVERAGE OF NUMBER OF MEASUREMENTS". When it is so, the program proceeds to step #212, at which the operator is let to set the number of times of measurements for obtaining an average of the measured values. Thereafter the program returns to step #200. If it is not "AVERAGE OF NUMBER OF MEASUREMENTS", the program proceeds to step #213, at which it is discriminated whether or not the selected item is "PRINTOUT MODE". If it is, the operator selects either "AUTO" for automatic printout of the measured data at each measurement or "MANUAL" for printout only when the key "PRINT" is pushed down. Then, the program returns to step #200. If it is not "PRINTOUT MODE", the program proceeds to step #215, at which it is discriminated whether or not the selected item is "PRINTOUT MENU". If it is, the program proceeds to step #216, where the operator is let to decide which items of data on the menu such as spectral data, measured color value, etc.. to print out. Thereafter, the program returns to step #200. If it is not "PRINTOUT MENU", the program proceeds to step #217, at which it is discriminated whether or not the selected item is "DATA OUTPUT MODE". If it is, the program proceeds to step #218, at which the operator is let to select either "AUTO" for automatic output of the measured data to the external I/O port 10 at each measurement or "MANUAL" for output carried out only when "DOUT" key is pushed. After that, the program returns to step #200. If the item selected is not "DATA OUTPUT MODE", the program proceeds to step #219, at which it is discriminated whether or not the selected item is "OUTPUT DATA MENU". If it is, the program proceeds to step #220, at which the operator is let to select one or more of the various measured data to be outputted to the external I/O port 10. Then the program returns to step #200. If the item selected is not "OUTPUT DATA MENU", the program proceeds to step #221, at which it is discriminated whether or not the selected item is "RS232C MODE". If it is, the program proceeds to step #222, at which various modes such external I/O port, are set by the operator. Thereafter, the program returns to step #200. If the item selected is not "RS232C MODE", the program proceeds to step #223, at which it is discriminated whether or not the selected item is "TIMER". If it is, the program proceeds to step #224, at which the operator is made to set various data. Such data may be as follows: the starting time Ts of the timer for counting the interval of measurement, the time length Ti of each interval, the ending time Te of the measurement, the number Ne of times of the measurement to be effected, and/or the selection whether to end the measurement when the ending time Te comes or to end the measurement when the set number Ne of measurements have been effected. Then the program returns to step #200. If the item selected is not "TIMER", the program proceeds to step #225, at which it is discriminated whether or not the selected item is "CLOCK". If it is, the program proceeds to step #226, the present hour is set in the real time clock 17 by the operator. Thereafter, the program returns to step #200. If the item selected is not "CLOCK", the program proceeds to step #227, at which it is discriminated whether or not the selected item is "USER'S SPECTRAL SENSITIVITY". If it is, the program proceeds to step #228, at which user's spectral sensitivity is inputted.

Figure 24:
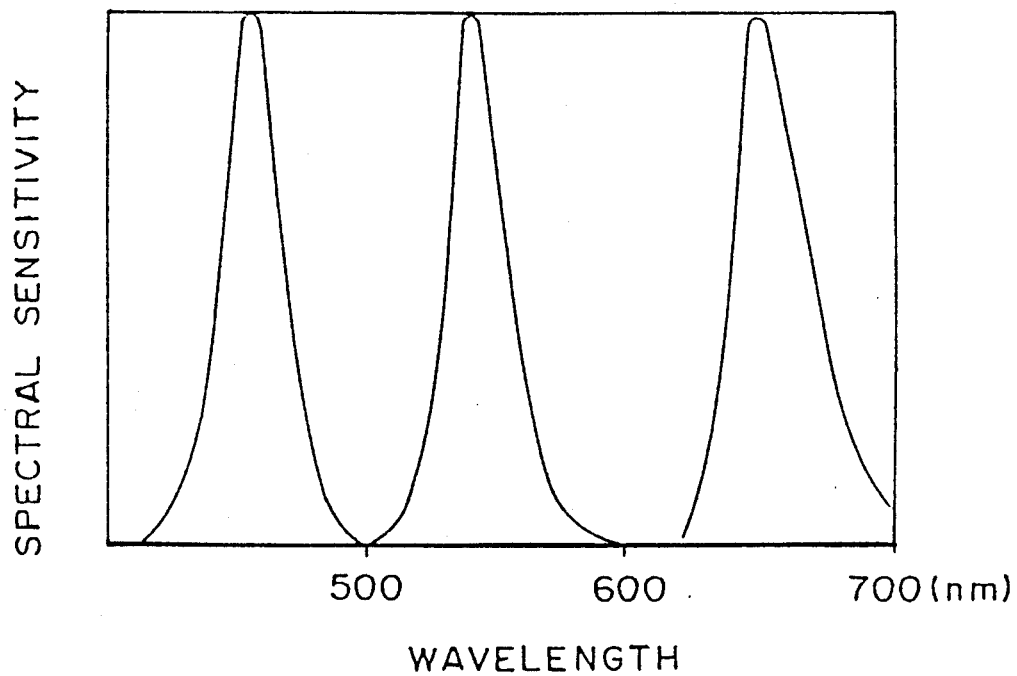
FIG. 24 is a diagram showing spectral sensitivity for measuring color density of a photograph usable in said embodiment.

Now, the meaning of the user's spectral sensitivity is described. Generally, when color calculation is carried out, tristimulus values $\bar{x}\lambda$, $\bar{y}\lambda$, $\bar{z}\lambda$ in CIE colorimetric system are used, although when color density in a photograph is measured, color calculation is carried out by performing the trichromatic analysis using such spectral sensitivity as shown in FIG. 24. Other spectral sensitivity values specialized for individual use are also used. Therefore, it is very useful if arbitrary spectral sensitivity other than the tristimulus values $\bar{x}\lambda$, $\bar{y}\lambda$, $\bar{z}\lambda$ can be used. In this embodiment, the tristimulus values $\bar{x}\lambda$, $\bar{y}\lambda$, $\bar{z}\lambda$ are stored in ROM 7 for a standard use and used for the color calculation. In addition to the data, it is possible for the operator to input arbitrary spectral sensitivity (hereinafter it is referred to as users' spectral sensitivity), which is to be stored in RAM 8. So, it is possible to calculate the sum of each product of the user's spectral sensitivity, the spectral reflectance of the test piece and the spectral energy distribution of the light source and to display the so calculated values. Three kinds of spectral sensitivity can be inputted as users' spectral sensitivity for the convenience of trichromatic resolution. At steps #228 through #230 the three kinds of users' spectral sensitivity are inputted and stored in the respective memories US1(i), US2(i) and US3(i) (i=0~30), thereafter the program returns to step #200. If the item selected is not "USER'S SPECTRAL SENSITIVITY", the program proceeds to step #231, at which it is discriminated whether or not the selected item is "USER'S LIGHT SOURCE". If it is so, the program proceeds to step #232, at which the spectral energy distribution data of the user's light source is inputted.

Now, the meaning of the user's light source is described. In the color calculation of an object, light sources such as D65, A, B, C are generally used as a standard light source. The spectral energy distribution data of such light sources are stored in ROM 7 in this embodiment. If the operator can define other light source of arbitrary spectral energy distribution than those standard ones and calculate color values of the object under the light source, it is very convenient for evaluation of color rendering properties or a light source effect on the apparent of the object color. In this embodiment, it is possible for the operator to input arbitrary spectral energy distribution for a light source (hereafter it is referred to as user's light source). The light source data is stored in RAM 8 and is used for the color evaluation.

The spectral energy distribution of the user's light source is inputted and stored in a memory UP(i) (i=0~30) at step #232, then the program returns to step #200.

If the item selected is not "USER'S LIGHT SOURCE", the program proceeds to step #233, at which it is discriminated whether or not the selected item is "USER'S STANDARD PLATE". With the answer in the affirmative, the program proceeds to step #234, at which spectral reflectance data of a user's standard plate are inputted and stored in memory R2(i) (i=1~30). Thereafter the program returns to step #200. Though detail description of the user's standard plate will be performed later in relation to the calibration subroutine, to put it briefly, "USER'S STANDARD PLATE" means a standard plate which the operator prepares in advance by measuring reflectance data using a spectrometer, etc.. and with which reflectance calibration is carried out in this embodiment. If the item is not "USER'S STANDARD PLATE", the program proceeds to step #235, at which it is discriminated whether or not the selected item is "BOUNDARY VALUE". If it is so the program proceeds to step #236. In this embodiment, the upper bound and lower bound values of the spectral reflectance can be determined for each wavelength. When measured spectral reflectance value is outside of the bounds, warning is displayed. Data of the both bounds can be displayed on the spectral graph indicating the measured spectral reflectance values, overlapping therewith, so that the relation between the measured values and the bound values may be seen at a glance. At step #236, the upper value is inputted and stored in LIMH(i) (i=0~30). At step #237 the lower value is inputted and stored in LIML(i) (i=0~30), and then the program returns to step #200. If the item selected is not "BOUNDARY VALUE", the program proceeds to step #238, at which it is discriminated whether or not the selected item is "REFERENCE VALUE". If the answer is yes, the program proceeds to step #239. At this step, it is determined which will be considered as a reference value, measured value obtained by the measurement or value of the spectral reflectance inputted from the keyboard. Selection items are displayed at step #239 before key input is awaited at step #240 If there is a key input, the program proceeds to step #241, at which it is discriminated whether or not the key is "1". If it is "1", which is a mode for letting the measured value be a reference value, the program proceeds to step #242, at which above mentioned photometry subroutine is carried out, and at step #243 the spectral reflectance R(i) (i=0~30) is calculated, and then, at step #244 the spectral reflectance R(i) gets stored in a reference value memory STD(i) (i=0~30). Thereafter, the program returns to step #200. If the key is judged not to be "1" at step #241, the program proceeds to step #245, at which it is discriminated whether or not the key is "2". If it is not "2" at step #245, the program returns to step #240 at which a key input is awaited. If it is discriminated, at step 245, that the key is "2", the program proceeds to step #246 because the key "2" is for a mode of letting the input data from the numerical keys be reference value data. At step #246, spectral reflectance data as a reference value are inputted by the numerical keys and stored in STD(i) (i=0~30). Then the program returns to step #200. If the item selected is not "REFERENCE VALUE", the program proceeds to step #247, at which it is discriminated whether or not the item is "END". If it is "END", the setting subroutine is finished and the program returns. If the item is not "END", the program returns to step #200. That is all for the description of the setting subroutine.

Figure 13A:
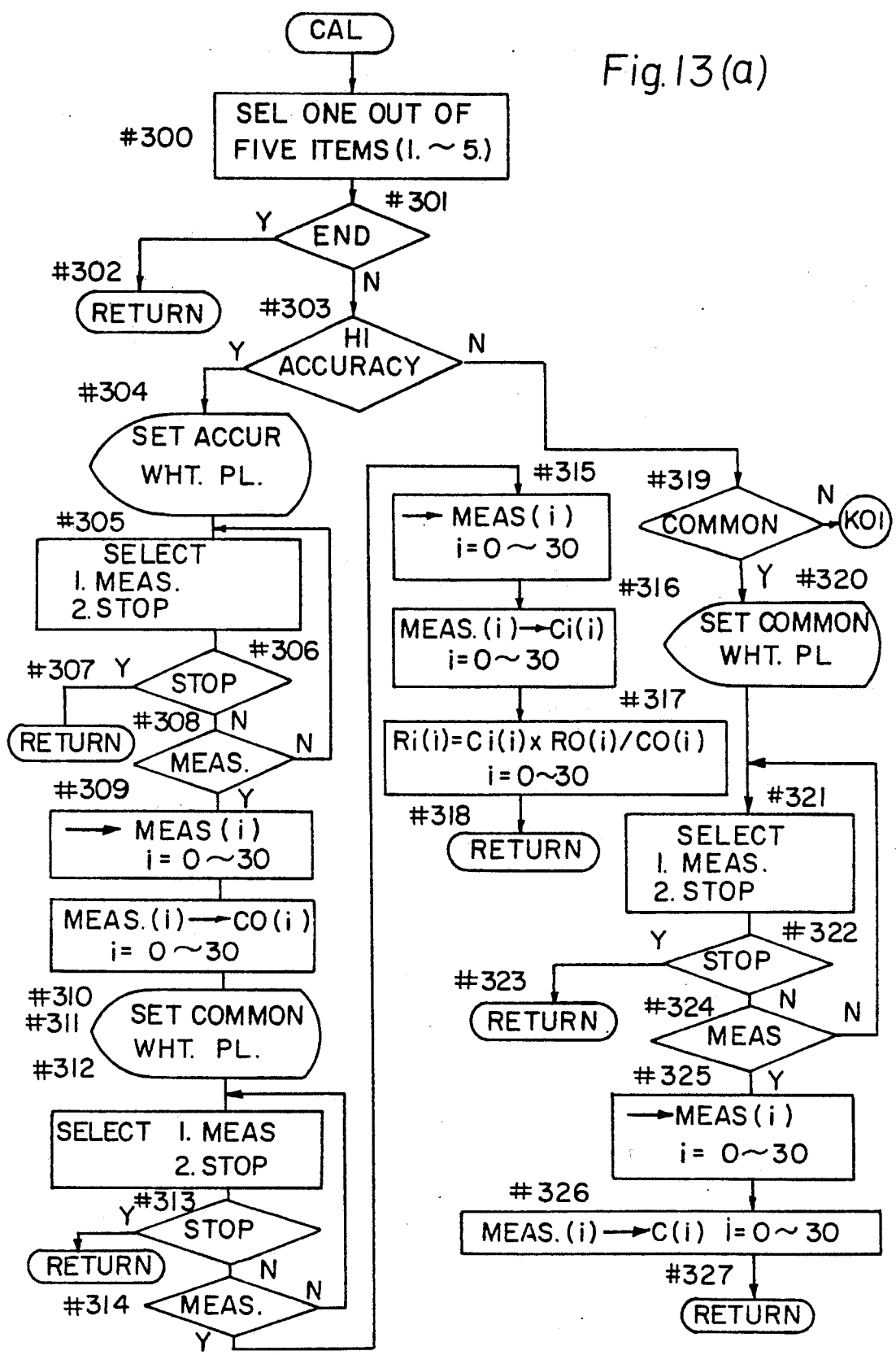
FIGS. 13(a) and (b) are flow charts of a calibration subroutine in said embodiment.

Hereafter, the calibration subroutine will be described. The calibration subroutine is for the process of calibrating measured reflectance value using a sample whose spectral reflectance is already known. The flow chart of the calibration subroutine is shown in FIG. 13. At step #300, the operator is let to select one of five items of the menu. Referring now to those items, "1. STANDARD WHITE PLATE WITH HIGH ACCURACY" is for calibration using an accurate standard white plate which changes very little in spectral reflectance with time though it is expensive. "2. COMMON STANDARD WHITE PLATE" is for calibration using a common standard white plate which changes in spectral reflectance with time more than the accurate standard white plate though it is cheap. "3. USER'S STANDARD PLATE" is for calibration using a sample other than the attached white plate, the spectral reflectance of which sample has been measured by the operator with use of a spectrometer, etc. "4. CALIBRATION MODE" is for selection of the calibration mode. "5. END" is for bringing the calibration subroutine to an end.

At step #301 it is discriminated whether or not the item is "END". If it is "END", the program proceeds to step #302, at which the calibration subroutine is brought to =an end and the program returns. If it is not "END", the program proceeds to step #303, at which it is discriminated whether or not the item is "STANDARD WHITE PLATE WITH HIGH ACCURACY". If the answer is yes, the program proceeds to step #304, at which there is displayed a massage to the effect that the accurate standard white plate is to be set as a sample. Then, at step #305, the operator is let to select one of two items, "MEASURE" and "STOP". At step #306 it is discriminated whether or not the item is "STOP". If it is "STOP", the program proceeds to step #307, at which the calibration subroutine is brought to an end and the program returns. If the item is not "STOP", the program proceeds to step #308, at which it is discriminated whether or not the item is "MEASURE". If it is not "MEASURE", the program returns to step #305, and if it is "MEASURE", the program proceeds to step #309, at which the above described photometry subroutine is carried out. Measured value MEAS(i) is stored in C0(i) (i=0~30) at step #310. Thereafter, at step #311, a message is displayed to the effect that the common standard white plate is to be set as a sample. At step #312, the operator is let to select one of two items, "MEASURE" or "STOP", and then, at step #313 it is discriminated whether or not the item is "STOP". If the item selected is "STOP", the calibration subroutine is brought to an end and the program returns. If it is not "STOP", the program proceeds to step #314, at which it is discriminated whether or not the item is "MEASURE". If it is not "MEASURE", the program returns to step #312. If it is "MEASURE", the program proceeds to step #315, where the photometry subroutine is carried out. At step #316, measured value MEAS(i) is stored in C1(i) (i=0~30). Thereafter, at step #317, the spectral reflectance of the common standard white plate is calculated using the equation (18) below and stored in R1(i) (i=0~30). Then the program proceeds to step #318, at which the calibration subroutine is brought to an end and the program returns.

$$R1(i) = C1(i) \times R0(i)/C0(i) \quad (18)$$

In the above equation, R0(i) indicates spectral reflectance data of the accurate standard white plate, which data are stored in ROM 7 in advance. To sum up, at steps #304 through 310, measured value is calibrated by the accurate standard white plate. At steps #311 through 317, the spectral reflectance of the common standard white plate is measured and stored in the memory.

Unless the item is "STANDARD WHITE PLATE WITH HIGH ACCURACY" at step #303, the program proceeds to step #319, at which it is checked if the item is "COMMON STANDARD WHITE PLATE". If so, the program proceeds to step #320, at which a message is displayed to the effect that the common standard white plate is to be set as a sample. Then, at step #321, the operator is let to select either "MEASURE" OR "STOP". At step #322, it is discriminated whether or not the item selected is "STOP". If it is "STOP", the program proceeds to step #323, at which the calibration subroutine is brought to an end and the program returns. If not "STOP", the program proceeds to step #324, at which it is discriminated whether or not the item selected is "MEASURE". If not "MEASURE", the program returns to step #321, and if "MEASURE", the program proceeds to step #325, where the photometry subroutine is carried out. After the measured value MEAS(i) is stored in C1(i) at step #326, the program proceeds to step #327, at which the calibration subroutine is brought to an end and the program returns.

As was described above, according to the present embodiment, absolute value of the spectral reflectance is calibrated by either the common standard white plate or the accurate standard white plate with high accuracy. The common standard white plate which is cheap is used for the daily calibration and the standard white plate with high accuracy which is expensive is used every few months to correct a change of the spectral reflectance of the common standard white plate with time. The spectral reflectance of the common standard white plate, measured by use of the standard white plate with high accuracy, is stored in the memory. The accurate standard white plate is not used frequently. In addition to this condition of use, if it is kept in a proper place, a change with time caused by dirt or ultraviolet rays can be prevented. And also, it is comparatively easy to maintain the common standard white plate because the change thereof with time is corrected only once in every few months. This brings a measurement system which is cheap, effective and very accurate.

Figure 13B:
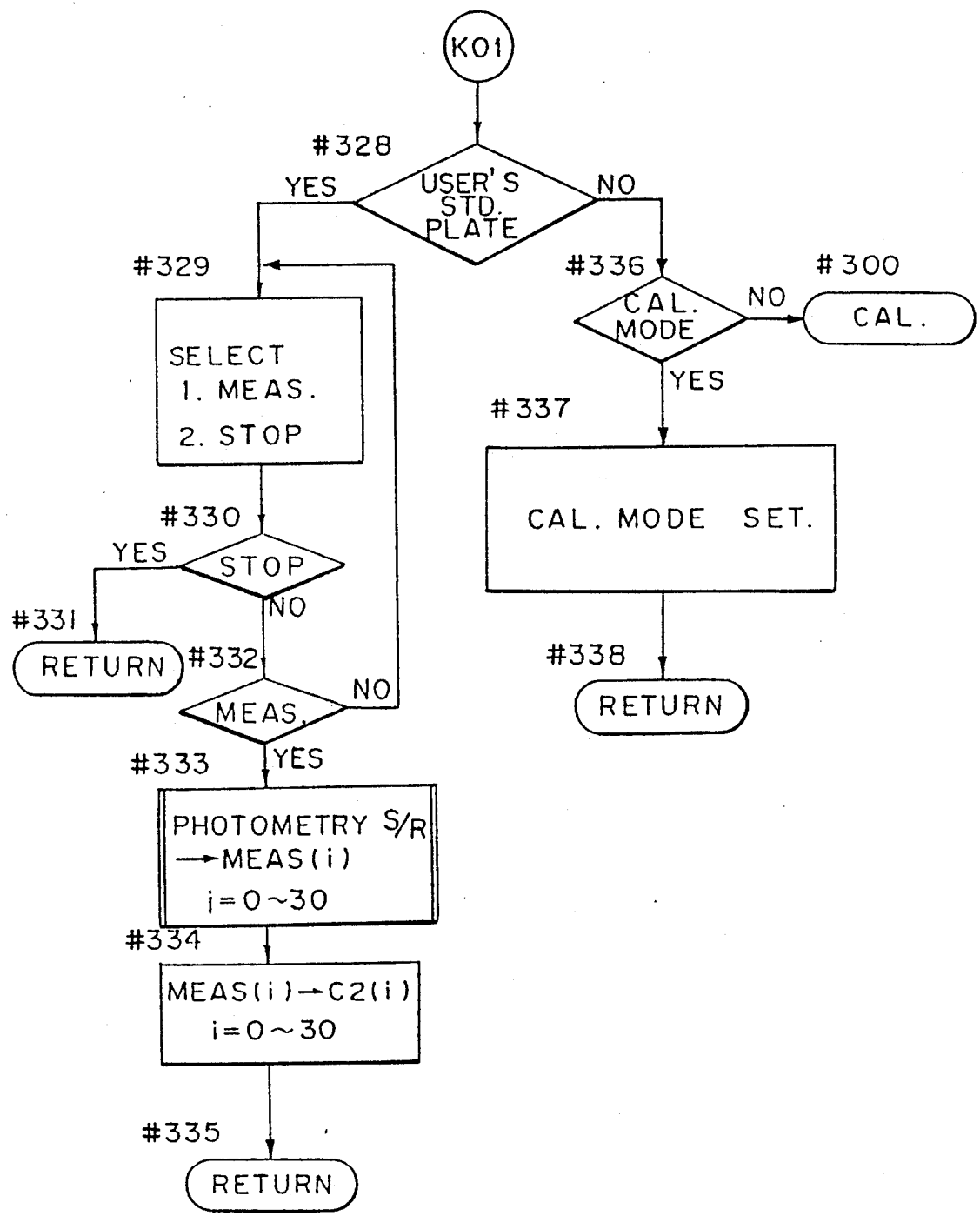

Unless the item selected is judged to be "COMMON STANDARD WHITE PLATE" at step #319, the program proceeds to step #328 of FIG. 13(b), at which it is discriminated whether or not the item selected is "USER'S STANDARD PLATE". With the answer in the affirmative, the program proceeds to step #329, at which either "MEASURE" or "STOP" is selected by the operator. When the discrimination result at step #330 is "STOP", the program proceeds to step #331, where the calibration subroutine is brought to an end and the program returns. If not "STOP", the program proceeds to step #332, at which it is discriminated whether or not the item selected is "MEASURE". When it is not "MEASURE", the program returns to step #329, and when it is "MEASURE", the photometry subroutine is carried out at step #333. The measured value MEAS(i) is stored in C2(i) (i=0~30) at step #334 and then, the program returns. Unless the item selected is "USER'S STANDARD PLATE" at step #328, the program proceeds to step #336, at which it is discriminated whether or not the item selected is "CALIBRATION MODE". If it is not "CALIBRATION MODE", the program returns to step #300 and if it is "CALIBRATION MODE", the program proceeds to step #337, at which the operator is let to select one of two kinds of calibration modes, that is, calibration by the standard white plate or by the user's standard plate. Then, the program returns. If the mode of calibration by the standard white plate is selected, the value C1(i) which has been obtained through the calibration carried out at steps #320 through #326 using the common standard white plate, and the spectral reflectance R1(i), of the common standard white plate, measured at steps #311 through #317 are used in calculating the spectral reflectance of the test piece. On the other hand, if the mode of calibration by the user's standard plate is selected, the value C2(i) calculated through the calibration carried out at steps #329 through #334 using the user's standard plate and the spectral reflectance data R2(i), of the user's standard plate, inputted at step #234 in the setting subroutine are used in calculating the spectral reflectance of the test piece. That is all for the description on the calibration subroutine.

Figure 14A:
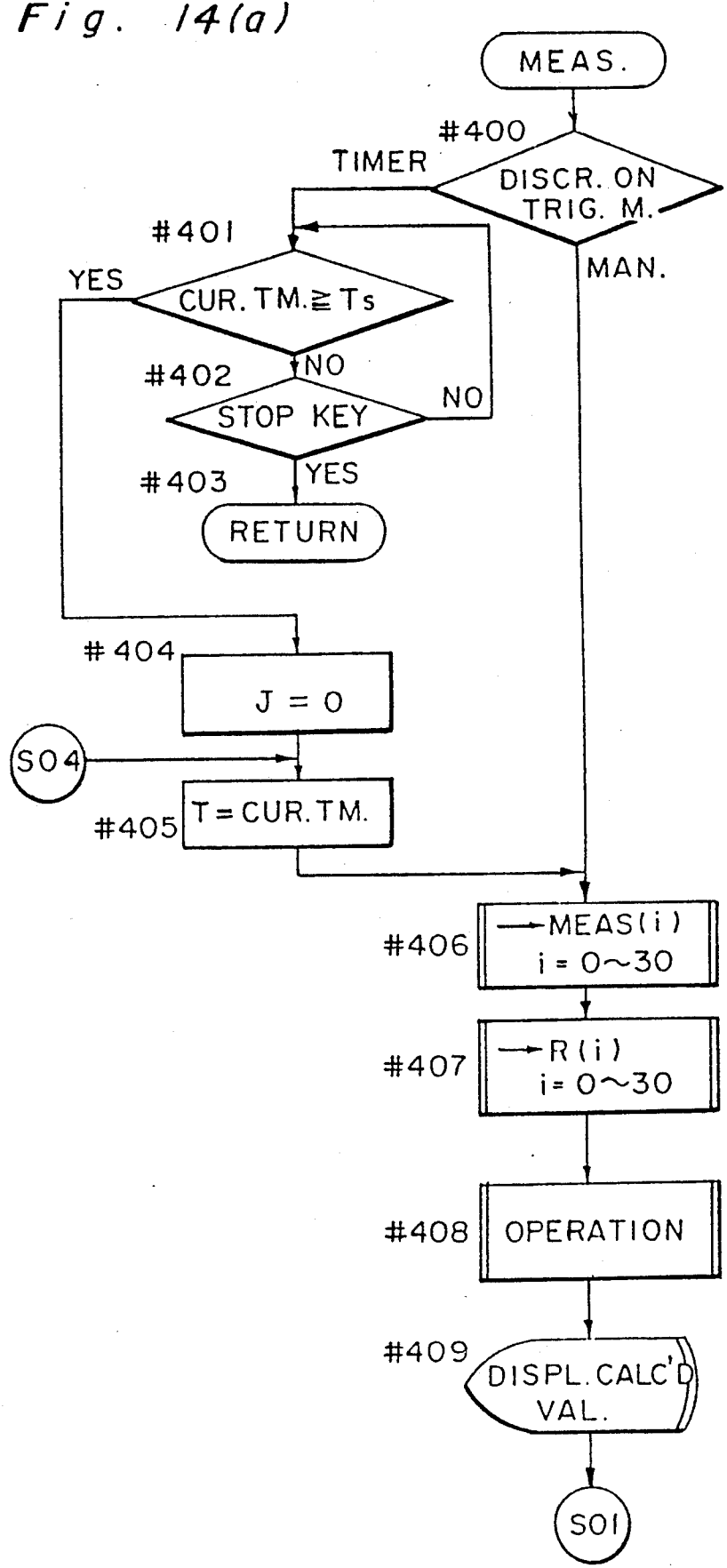
FIGS. 14(a) through 14(c) are flow charts of a measurement subroutine in said embodiment.
Figure 14B:
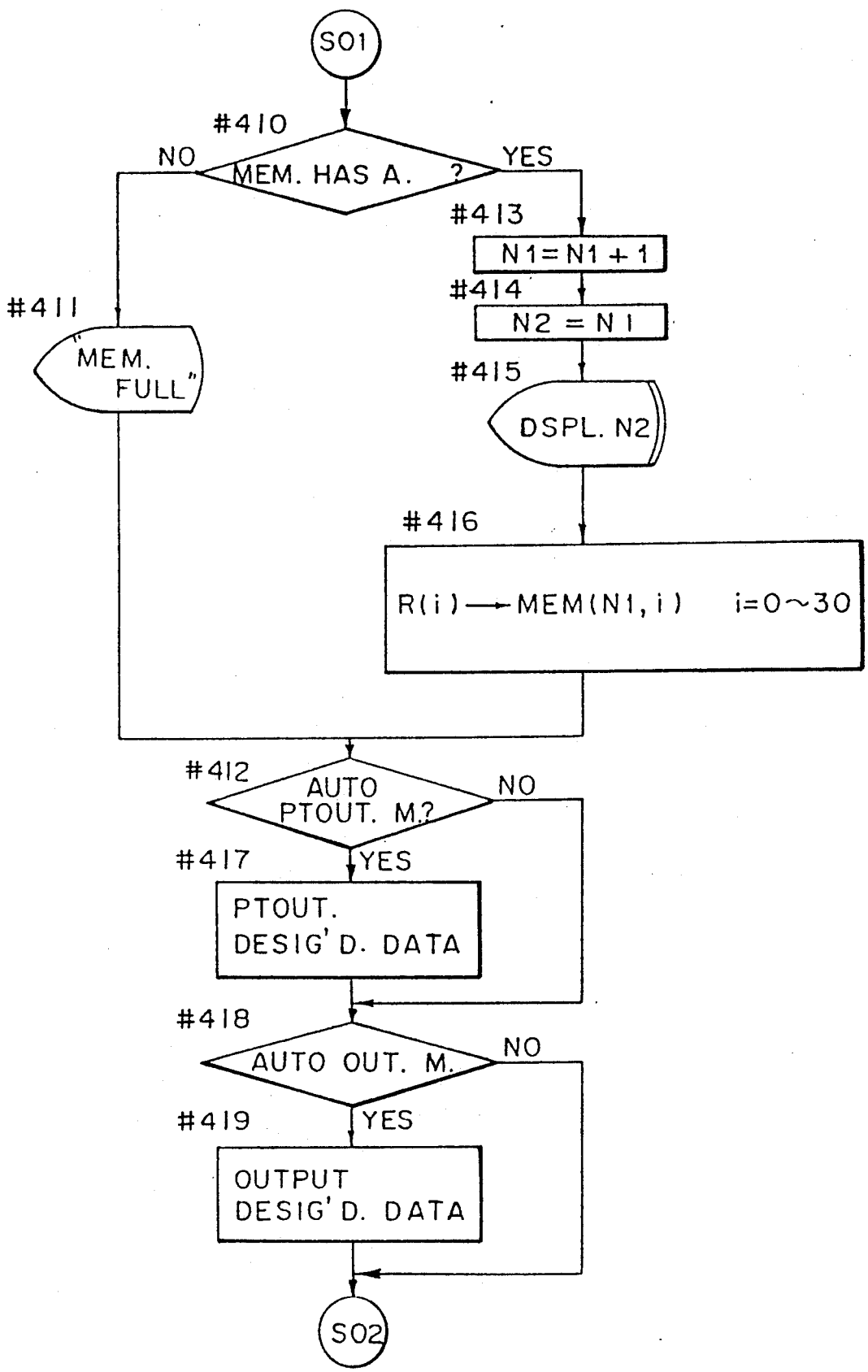
Figure 14C:
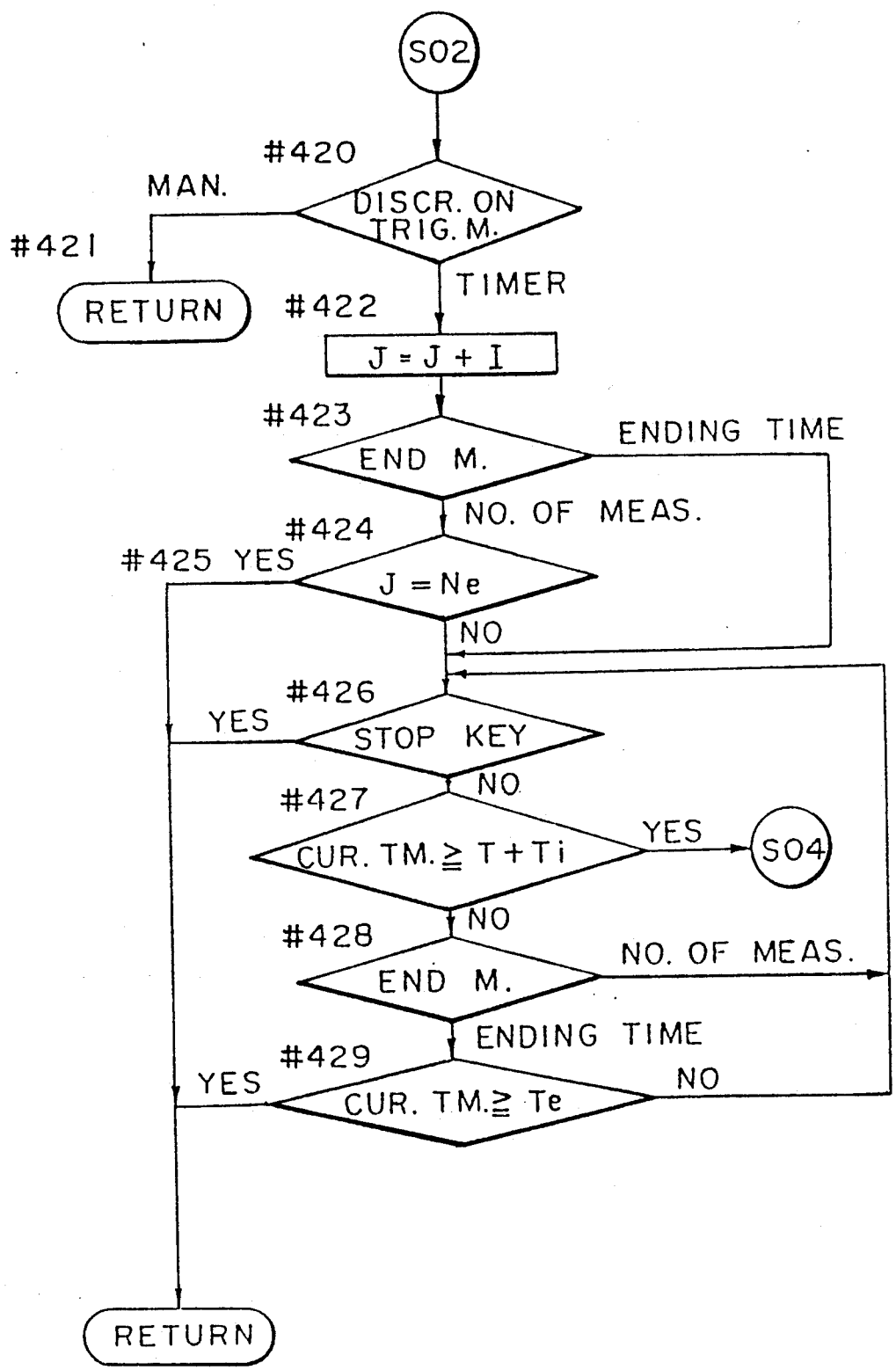

Hereafter, the measurement subroutine will be described. FIG. 14 shows a flow chart of the measurement subroutine. First, if it is judged that "MANUAL" has been selected for the trigger mode at step #400, the program proceeds to step #406, and if "TIMER" is selected for the trigger mode, the program proceeds to step #401. At step #401, data of the real-time clock 17 are inputted and it is discriminated whether or not the current hour has passed the measurement starting time Ts set at step #224 in the aforementioned setting subroutine. With the answer in the negative, the program proceeds to step #402, at which it is checked whether or not the "STOP" key is pushed. If it is judged that the key has been pushed, the program proceeds to step #403, at which the measurement subroutine ends and the program returns. If the "STOP" key is not pushed, the program returns to step #401. If it is judged that the current time has passed the measurement starting time Ts at step #401, the number J of measurements is cleared to zero at step #404. Then, at step #405, the current time is put into a register T, and then, the program proceeds to step #406, at which the photometry subroutine is carried out. At step #407, the reflectance calculation subroutine is carried out. Calculation results are stored in R(i). A full detail of the reflectance calculation subroutine will be given later. At step #408, the operation subroutine is carried out for effecting an operation to obtain color value or to discriminate on bounds. At step #409, a calculated value display subroutine is carried out for displaying measured values or calculated values. At step #410 it is discriminated whether or not there is area in the memory used for measured values. If there is no area, the program proceeds to step #411, at which warning is given to tell that there is no area in the memory for measured values and that therefore the measured value obtained this time will not be stored therein. Thereafter the program proceeds to step #412. If there is area, the program proceeds to step #413, where "1" is added to the final measured data number N1. At step #414, N1 is substituted into N2 indicating data No. of the data on display. After the value of N2 is displayed at step #415, the program proceeds to step #416, at which the calculated spectral reflectance value ((i) (i= ~30) is stored in the N1th memory for the measured value. Then, the program proceeds to step #412, at which it is discriminated whether the printout mode is "AUTO". If it is "AUTO", the program proceeds to step #417, at which the printer 16 prints the item selected at step #216 of the setting subroutine. Thereafter, the program proceeds to step #418. Unless the printout mode is "AUTO", the program proceeds to step #418, at which it is discriminated whether the data output mode is "AUTO". With the answer in the affirmative, the program proceeds to step #419, at which one or more output data items selected at step #220 of the setting subroutine are outputted to the external I/O port 10, before the program proceeds to step #420. On the other hand, with the negative answer, the program proceeds to step #420. If it is judged at step #420 that the trigger mode is "MANUAL", the measurement subroutine is brought to an end at step #421 and the program returns. If the trigger mode is "TIMER", the program proceeds to step #422, at which the number J of measurements is increased by one. Thereafter, at step #423 it is discriminated whether to end the measurement when the set number Ne of measurements have been effected or to end it when the ending time Te comes. If it is judged that the program is under the mode of ending defined by the number of measurements, the program proceeds to step #424, at which it is discriminated whether or not the actual number J of measurements is equal to the number of times Ne of the measurement to be effected which has been set at step #224 of the setting subroutine. If the two values are equal, the program proceeds to step #425, at which the measurement subroutine is brought to an end and the program returns. If the two values are not equal to each other, the program proceeds to step #426. If it is judged at step #423 that the measurement is to end when the set ending time Te comes, the program proceeds to step #426. At step #426, it is discriminated whether or not the "STOP" key has been pushed. If the key has been pushed, the measurement subroutine is brought to an end at step #425 and the program returns. If not, the program proceeds to step #427, at which it is discriminated whether or not the current time has passed the time obtained by adding the time length Ti of the interval set at step #224 of the setting subroutine to the previous measurement time. If the answer is yes, the program returns to step #405 and the measurement process is repeated. If the answer is no, the program proceeds to step #428, at which discrimination of the ending mode is carried out. If the mode of ending defined by the number of times of measurement is detected at step #428, the program returns to step #426 and the discrimination concerning the "STOP" key input and the current time is repeated. If the ending is to be determined by the ending time Te, the program proceeds to step #429, at which it is checked whether the current time has passed the preset ending time Te. If the answer is yes, the program proceeds to step #425, at which the photometry subroutine is brought to an end and the program returns. If the answer is no, the program returns to step #426, and the just mentioned process from step #426 on to step #429 is repeated. That is all for the description on the measurement subroutine.

The reflectance calculation subroutine which was used at step #407 of the measurement subroutine and at step #243 of the setting subroutine will be described hereafter. The reflectance calculation means a calculation for determining the spectral reflectance of the test piece from the spectral reflectance data and the measured value of the standard white plate used for the calibration and the measured value of the test piece.

Figure 15:
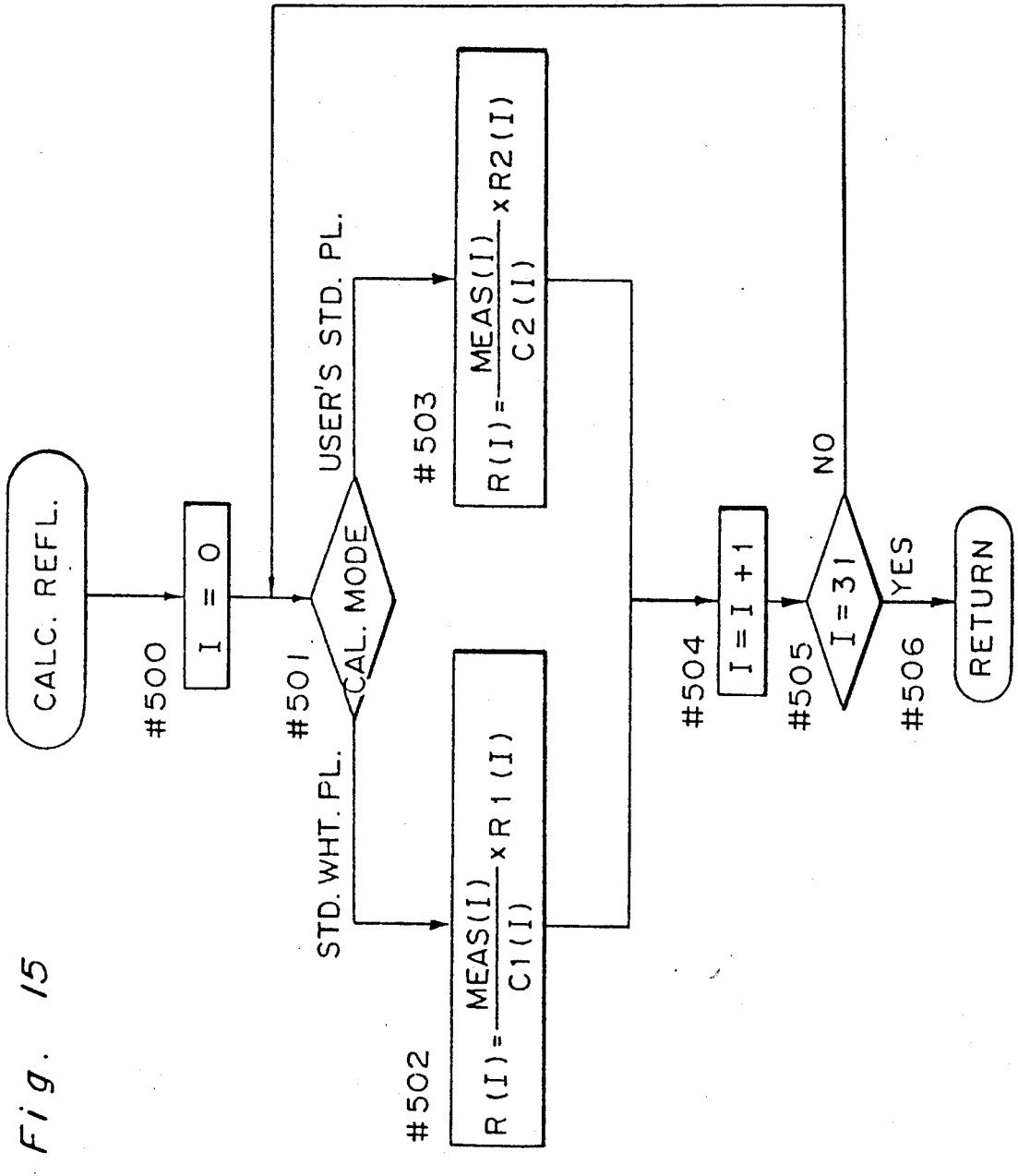
FIG. 15 is a flow chart of a reflectance calculation in said embodiment.

Referring now to FIG. 15 showing a flow chart of the spectral reflectance calculation subroutine, at step #500, the counted value of a counter I for counting wavelength is cleared to zero. At step #501, it is discriminated whether the current calibration mode is "STANDARD WHITE PLATE" or "USER'S STANDARD PLATE". This calibration mode setting has been done at step #337 of the calibration subroutine. If the mode of calibration to be effected using the standard white plate is detected, the following equation (19) is calculated at step #502 to determine the spectral reflectance R(I) of the test piece at the Ith wavelength.

$$R(I) = \frac{MEAS(I)}{C1(I)} \times R1(I) \quad (19)$$

where MEAS(I) is the measured value of the test piece, C1(I) is the measured value, obtained at the calibration subroutine, of the common standard white plate, and R1(I) is the spectral reflectance, obtained in the calibration subroutine, of the common standard white plate. If the mode of calibration using the user's standard plate is detected at step #501, the following equation (20) is calculated at step #503 to obtain the spectral reflectance R(I) of the test piece at the Ith wavelength, and thereafter, the program proceeds to step #504.

$$R(I) = \frac{MEAS(I)}{C2(I)} \times R2(I) \quad (20)$$

At step #504, an increment of "1" is given to the wavelength counter I and then, at step #505 it is checked whether I=31 or not. In this embodiment, reflectances at every pitch of 10 nm in the range of wavelength from 400 to 700 nm are calculated, so that I takes value from 1 to 30. It means that the calculation of the reflectance for each wavelength has been effected when I is judged to be 31. Therefore, when I=31, the reflectance calculation subroutine comes to an end and the program returns. If i≠31, the program returns to step #501 and the above process is repeated till the calculation of the reflectance for every wavelength is effected. That is all for the description on the reflectance calculation subroutine.

Figure 16A:
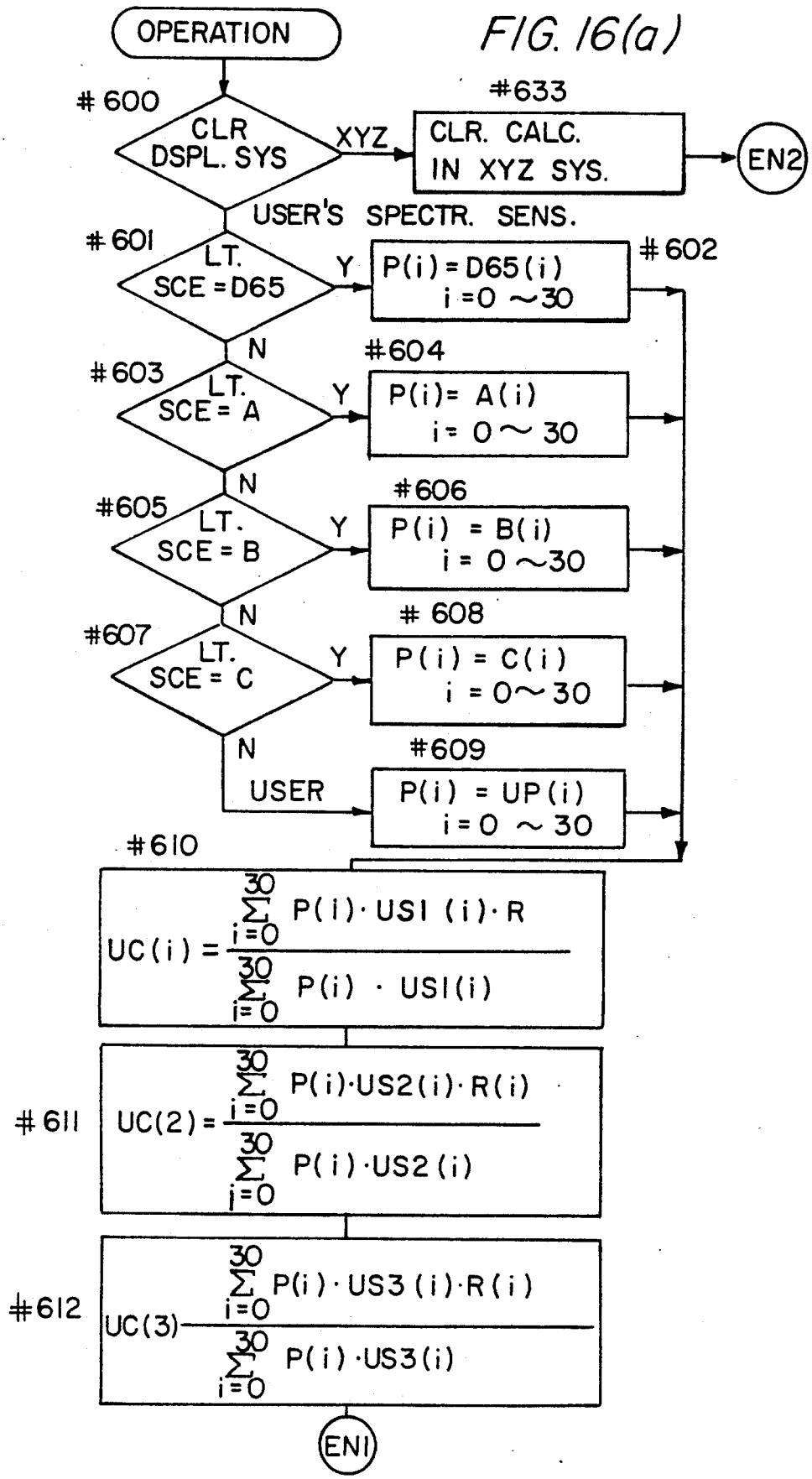
FIGS. 16(a) through 16(c) are flow charts of an operation subroutine in said embodiment.
Figure 16B:
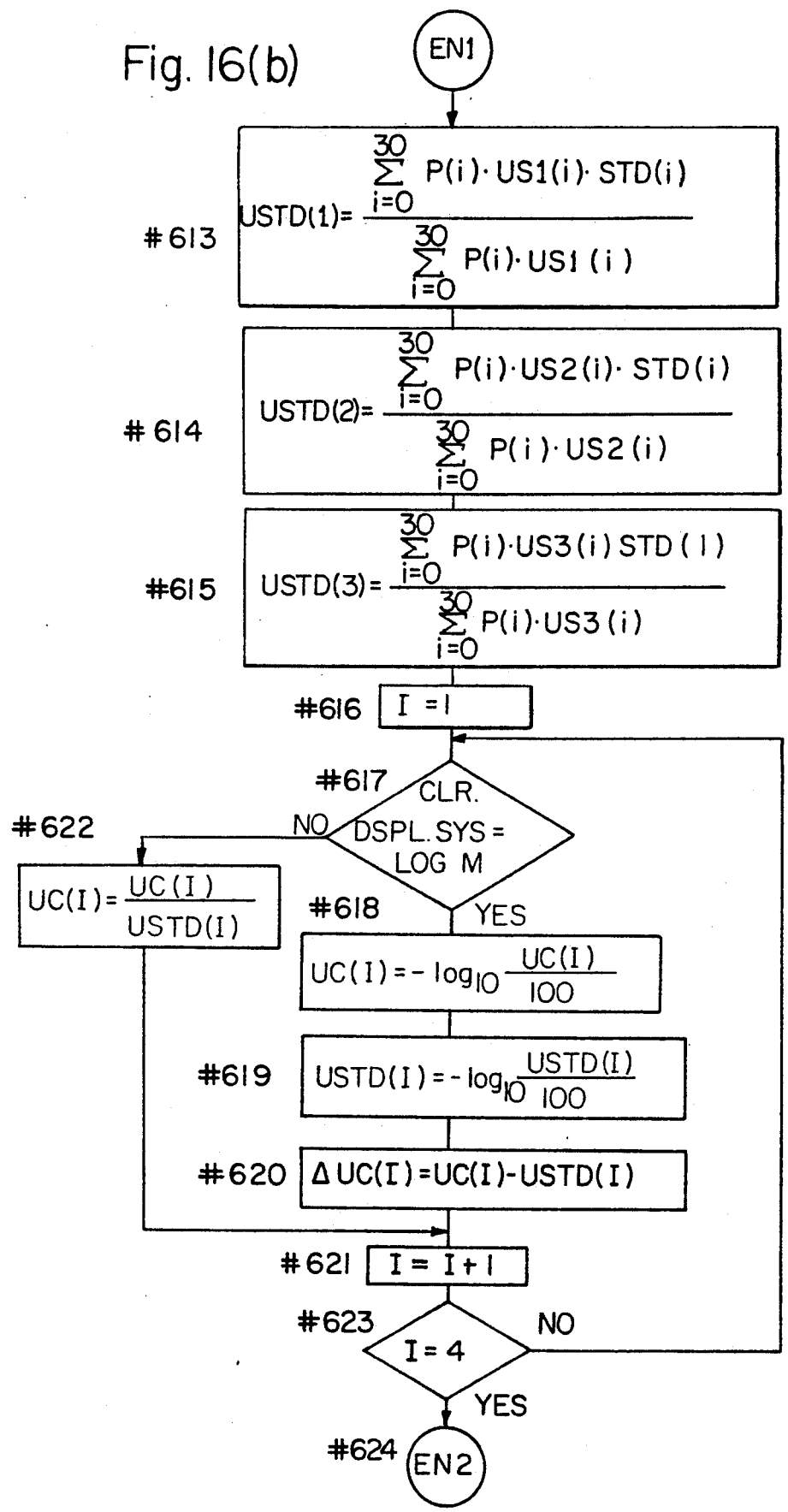
Figure 16C:
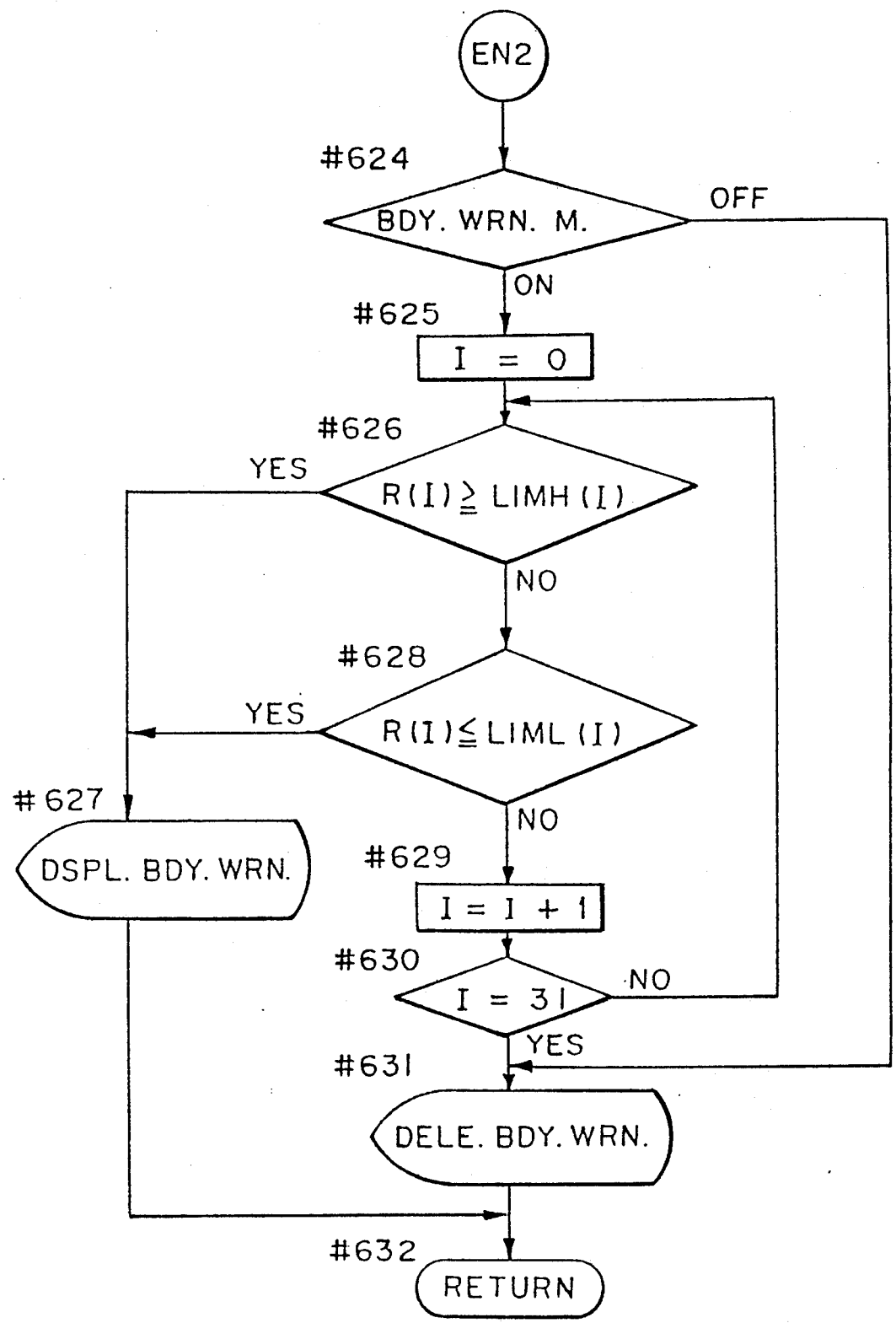

Next, the operation subroutine will be described. This subroutine was used at step #408 of the measurement subroutine. This is a subroutine for effecting various color calculations and discrimination on the bounds on the basis of the spectral reflectance R(i) of the test piece. FIGS. 16(a), (b), and (c) show a flow chart of the operation subroutine. At step #600, it is discriminated whether to display color values in the XYZ colorimetric system or to display them in the user's spectral sensitivity system. When the user's spectral sensitivity color display system is detected, the program proceeds to step #601. At steps #601 through #609 it is checked what kind of light source has been selected at step #202 of the setting subroutine and data on the spectral energy distribution of the selected light source is stored in P(i). If the selected light source is any one of the light sources D65, A, B and C, their respective spectral energy distribution data D65(i), A(i), B(i) or C(i) (i=0~30) stored in ROM 7 in advance are put in P(i). If the selected light source is a user's light source, spectral energy distribution data UP(i), set at step #232 of the setting subroutine, of the user's light source is stored in P(i). At step #610 the value obtained by dividing the sum of the products of the spectral energy distribution P(i) of the light source, the first user's spectral sensitivity US1(i) and the spectral reflectance R(i) of the test piece within the measurement wavelength region by the sum of the products of P(i) and US1(i) within the measurement wavelength region, as shown in the flow chart, is substituted into the first user's color data UC(1). Similar calculation is carried out with the second and third user's spectral sensitivities US2(i) and US3(i) at steps #611 and #612 and the calculated values are substituted into the respective second and third user's color data UC(2) and UC(3). Thereafter, at steps #613, #614 and #615, color calculation related to user's spectral sensitivities US1(i), US2(i) and US3(i) is carried out with the spectral reflectance data STD(i) as a reference value which has been set at steps following step #239 of the setting subroutine, and each of the calculated values is stored in USTD(1), USTD(2) and USTD(3), respectively. Next, at step #616, the number I of the spectral sensitivity is set to be "1". At step #617 it is discriminated whether the color display system is under the logarithmic mode of the user's spectral sensitivity or under the percentage mode thereof. If it is under the logarithmic mode, the value of UC(I) per cent is changed to absorbance value at step #618 and similarly the value of USTD(I) per cent is changed to absorbance value at step #619. Generally, spectral sensitivity for measurement of color density of a colored picture is defined as a user's spectral sensitivity and color evaluation is effected using logarithmic value. Therefore, the function of calculating the absorbance, which is a logarithmic value, is very useful. At step #620, difference between a measured value and the reference value is calculated and stored in ΔUS(I). If the color display system is not under the logarithmic mode but under the percentage mode, the program proceeds to step #622, at which proportion of UC(I) to USTD(I) is calculated and stored in ΔUS(I). Thereafter, at step #621 increment of "1" is given to I. When discrimination on the value of I at step #623 says that the value of I is not 4, the program returns to step #617 and calculation with I=1,2,3 is carried out and the program proceeds to step #624. When the color display system is under "XYZ" mode at step #600, color is evaluated either in the common XYZ colorimetric system or $X_{10}Y_{10}Z_{10}$ colorimetric system on the basis of the tristimulus value data (already stored in ROM 7) of the visual field (2° or 10°) selected in the setting subroutine, the spectral energy distribution data of the selected light source and the spectral reflectance data of the test piece at step #633. At next step #624, it is checked whether or not the mode of warning of bounds is in an ON-state or OFF-state. If it is in an ON-state, this step is followed by step #625, at which the wavelength number I is cleared to zero. At step #626, it is discriminated whether or not the spectral reflectance R(I) of the test piece at the Ith wavelength is above the upper bound LIMH(I) of the spectral reflectance, set at step #236 of the setting subroutine, at the same wavelength. When R(I) is above LIMH(I), the warning is displayed at step #627 to the effect that the spectral reflectance of the test piece is outside the tolerance, and the program returns. 5 When it is judged at step #626 that R(I) is smaller than LIMH(I), the program proceeds to step #628, at which it is discriminated whether the spectral reflectance R(I) of the test piece at the Ith wavelength is below the lower bound value LIML(I) of the spectral reflectance, set at step #237 of the setting subroutine, at the Ith wavelength region. If R(I) is below LIML(I), the program proceeds to step #627, at which the warning is displayed to the effect that the spectral reflectance of the test piece is outside the tolerance and the program returns. When it is judged that R(I) is greater than LIML(I) at step #628, increment of "1" is given to the wavelength number I at step #629. Subsequently, at step #630 it is judged whether I=31 or not so as to discriminate whether or not the above procedure has been completed with all the wavelengths. With the answer in the negative, the program returns to step #626 and the process of discriminating on the bounds is repeated. If the answer is yes, which means that the spectral reflectances of the test piece in every wavelength region are within the tolerance, the warning display is deleted to end the operation subroutine at step #631 and the program returns. If, at step #624, it is detected that the boundary warning mode is "OFF", the program skips to step #631 where the warning display is deleted, and the program returns. That is all for the description on the operation subroutine.

Figure 17:
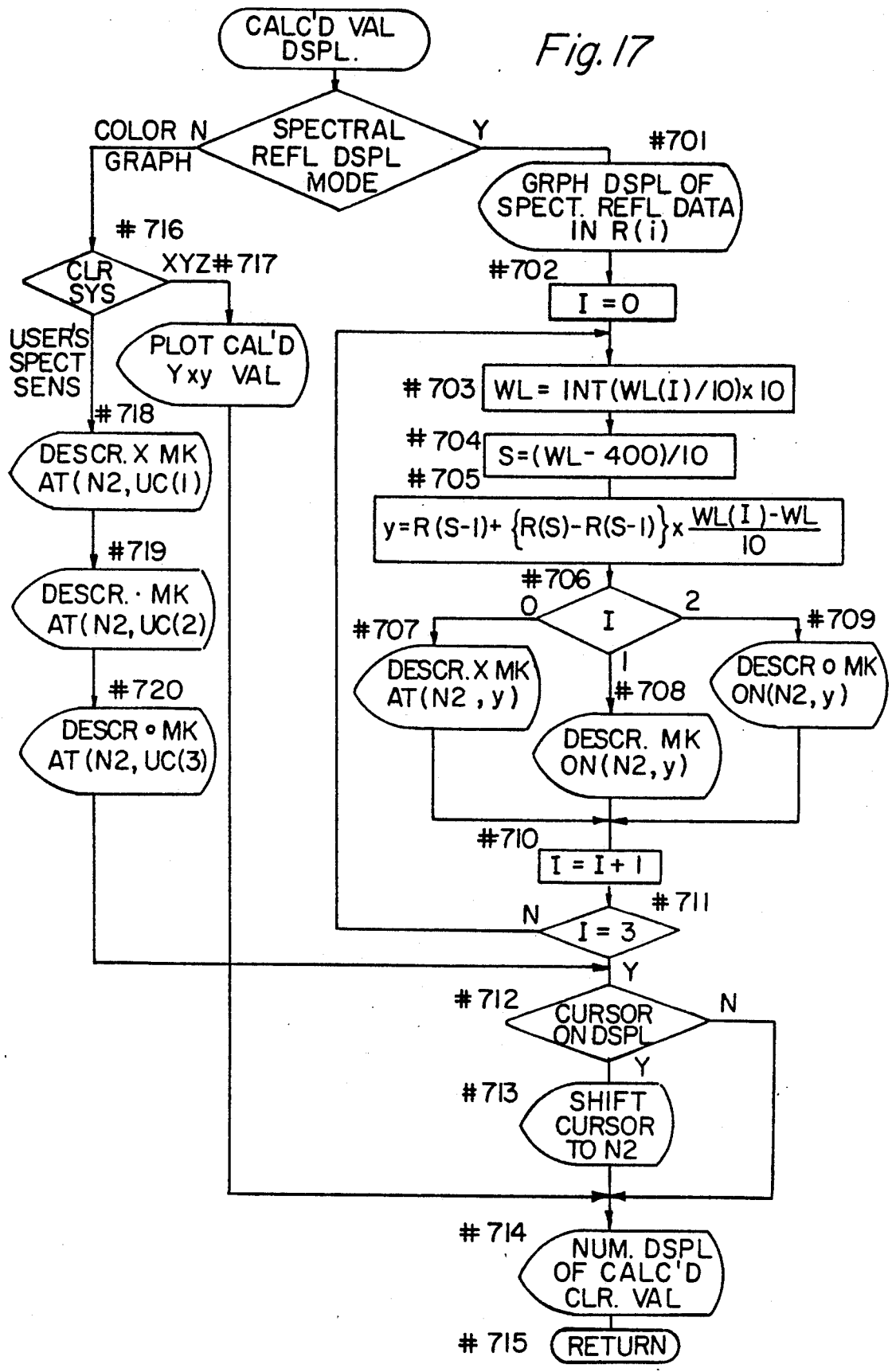
FIG. 17 is a flow chart of a calculated value display subroutine in said embodiment.
Figure 18A:
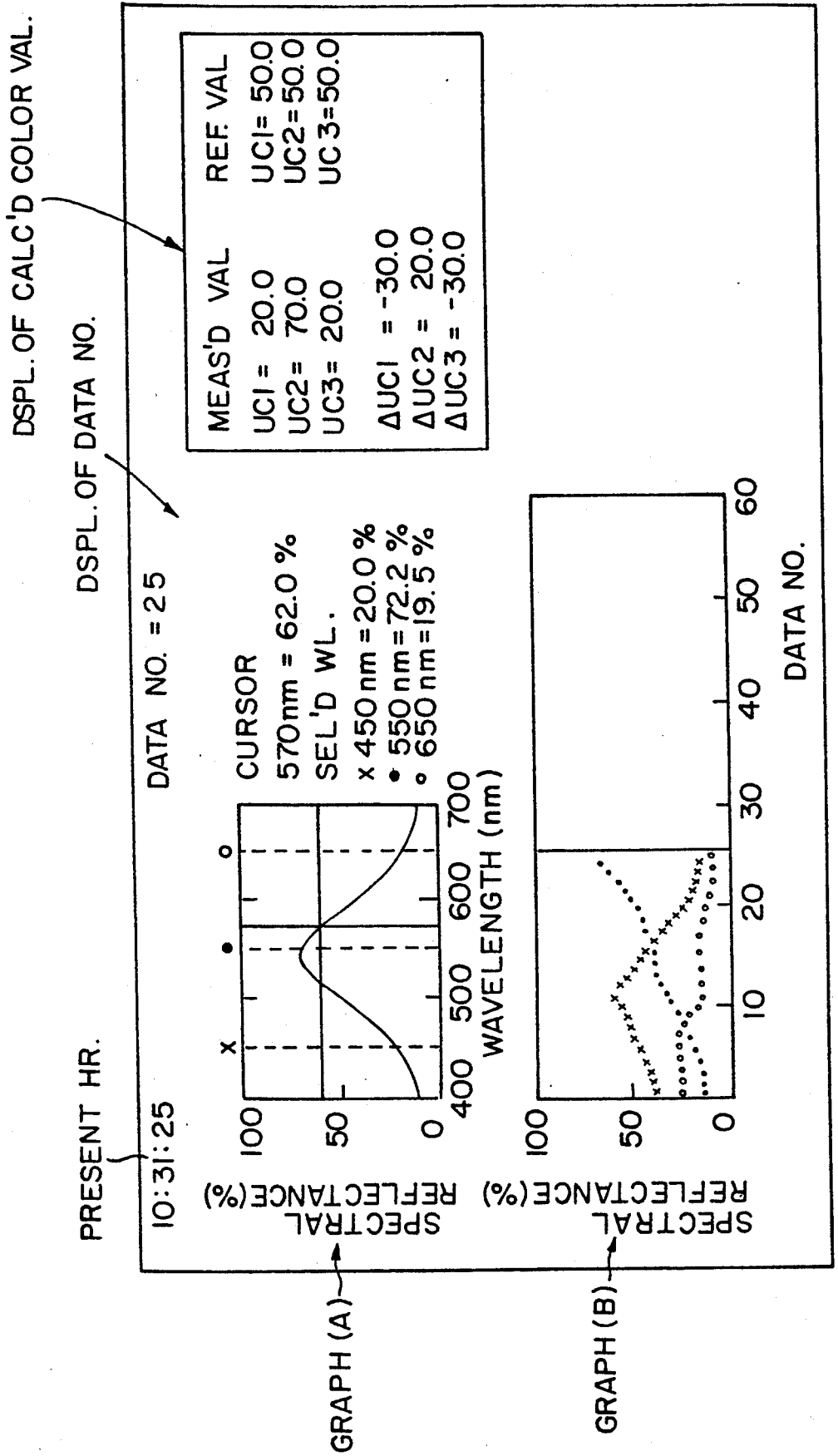
FIGS. 18(a) through 18(d) are charts showing examples of display at the display portion in said embodiment.
Figure 18B:
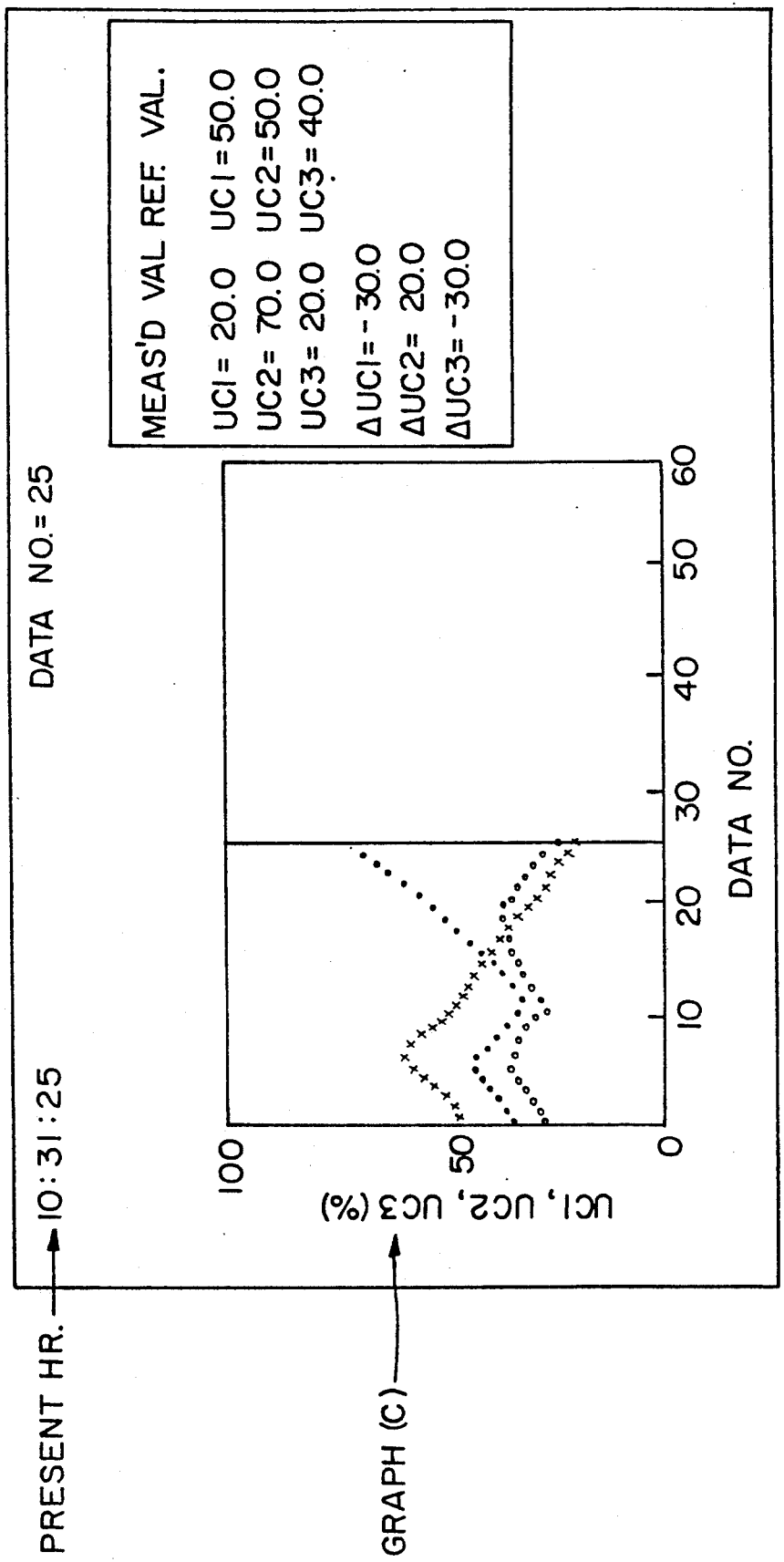

Next, the calculated value display subroutine used at step #409 of the measurement subroutine will be described hereinafter. FIG. 17 is a flow chart of the calculated value display subroutine. Examples of the display are shown in FIGS. 18(a) and 18(b). At step #700 it is discriminated whether or not the mode set at step #144 (see FIG. 11(c)) of the display mode setting subroutine is of spectral reflectance display. If the answer is yes, the program proceeds to step #701, at which, the previous measured value is deleted from the current spectral reflectance graph, if displayed there, and the measured spectral reflectance value which is stored in R(i) at present is displayed on the graph. Furthermore, at this step, it is discriminated whether the cursor display mode is in an ON-state or OFF-state. If the cursor display mode is in an ON-state, location of a cursor and a displayed data value at the cursor are modified according to the new measured value. From step #702 on, such a graph (B) is displayed that shows a change of spectral reflectance with time at the selected wavelength. First of all, at step #702, wavelength number I to be selected is cleared to zero. In this embodiment, the three kinds of wavelengths WL(0), WL(1) and WL(2) can be set with the pitch of 1 nm within the range of 400~700 nm and they have been already set at step #208 of the setting subroutine. As the measured spectral reflectance values are obtained at intervals of 10 nm, the spectral reflectance at a selected wavelength is obtained through the interpolation. At step #703, value, with units digit neglected, at the Ith wavelength WL(I) is substituted into WL. Next, at step #704, calculation of wavelength number s corresponding to the wavelength WL is carried out. At step 705, the spectral reflectance at wavelength WL(I) is calculated by the interpolation method using spectral reflectance R(s) at wavelength WL nm and spectral reflectance R(s-1) at wavelength (WL-10) nm, and is substituted into "y" of the coordinates (N2,y) on the graph (B). At step #706, value of I is discriminated. If I=0, a "x" mark is described at the coordinates (N2, y) of the graph (B) showing the spectral reflectance change with time at step #707. Similarly, if I=1, a "." mark is described at step #708, and if I=2, a "o" mark is described at step #709. In short, data of the selected wavelength WL(0) are expressed by the "x" mark, data of WL(1) by the "." mark, and data of WL(2) by the "o" mark so that those three kinds of data can be distinguished from each other. The value N2 is the data number of a data displayed, as referred to in the description on the measurement subroutine. At step #710, "1" is added to I, and then, at step #711, after the descrimination of I, the same process as carried out at steps #703 through #710 is effected with all I=0, 1, and 2. Thereafter, the program proceeds to step #712. Data display on the graph (B) is performed in such a way that new data are added on the graph (B), without deleting old data displayed immediately before the input of the new data so that the data of the spectral reflectances at all wavelengths selected may be simultaneously arranged from the left to the right in chronological order, whereby the operator can see the chronological change of spectral reflectance. On the graph (A) of spectral reflectance are described in advance dotted vertical lines in the position of the selected wavelengths and on top of the lines are described the "x, .,o" marks corresponding to each of the selected wavelengths (see FIG. 18(a)), whereby the relation between the selected wavelengths and marks can be seen apparently. At step #712, it is discriminated whether or not the cursor is on display. If it is on display, the program proceeds to step #713, at which the cursor displayed on the graph (B) showing the spectral reflectance change with time is shifted to the position of N2 on the abscissa. This cursor indicates which data on the graph (B) corresponds to the data being displayed on the graph (A) showing the spectral reflectance. If the cursor is judged not to be on display at step #712, the program skips to step #714, at which color value calculated in the operation subroutine is displayed numerically. Thereafter the calculated value display subroutine is brought to an end at step

715 and the program returns. If the discrimination at step #700 concludes that the display mode is not for displaying spectral reflectance, the display mode is for displaying a color graph, so that the program proceeds to step #716 and from this step on the process of displaying a color graph is carried out (see FIG. 18(b)).

At step #716, it is discriminated whether the present color display system is the XYZ colorimetric system or the user's spectral sensitivity color display system. If the XYZ system is detected, the program proceeds to step #717, at which Yxy calculated values are plotted on the Yxy chromaticity coordinates graph, and then the program proceeds to step #714. On the other hand, if the user's spectral sensitivity color display system is detected, the "x" mark is described at the coordinates (N2, UC(1)) on the graph (C) showing the user's color change with time, the "●" mark at the coordinates (N2, UC(2)), and the "○" mark at the coordinates (N2, UC(3)) at steps #718 through #720. Then the program proceeds to step #712 UC(1). UC(2). and UC(3) are color values calculated corresponding to the user's spectral sensitivities US1(i), US2(i), and US3(i), respectively, as described referring to the operation subroutine. At steps #712 and #713, a cursor is displayed to indicate which data existing on the graph (C) showing the user's color change with time corresponds to the data of the data number on display, similarly to the case of the graph (B) showing the spectral reference change with time. Thereafter, at step #714, calculated color values are numerically displayed and the program returns.

In this embodiment, the values UC(1), UC(2) and UC(3) are plotted on the graph (C). Further, it may be easy to provide a function to plot the deviation from the reference values, ΔUC(1), ΔUC(2), ΔUC(3), on a graph. Marking each coordinates on the graphs (B) and (C) with "x", "." or "○" serves to distinguish between the wavelengths selected. In case of using a colored display unit, the distinguishing might be effected by the variation of colors. That is all for the description on the calculated value display subroutine.

Figure 19A:
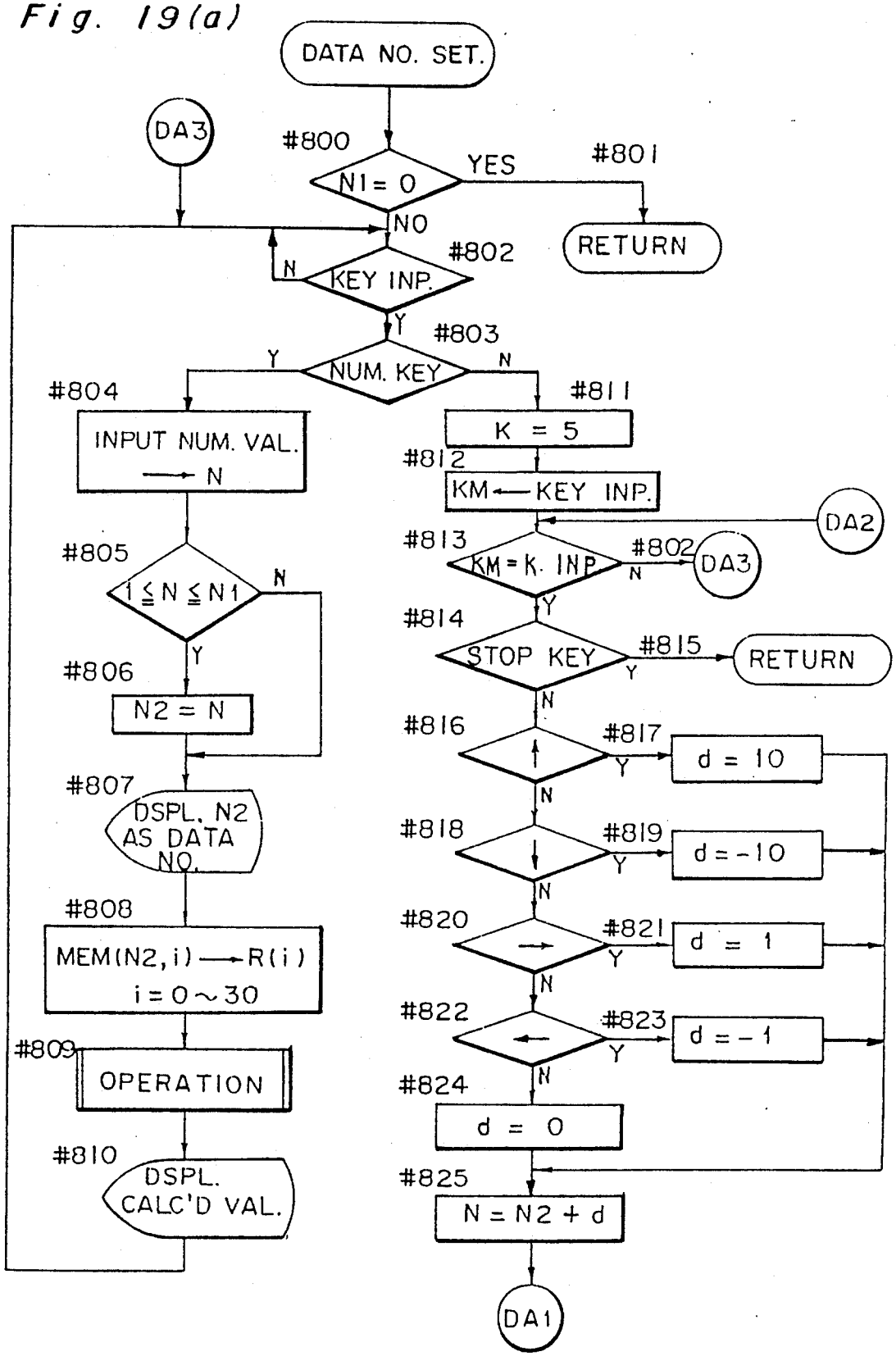
FIGS. 19(a) and (b) are flow charts of a data number setting subroutine in said embodiment.
Figure 19:
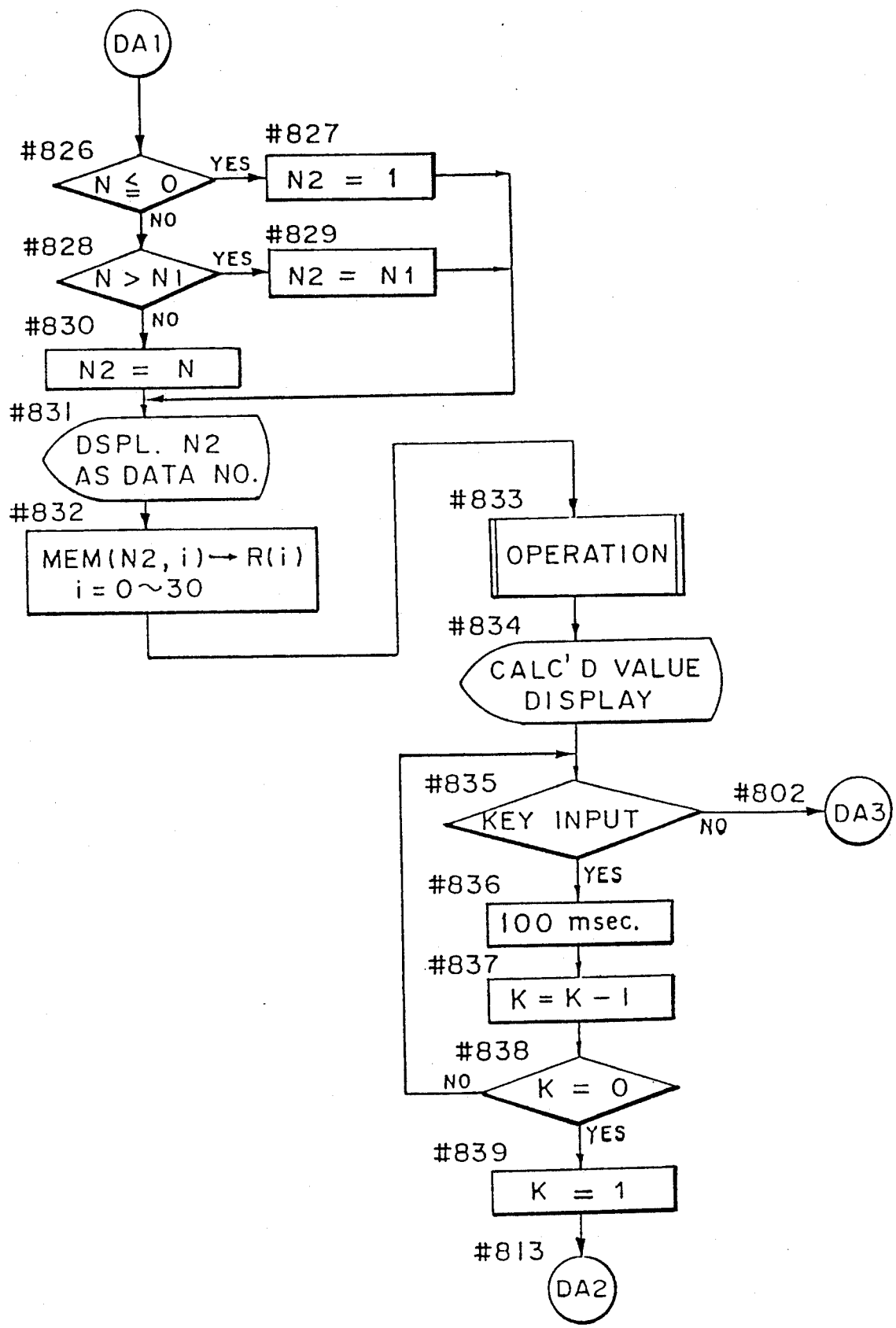

The data number setting subroutine is now described. FIG. 19 shows a flow chart of the data number setting subroutine. This subroutine is for taking data having an arbitrary number out of the N1 memories storing measured values for the purpose of display thereof as spectral reflectance data. The operator inputs a data number and data corresponding to the input data number will be called. Inputting of data numbers can be done by inputting numerical data using numerical keys. Alternatively, the data number inputting can be done by increasing or decreasing data number continuously with use of " ↑ " key, " ↓ " key, "→" key or "←" key. By changing the data number continuously and displaying stored data corresponding to the data number on a graph, each time the data number changes, the change of the spectral reflectance data with time can be seen as a dynamic image of the spectral reflectance graph. The description below will be given by way of the flow chart of FIG. 19. At step #800, it is checked whether or not N1 (data no. of the final measurement value)=0. When N1=0, the program proceeds to step #801 without taking any procedure and returns because N1=0 means that there is no measured value. Unless N1=0, the program proceeds to step #802 and time is counted till an input from the keyboard. On receiving an input, the program proceeds to step #803, at which it is discriminated whether or not the key is a numerical key. If it is a numerical key, the input by the key is considered as an input of a data number from the numerical keys, and so, numerical values inputted from the numerical keys are stored in variable N at step #804. When discrimination whether or not value of N is appropriate at step #805 concludes that N is appropriate, N is substituted into N2 at step #806, and then, the program proceeds to step #807. N2 is a variable indicating the data number of the data on display, as described before. When the discrimination at step #805 concludes that N is not an appropriate value, the program skips to step #807 without changing value of N2. At step #807, value of N2 is indicated as data number. At step #808, contents of the N2th memory MEM (N2, i) is put into the spectral reflectance data R(i). After the effectuation of the operation subroutine using R(i) at step #809 and of the calculated value display subroutine at step #810, the program returns to step #802. When it is judged, at step 803, that the key is not a numerical key, the program skips to step #811, at which a variable k used for controlling a speed to change the data number is set to be 5. With larger value of k, the speed becomes lower. At step #812, information inputted by the keys are stored in a variable KM. Then, at next step #813, it is discriminated whether or not the inputted information is equal to information stored in KM. If they are equal, the program proceeds to step #814, at which it is discriminated whether or not the key is the "STOP" key. If it is the "STOP" key, the data number setting subroutine is brought to an end at next step #815 and the program returns. Unless the key is the "STOP" key, the program proceeds to step #816. From step #816 to step #824, the following process is carried out. First, information inputted by keys is checked. When input of " ↑ " key is found out, variation value d to change the data number is set to to be 10, and similarly, when " ↓ " is found out, d is set to be −10, when "→" is found out, d is set to be 1, when "←" is found out, d is set to be −1, and when other keys are foud out, d is set to be 0. Thereafter the program proceeds to step #825, at which value of N2 plus d is substituted into N. Descrimination whether or not the value N is appropriate is effected at steps #826 through #830. If N is below zero, N2 is set to be 1. If N is larger than N1 which is a data no. of the final measurement value, N2 is set to be N1. Then, the program proceeds to step #831. When the descrimination of the value N concludes that it is an appropriate value, the value of N is substituted into N2 and then the program proceeds to step #831. At this step the value N2 is presented as a data no. At next step #832, data stored in the N2th memory MEM (N2, i) is stored as the spectral reflectance data R(i) at step #832. At step #833 the operation subroutine is carried out, and then at step #834 the calculated value display subroutine is carried out. Process carried out from step #835 on is for discriminating on the pushing of keys and for counting time required to regulate speed of data changing. At step #835 it is discriminated if a key is pushed or not. If no key is pushed, the program returns to step #802 and a key input is awaited. If some key is pushed, time length of 100 msec. is counted at step #836. At step #837 "1" is subtracted from the value of k. After that, the value of k is discriminated at step #838. If k is not zero, the process at steps #835 through #837 is repeated until k becomes zero. When k becomes zero, k is set to be 1 at step #839 and the program returns to step #813. At this step, key input information stored in the memory KM is compared with the current key input information. If both informations are not equal to each other, the program returns to step #802, at which a new key input is waited When they corresponds to each other, the increase or decrease of the data number is repeated. In other words, the keeping on pushing one of " ↑ ", " ↓ ", "→" and "←" keys causes the data number to increase or decrease continuously. In this case, the time length of the interval between the first and second data number changings is 500 msec., and then time length of intervals is shortened to 100msec. With " ↑ " or " ↓ " key, the data number increases or decreases at high speed, or by ten, while, with "→" or "←" key, at low speed, or by one. In short, the operator can change the speed of changing the data number in four ways. Therefore, when change of the spectral reflectance with time is considered as an dynamic image of the spectral reflectance graph, it is useful to be able to select the speed. That is all for the data number setting subroutine.

Figure 18D:
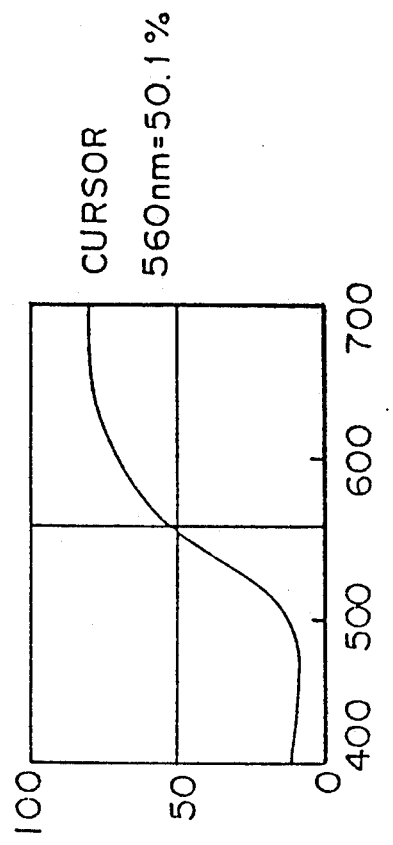
Figure 18C:
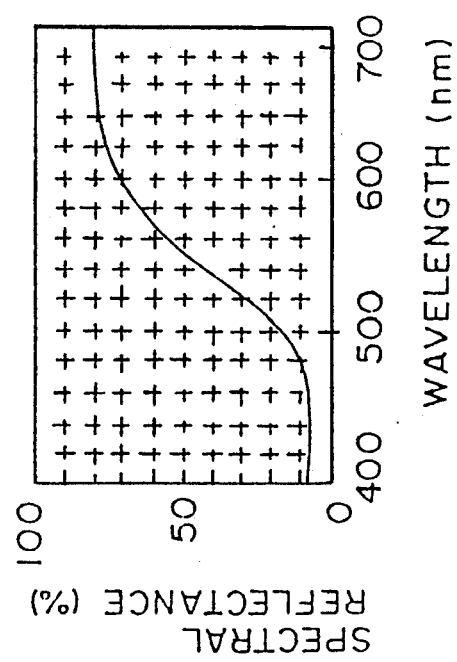
Figure 20:
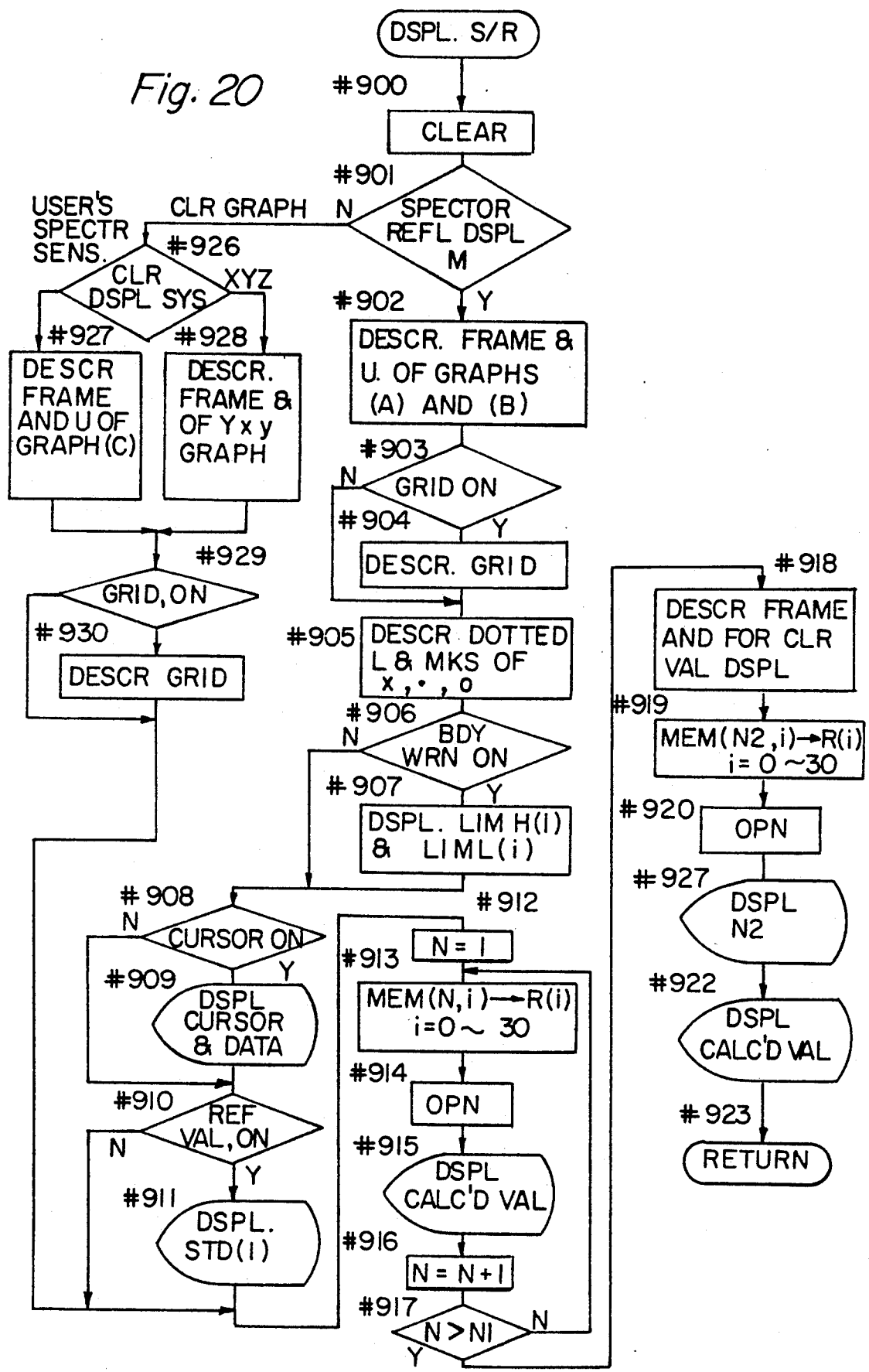
FIG. 20 is a flow chart of a display subroutine in said embodiment.

Hereafter, a description will be made on the display subroutine used at step #102 in the flow chart of the main program shown in FIG. 11(a). While the aforementioned calculated value display subroutine is for displaying measured values or calculated values on the graph scale which is already on display, the display subroutine in question is for describing a graph newly on the basis of a new display mode, color display system and/or wavelength selected, if the previous ones have been changed, or for displaying again a graph, which had been on display before the display other than the graph was on the screen temporarily. FIG. 20 shows a flow chart of the display subroutine. Examples of the display are shown in FIGS. 18(c) and 18(d).

First of all, at step #900, all displayed is deleted. At step #901, discrimination on the display mode is carried out. If the discrimination concludes that the spectral reflectance is to be displayed, the program proceeds to step #902, at which a frame and units of the spectral reflectance graph and of the spectral reflectance change graph are described. At step #903 it is discriminated whether the grid display mode is in an ON-state or OFF-state. If it is in an ON-state, grid is described on the graphs of spectral reflectance and of change of spectral reflectance with time at step #904 (see FIG. 18(c)). When it is discriminated that the grid display mode is "OFF" at step #903, the program skips to step #905, at which vertical dotted lines and "x, ., o" marks are described on the spectral reflectance graph to indicate the position of each selected wavelength. At step #906, it is discriminated whether the boundary warning mode is in an ON-state or OFF-state. If it is in an ON-state, the upper bound data LIMH(i) and lower bound LIML(i) of the spectral reflectance are presented on the spectral reflectance graph at step #907, and then the program proceeds to step #908. If the boundary warning mode is in an OFF-state, the program skips from step #906 to step #908. At this step, it is discriminated whether the cursor display mode is in an ON-state or OFF-state. If it is in an ON-state, a cursor is displayed and data at the point of the cursor is numerically displayed at step #909 and the the program proceeds to step #910 (see FIG. 18(d)). If the cursor display mode is in an OFF-state, the program skips to step #910. At this step a discrimination is carried out to see whether the reference value display mode is in an ON-state or OFF-state. If it is in an ON-state, the reference value data STD(i) is shown on the spectral graph before the program proceeds to step #912. When in an OFF-state, the program skips to step #912. If it is judged, at step #901, that the mode of displaying a color graph is in an ON-state, the program proceeds to step #926, at which it is discriminated whether sensitivity. With the XYZ colorimetric system, a frame and units for the Yxy graph are described, on the other hand, with the user's spectral sensitivity, a frame and units for the graph of user's color change with time are described. Then, at step #929, a discrimination is carried out to see whether the grid display mode is in an ON-state or OFF-state. When it is in an ON-state, the program proceeds to step #930, at which grid is described on the Yxy graph or on the user's color change graph and then, step #912 comes next. When it is in an OFF-state, the program skips to step #912.

At steps #912 through #917, substitution of measurement value memory into the spectral reflectance R(i), the operation subroutine, and the calculated value display subroutine are carried out with respect to each of the first measurement value memory MEM(1,i) through the N1th measurement value memory MEM(N1,i) in order to plot the memory information of those memories on the spectral reflectance change graph or the Yxy graph or the user's color change graph. Steps #918 through #922 are for carrying out the process of displaying the spectral measurement value memory MEM(N2,i). First, at step #918, a frame and units for displaying the color value numerically are described. Then, at step #919, MEM(N2,i) is substituted into R(i), and at step #920 the operation subroutine is carried out. At step #921, the value of N2 is shown as data number, thereafter, the calculated value display subroutine is carried out at step #922 and the program returns. That is all for the description on the display subroutine.

Figure 11C:
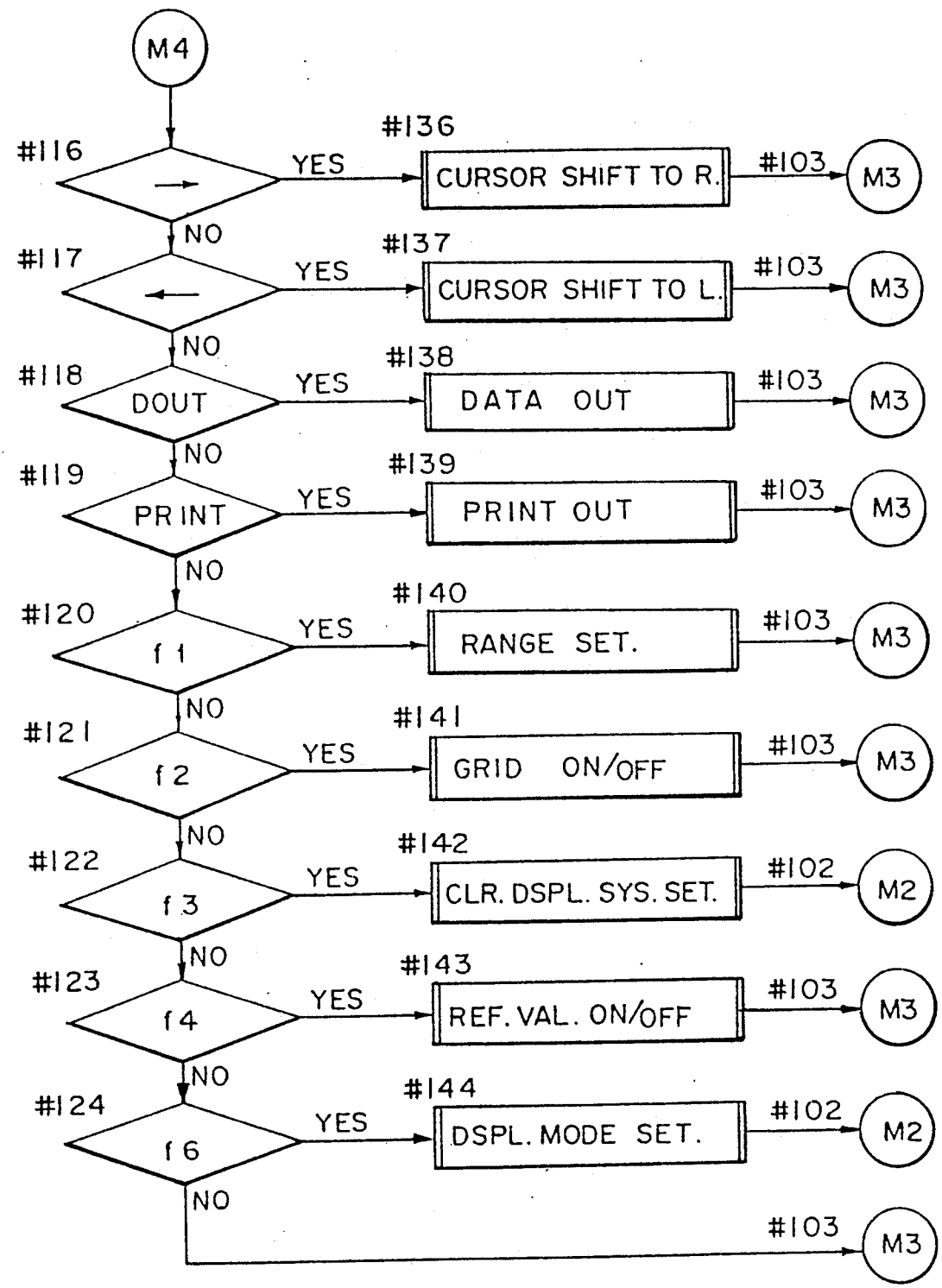
Figure 21:
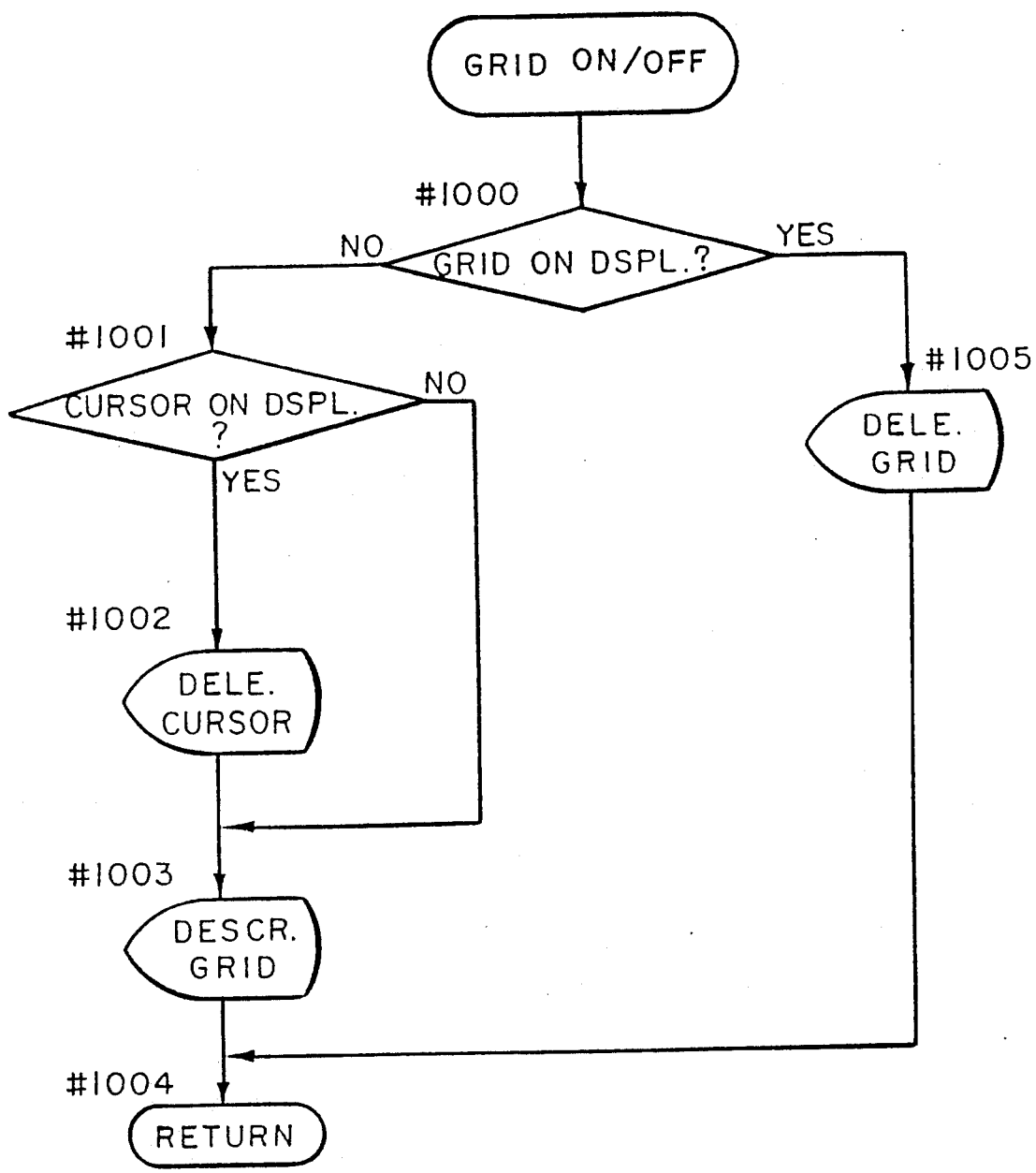
FIG. 21 is a flow chart of a grid ON/OFF subroutine in said embodiment.

Now, the description on the grid ON/OFF subroutine used at step #141 of FIG. 11(c) starts. This subroutine is for the process of deleting the grid, if displayed, or of describing the grid, if not displayed. When a cursor is displayed, the cursor is deleted before the description of the grid. A flow chart of this process is shown in FIG. 21.

Figure 22:
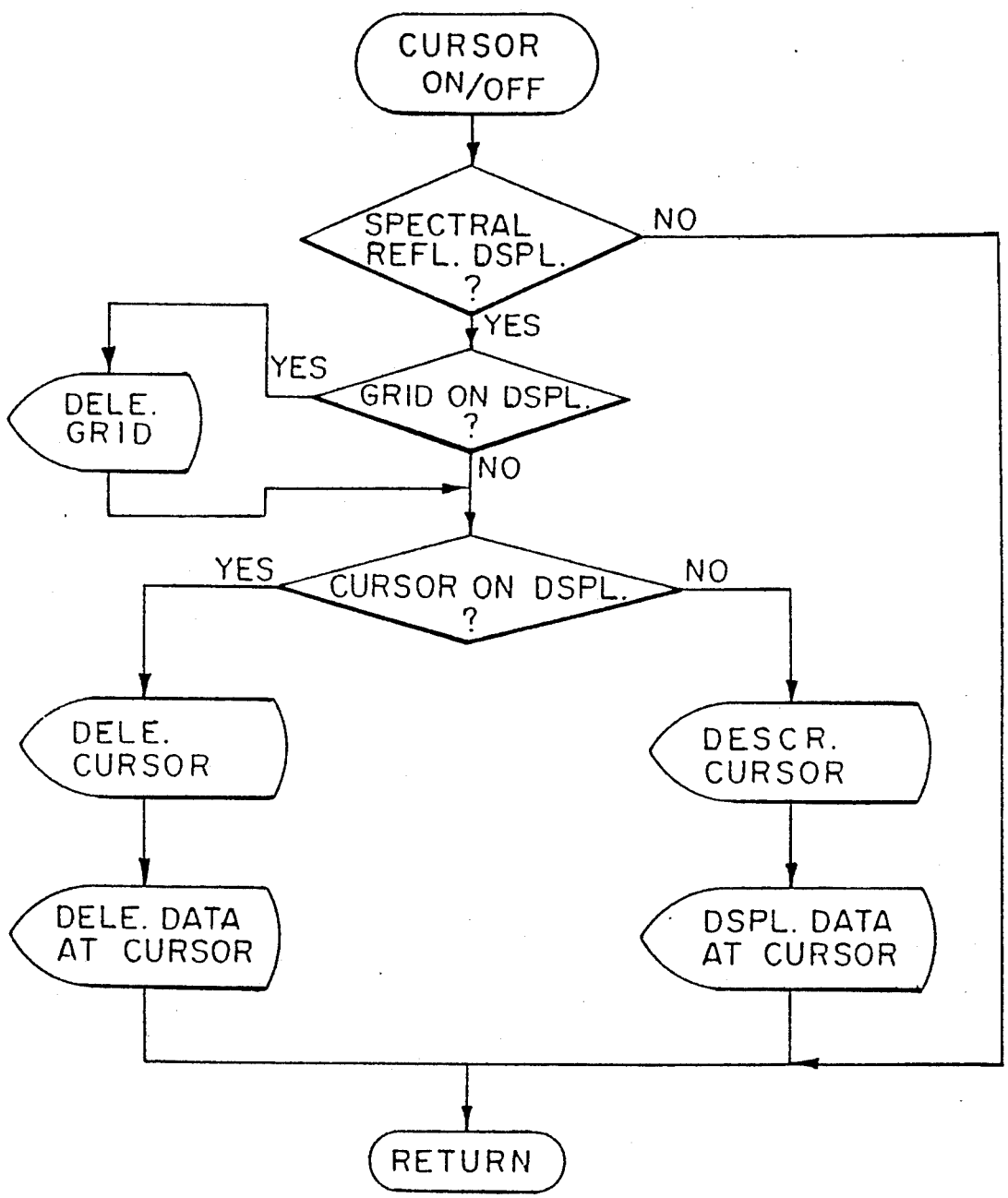
FIG. 22 is a flow chart of a cursor ON/OFF subroutine in said embodiment.

Next, the cursor ON/OFF subroutine used at step #135 of FIG. 11(b) will be described. This subroutine is carried out to delete the cursor and the numerical value at the point of the cursor when the cursor is on display under the spectral reflectance display mode, and to display the cursor and the numerical value at the point of the cursor when the cursor is not on display. If the grid is on display, the description of the cursor and the numerical data at the cursor is effected after the deletion of the grid. A flow chart of this process is shown in FIG. 22. As is obvious from the description on the grid ON/OFF subroutine and the cursor ON/OFF subroutine, some consideration is given so that the grid and the cursor may not be displayed simultaneously, whereby difficulty in seeing a graph due to the coexistence of the grid and the cursor is prevented.

Figure 23:
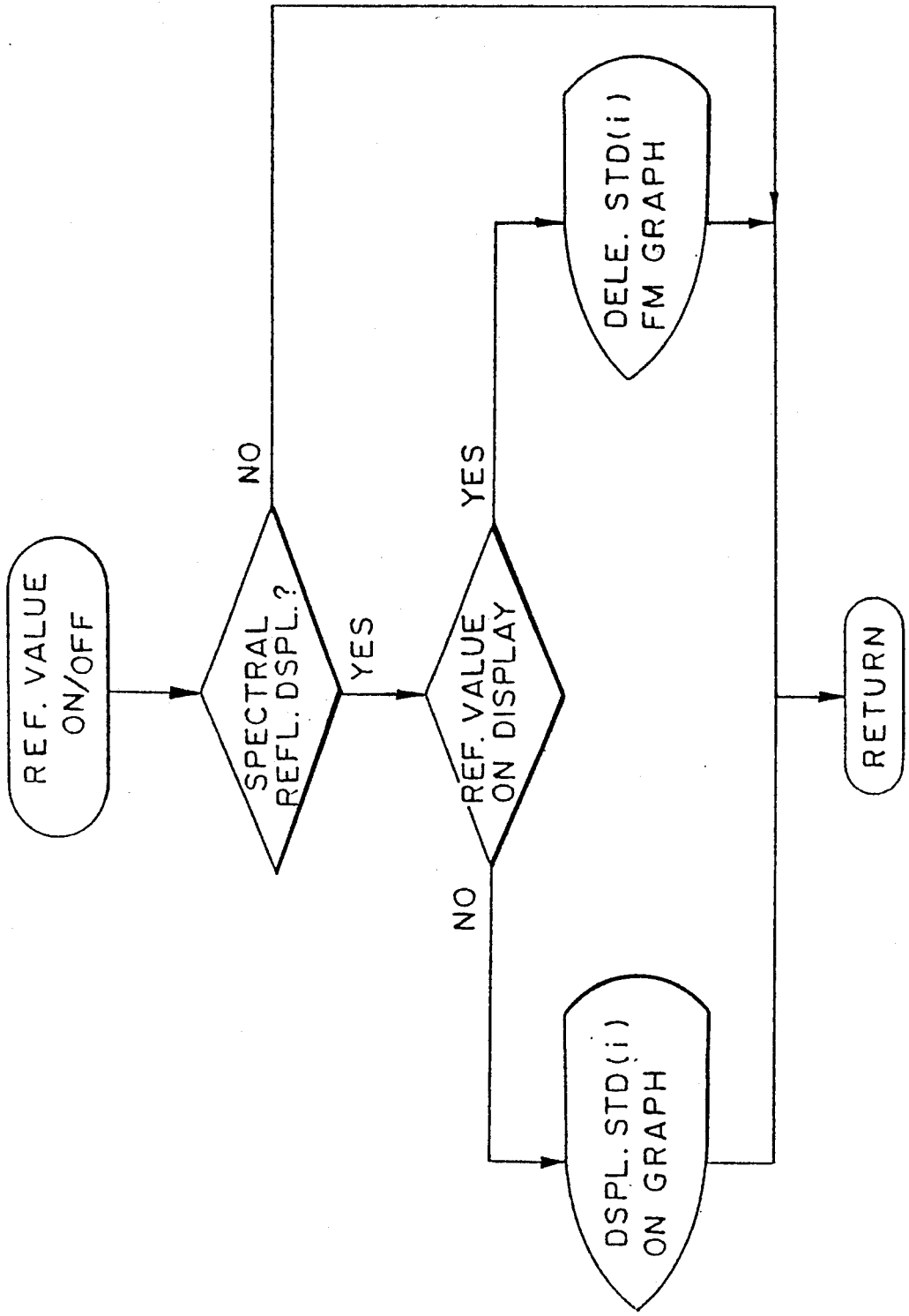
FIG. 23 is a flow chart of a standard value ON/OFF subroutine in said embodiment.

Finally, the reference value ON/OFF subroutine used at step #143 of FIG. 11(c) will be hereinafter described. This subroutine is carried out to decide whether or not to display the reference value STD(i) and the measured spectral reflectance value at the same time on the spectral reflectance graph under the spectral reflectance display mode. When the reference value STD(i) is judged to be on display on the spectral reflectance graph, it is deleted from the graph. On the other hand, when the reference value STD(i) is not on display on the graph, the value STD(i) is displayed together with measured values. A flow chart of this process is shown in FIG. 23. That is all there is to tell about the first embodiment.

Next, a second embodiment of the present invention will be hereinafter described. In the first embodiment, the number of the photodiodes included in the spectral sensor S2 for measuring the light source is equal to that of the sensor S1 for measuring the test piece. On the other hand, as will be understood from the description below, where the spectral energy distribution of the light source varies gently with respect to the wavelengths, the number of photodiodes included in the sensor S2 is decreased, so that the measurement of the spectral energy distribution is performed for the wavelengths at long intervals and values for wavelengths other than those can be calculated by an interpolation method. In this way, measurement can be effected with sufficient accuracy.

Figure 31:
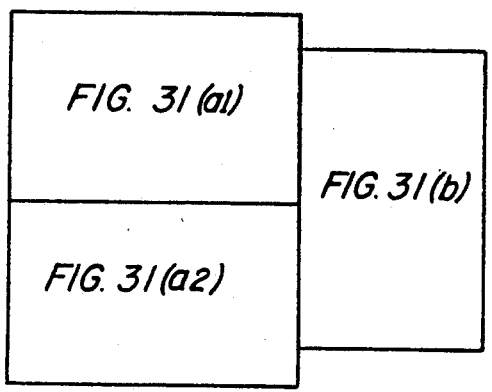
FIGS. 31(a1), 31(a2), and 31(b), taken together as shown in FIG. 31, are circuit diagrams showing the photometric circuit in the second embodiment.
Figure 4:
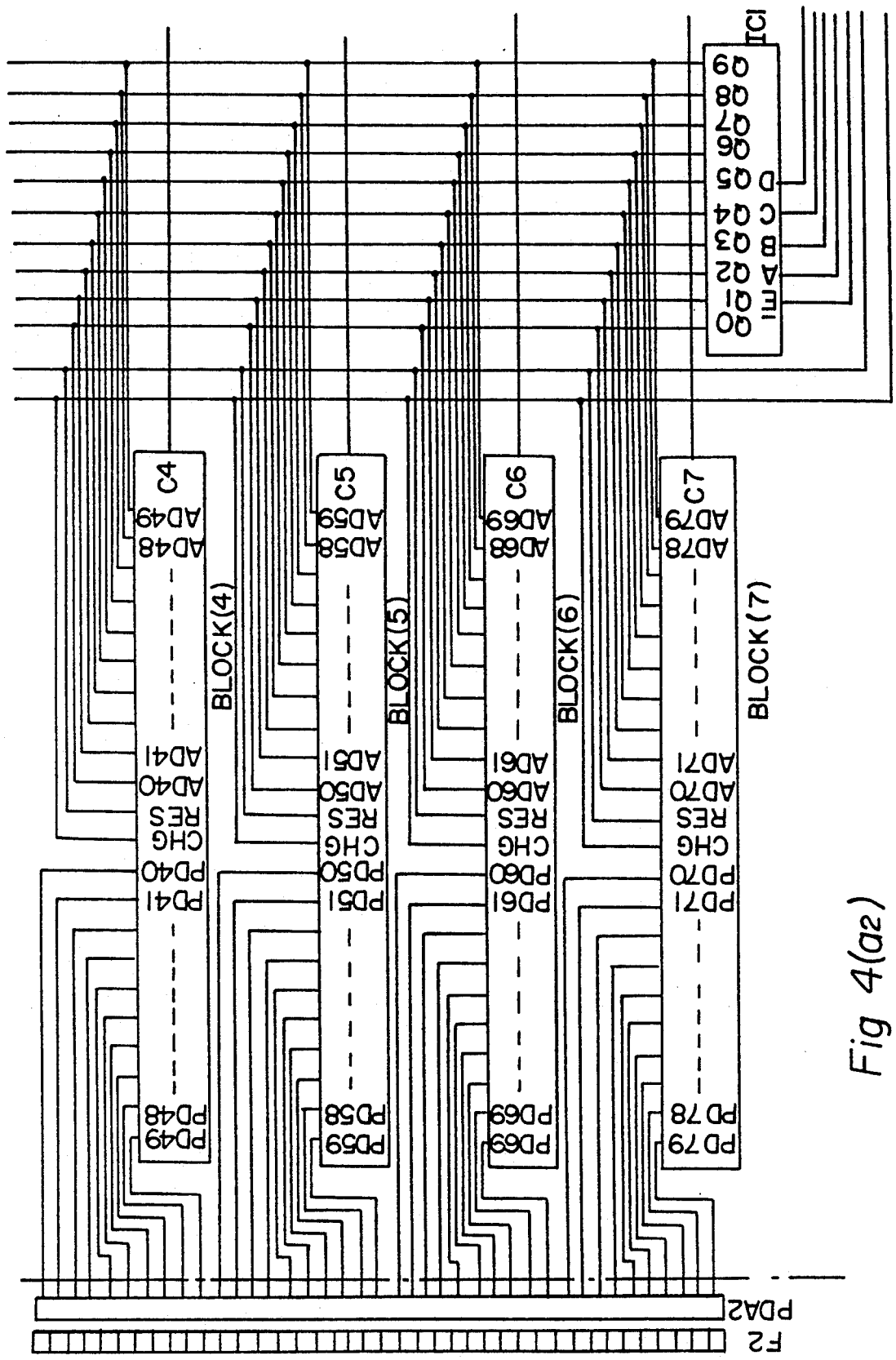
Figure 4B:
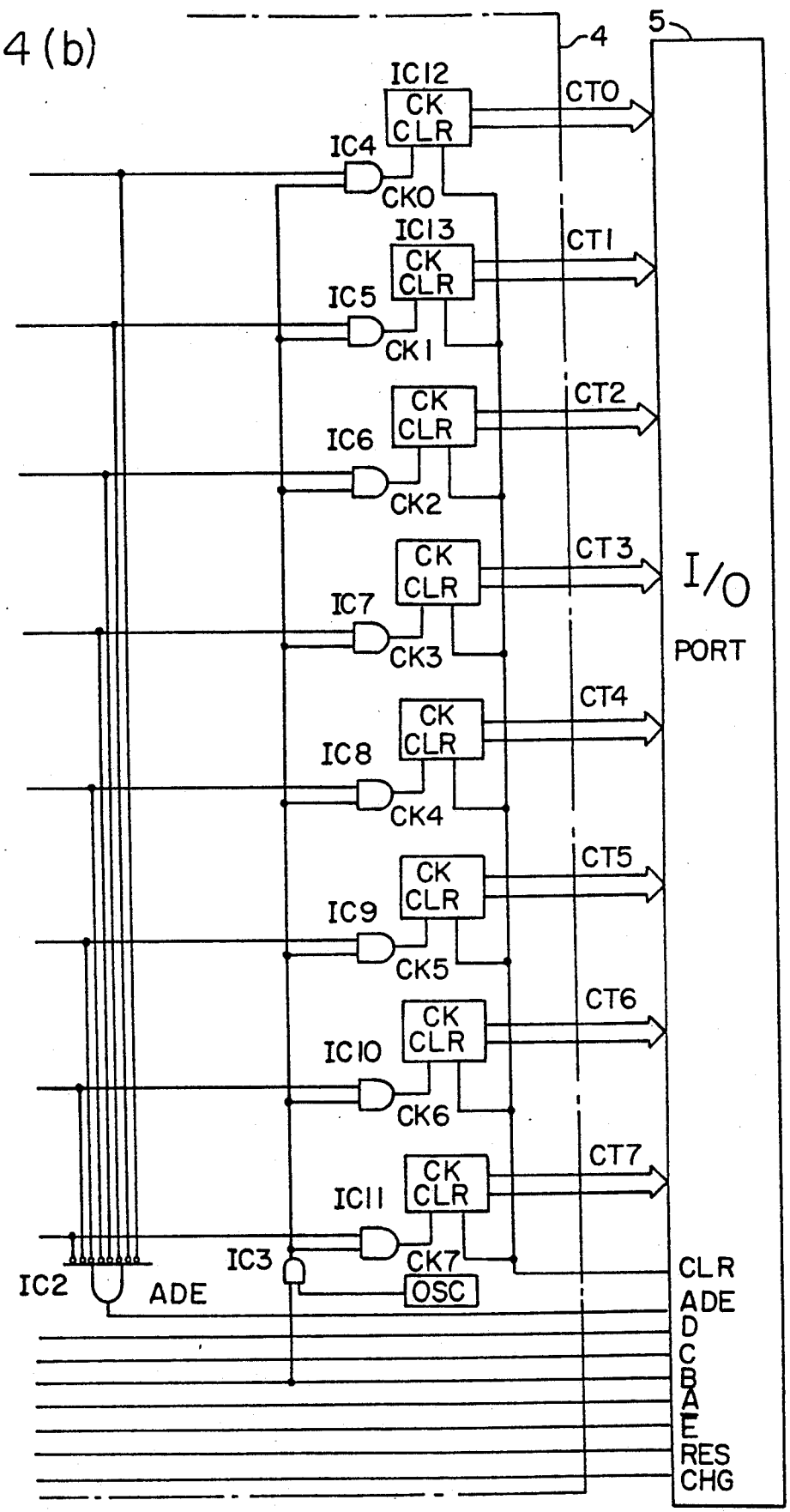
Figure 29:
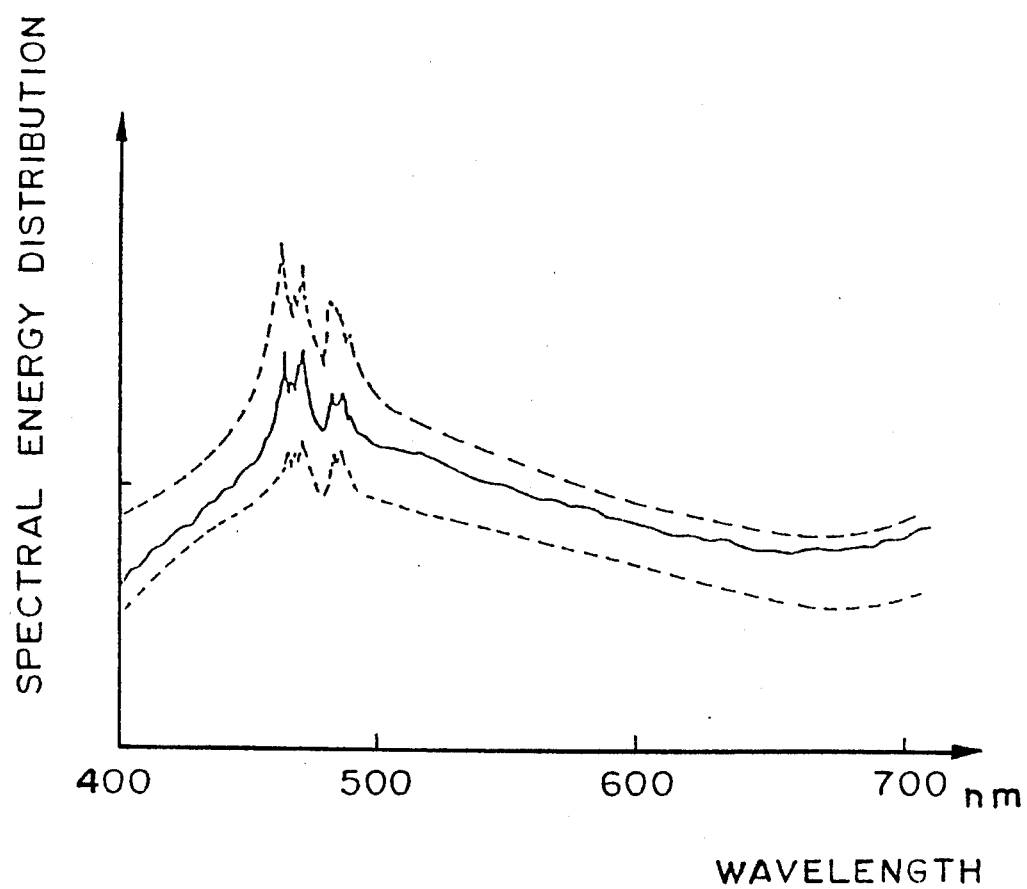
FIG. 29 is a diagram showing the variation of the spectral energy distribution of the pulse xenon lamp used in a second embodiment.
Figure 30:
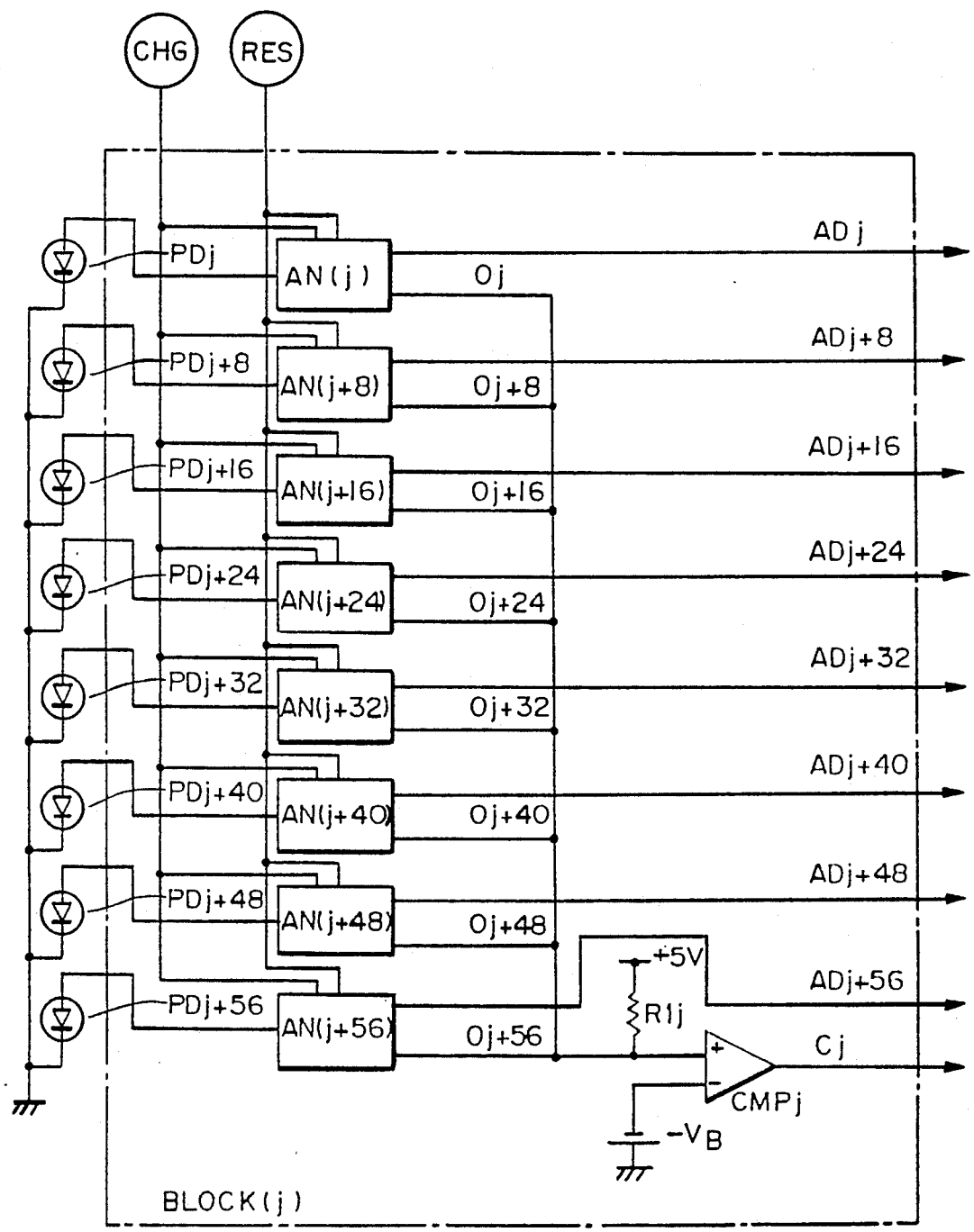
FIG. 30 is a circuit diagram showing a block of a photometric circuit in the second embodiment.
Figure 31:
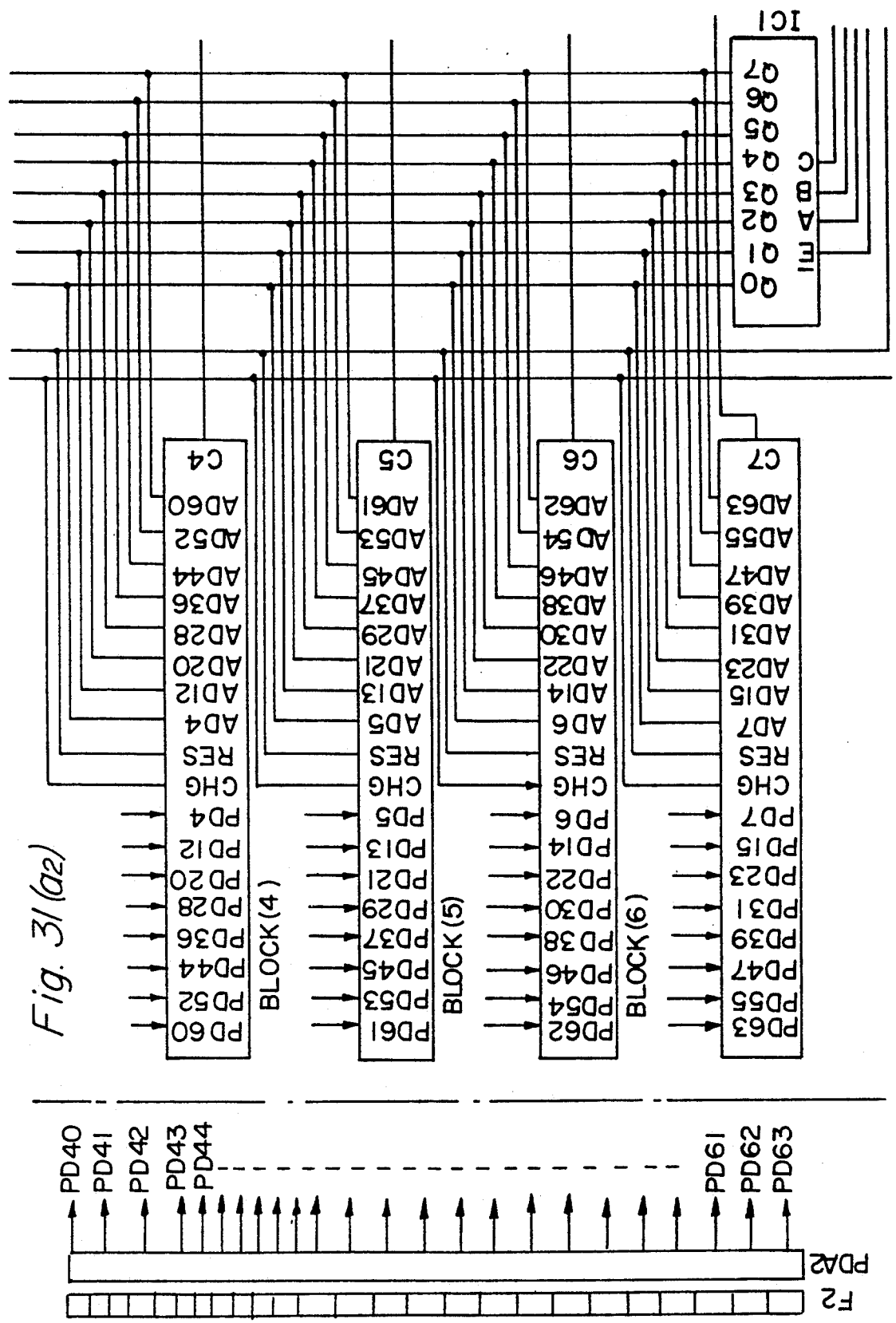
Figure 31B:
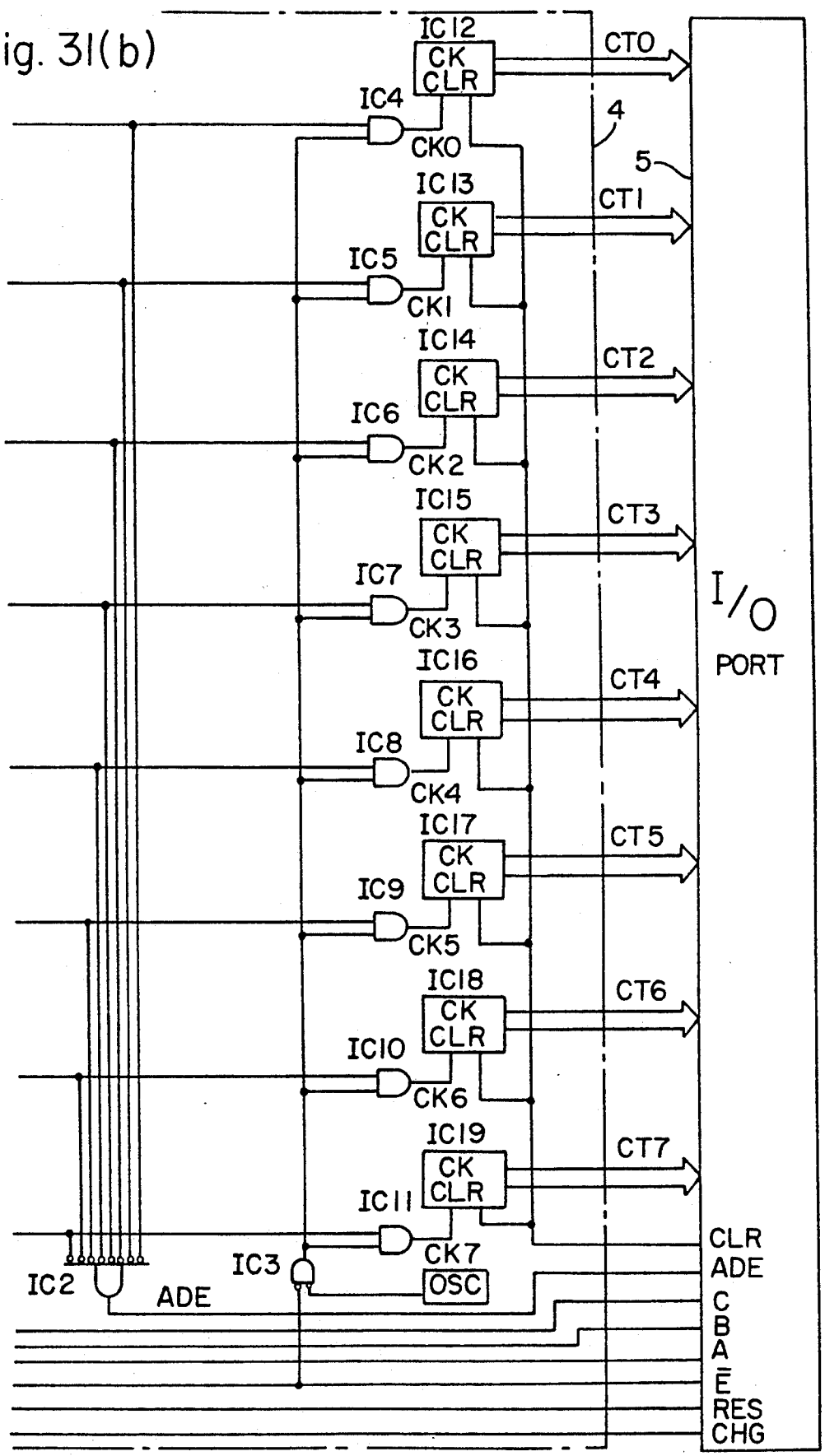
Figure 32A:
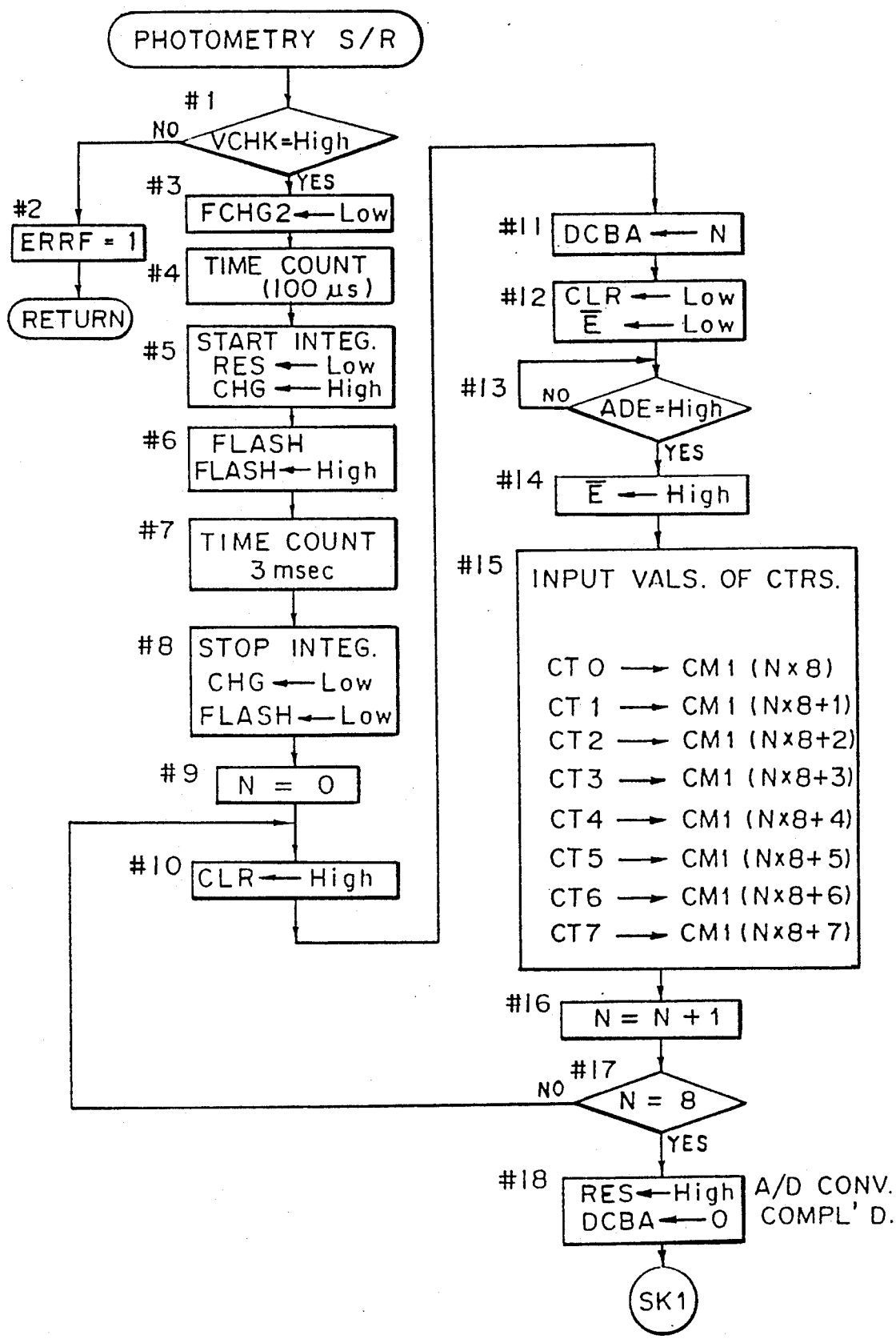
FIGS. 32(a) through 32(d) are a flow chart of the photometric subroutine in the second embodiment.
Figure 32B:
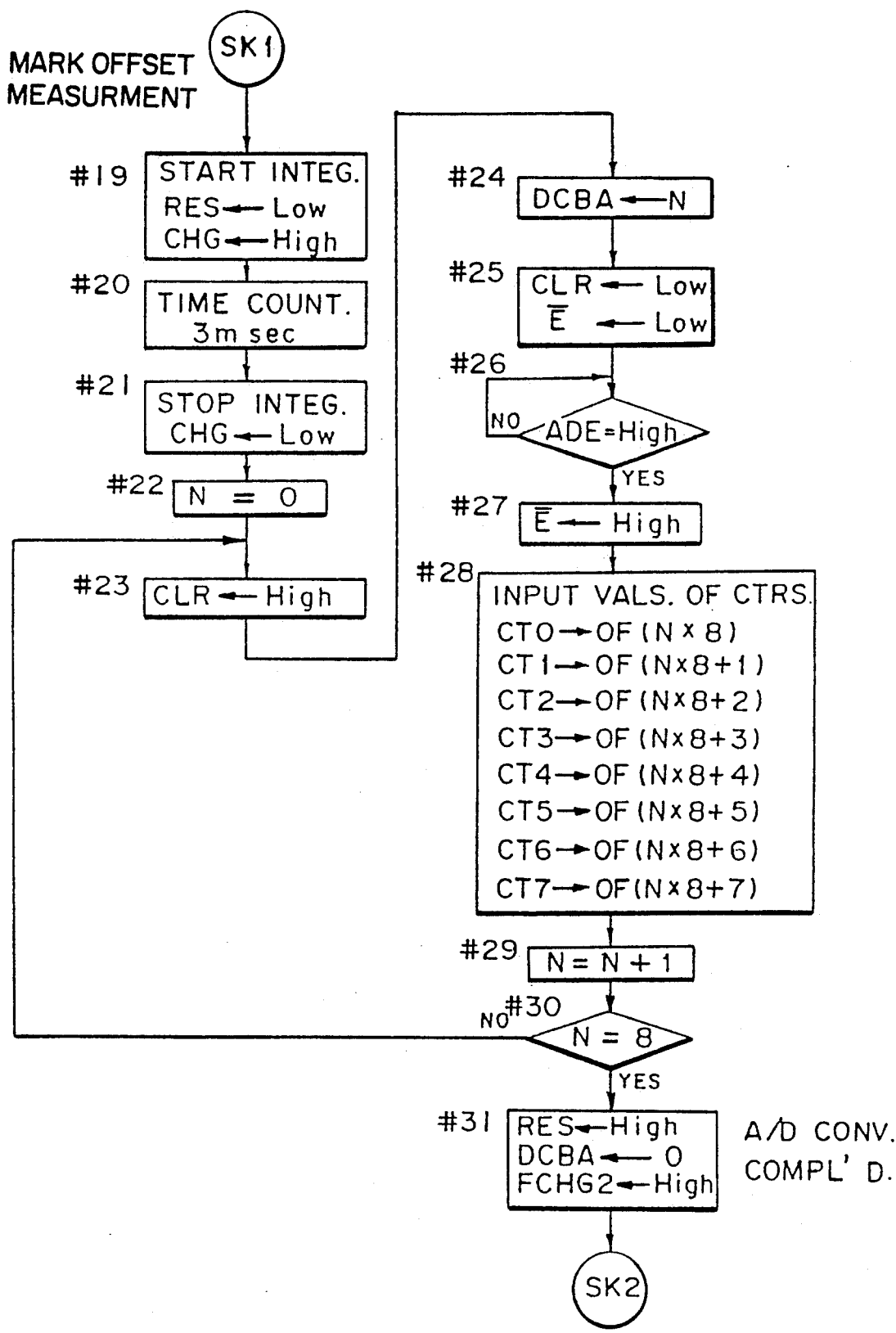
Figure 32C:
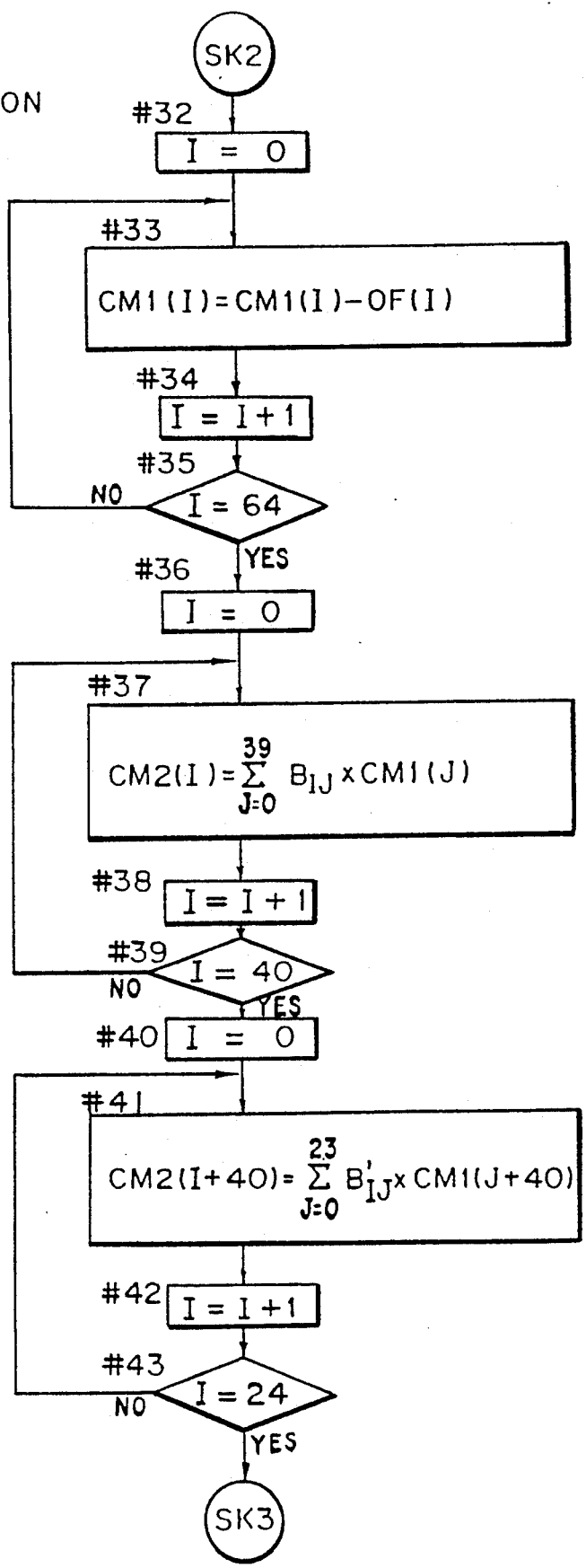
Figure 32D:
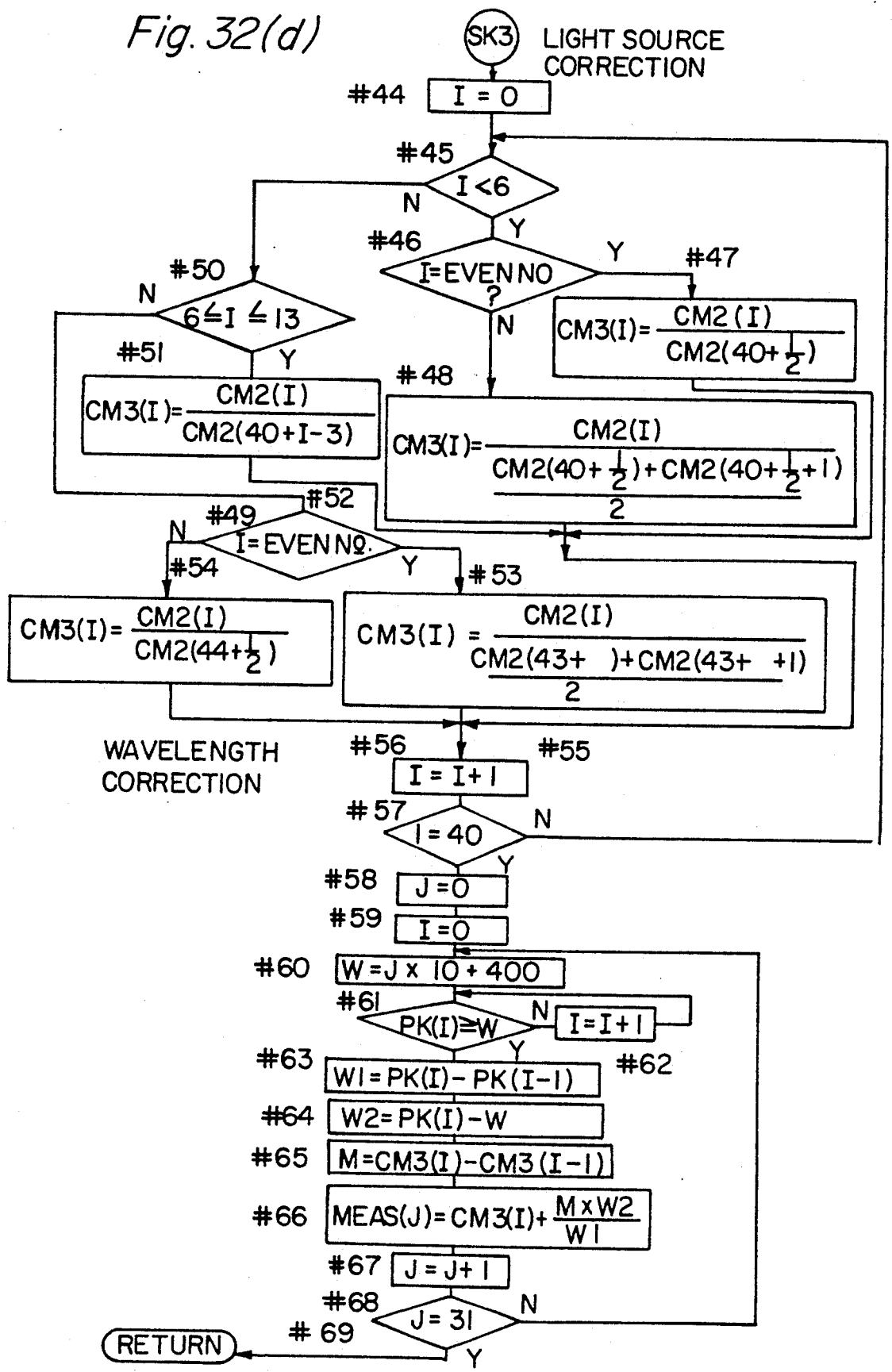

FIG. 29 shows the spectral energy distribution of the pulse xenon lamp used as the illumination light source and the variation of the spectral energy distribution at each flash of the pulse xenon lamp (the degree of variation is exagerated for convenience). As the figure indicates, a bright line is present between 450 nm and 500 nm of a wavelength band and the spectral energy distribution varies greatly and sharply with respect to wavelengths in that range in each flash, though the spectral energy distribution varies gently in the wavelengh region other than that range. According to this fact, if the measurement wavelength pitch of the spectral sensor S2 is made equal to that of the spectral sensor S1 in the wavelength region of 450 nm to 550 nm, and if the former is made larger than the latter in the wavelength region other than that region of 450 nm to 550 nm so that the number of the photodiodes can be reduced, and that a value for a wavelength present in each interval of the measurement wavelengths of the light source is calculated by the interpolation method, components of the analog circuits can be reduced in number without lowering the measurement accuracy. As for the order for effecting the A/D conversion of the measured values, the A/D conversion in the spectral sensor S1 is effected simultaneouly with that in the spectral sensor S2 in the first embodiment. When the number of elements of the spectral sensor S2 is reduced and the A/D conversion therein is effected either prior to or posterior to that in the spectral sensor S1, time required for the A/D conversion becomes short as a whole. FIGS. 30 and 31 show an example ciruit in this case.

The spectral sensor S2 for light source measurement is constructed so that photodiodes PD43 through PD50 for a wavelength region from around 450 nm to around 500 nm may be adapted to receive light components of wavelengths with a pitch of 10 nm and that photodiodes other photodiodes in the spectral sensor S2 is twenty four, that is, sixty four together with the spectral sensor S1. Every BLOCK (i) (i=0~7) in the photometric circuit includes eight voltage-current conversion and integration circuits, as shown in FIG. 30. The order of connecting photodiodes in each block is different from that of the first embodiment as shown in FIG. 31. In the second embodiment, at first, eight photodiodes PD0, PD1, ..., PD7, one in each of eight blocks, of the spectral sensor S1 are A/D converted and then the A/D conversion is repeated similarly four times more till the conversion is completed with all the photodiodes of the spectral sensor S1. Thereafter, the A/D conversion is carried out with all the photodiodes of the spectral sensor S2, similarly. In this case, the A/D conversion is repeated only three times because the spectral sensor S2 has only twenty four photodiodes. In short, the spectrophotometer according to the first embodiment requires eighty photodiodes and eighty current-voltage conversion and integration circuits corresponding thereto, and therefore, it is required to repeat the A/D conversion of every eight photodiodes ten times. Compared with this, the sixty four photodiodes and the same number of the current-voltage conversion and integration circuits are sufficient for the spectrophotometer according to the second embodiment, and the A/D conversion of every eight photodiodes are repeated only eight times in all. As understood from this, according to the second embodiment, the photometric circuit can be constructed on a small scale and the A/D conversion can be effected rapidly.

FIGS. 32($a$) through 32($d$) show a photometric subroutine of this embodiment. This is different from the first embodiment only in the following points:

1) Constants used at steps #17, #30, #35, #41 and #43 are smaller because of the reduction of the photodiodes.

2) The order of storing values obtained by the A/D conversion in the memory is changed at step #15 and #28 because of the change of the A/D conversion order.

3) In the light source correction carried out at steps posterior to step #44, the value, of the light source, corresponding to each of wavelengths which are measured by the spectral sensor S1 for test piece measurement, and not measured by the spectral sensor S2 for light source measurement is calculated by the interpolation method using measured values for wavelengths on both sides of such a wavelength.

As obvious from the above description, according to the invention, setting of a set of arbitrary coefficients one for each wavelength by the coefficient setting means and calculation of the sum of products, for the respective wavelengths, of measured spectral values times the coefficients of the set by the calculating means allows operators to know the output given in the measurement of light source color or of non-luminous object color by light receiving means having arbitrary spectral sensitivities. So, a spectrophotometer according to this invention can be used in various measurements such as of color density of colored pictures, color density of print, etc., in addition to calculation of color value.

On the other hand, in a spectrophotometer according to the invention for measuring either a spectral reflectance or spectral transmissivity of a test piece irradiated by a light source for illumination, as spectral distributions of the light source used for color evaluation are also multiplied by the respective products of the coefficients times the corresponding measured spectral values, it can be known how colors of a non-luminous object appear under an illumination light source having arbitrary spectral distributions.

Moreover, according to the present invention, measured values for predetermined wavelengths or for wavelengths at predetermined intervals can be calculated using such spectrodetectors as vary in measurement wavelengths and measurement wavelength intervals, because a value corresponding to the peak wavelength of spectral sensitivity of each spectrodetector is stored in the first memory, a value measured by each light receiving element is stored in the second memory, and then, measured values for the pre-determined wavelengths are calculated by an interpolation method using the contents of the first and second memories.

Additionally, if the light receiving portion including optical band-pass filters as well as light receiving elements is separable from the calculating portion including the interpolating means, and if the first memory for storing values corresponding to peak wavelengths is provided on the side of the light receiving portion, in replacing the light receiving portion with another light receiving portion, the memory for storing the peak wavelengths is also replaced. Therefore, one to one correspondence between each light receiving element and each memory for storing the peak wavelengths is obtained and mistakes are not made.

Furthermore, the spectrophotometer according to the present invention comprises a memory to store information on the spectral sensitivities corresponding to values obtained by integrating spectral sensitivity of spectrodetectors, each of which consists of a light splitting means and a light receiving means in combination, relative to each section of the measurement wavelength region; and a mathematical operation means to calculate each light intensity by solving simultaneous equations holding for the relation between output of each of the light receiving means, spectral sensitivity information stored in the memory, and light intensity in each section of the measurement wavelength region, so that true light intensity of any wavelength excluding influences of other wavelengths can be obtained. Accordingly, correct measured values can be obtained in the spectrophotometry even if the spectral sensitivity properties are insufficient and/or there is much stray light.

Additionally, if the measurement wavelength region is sectionalized at a bisection point of the spectral sensitivity peaks of each adjacent spectrodetectors, one peak exists in one sectionalized wavelength region and therefore, diagonal components of the correction coefficient matrix can be enlarged and measurement accuracy improves.

It is convenient for measurement of trichromatic values, for example, to construct the spectrophotometer so that a plurality of sets of coefficients may be set in the coefficient setting means and that summing of the products may be carried out with respect to each set of coefficients, because a plurality of spectral sensitivities can be set.

Furthermore, it is convenient for color measurement of colored pictures and the like to construct the spectrophotometer so that the logarithmic vale of the sum calculated by the calculating means can be calculated, because such color density as of photographs is evaluated in logarithmic values.

Moreover, if the spectrophotometer is constructed so that set coefficients may be displayed on a graph, the values of the coefficients can be easily confirmed by seeing the graph, so that mistakes in setting coefficients can be prevented.

Furthermore, the spectrophotometer according to the present invention comprises, in addition to the first splitting means for splitting light coming from the test piece into a plurality of light components of different wavelengths and the first light receiving element array for receiving the respective light components obtained by the splitting with the first splitting means, the second splitting means for splitting light emitted from the light source into a plurality of light components of different wavelengths and the second light receiving element array for receiving the respective light components obtained by the splitting with the second splitting means, so that spectral energy distribution of the light source can be also measured at each measurement of the test piece. Furthermore, the spectrophotometer according to the present invention comprises the calculating means for calculating the ratio of A/D converted value of the output from the first light receiving element array to that from the second light receiving element array, so that errors caused by the variation of the spectral energy distribution of the light source can be removed from the measured spectral value of the test piece and moreover, correct spectrophotometry can be effected even when a light source having unstable spectral energy distribution properties is used as a light source for irradiating the test piece.

Additionally, if the spectrophotometer is constructed so that, in the wavelength region where the spectral energy distribution of the light source varies gently relative to wavelengths, the pitch of the wavelengths of light components to be measured by the spectrodetectors consisting of the second splitting means in combination with the second light receiving array may be made larger than that of the light components to be measured by the spectrodetectors consisting of the first splitting means in combination with the first light receiving array and that a value for a wavelength present in each interval of the measurement wavelengths may be obtained through the calculation by the interpolation method, the number of light receiving elements included in the second light receiving element array can be reduced, so that circuits such as the photometric circuit and A/D conversion circuit can be constructed on a small scale and time required for measurement can be shortened.

Although the present invention has been described in connection with preferred embodiments thereof, many variations and modifications will now become apparent to those skilled in the art. It is preferred, therefore, that the present invenion is limited not by the specific disclosure herein, but only by the appended claims.

TABLE 1

| E | D | C | B | A | Q0 | Q1 | Q2 | Q3 | Q4 | Q5 | Q6 | Q7 | Q8 | Q9 |
|---|---|---|---|---|----|----|----|----|----|----|----|----|----|----|
| L | L | L | L | L | H  | L  | L  | L  | L  | L  | L  | L  | L  | L  |
| L | L | L | L | H | L  | H  | L  | L  | L  | L  | L  | L  | L  | L  |
| L | L | L | H | L | L  | L  | H  | L  | L  | L  | L  | L  | L  | L  |
| L | L | L | H | H | L  | L  | L  | H  | L  | L  | L  | L  | L  | L  |
| L | L | H | L | L | L  | L  | L  | L  | H  | L  | L  | L  | L  | L  |
| L | L | H | L | H | L  | L  | L  | L  | L  | H  | L  | L  | L  | L  |
| L | L | H | H | L | L  | L  | L  | L  | L  | L  | H  | L  | L  | L  |
| L | L | H | H | H | L  | L  | L  | L  | L  | L  | L  | H  | L  | L  |
| L | H | L | L | L | L  | L  | L  | L  | L  | L  | L  | L  | H  | L  |
| L | H | L | L | H | L  | L  | L  | L  | L  | L  | L  | L  | L  | H  |
| H | X | X | X | X | L  | L  | L  | L  | L  | L  | L  | L  | L  | L  |

H: High level
L: Low level
X: H or L

What is claimed is:

1. A spectrophotometer for measuring the light intensity of each wavelength of light received from a test piece, said spectrophotometer comprising:
   a light source for irradiating the test piece;
   first splitting means for splitting light coming from the test piece into its different wavelengths;
   a first array of light-receiving elements for receiving the wavelengths of light from said first splitting means and generating spectral light intensity values for each wavelength of light received;

second splitting means for splitting light emitted from said light source into its different wavelength;

a second array of light-receiving elements for receiving the wavelengths of light from said second splitting means and for generating spectral light intensity values for each wavelength of light received, wherein the pitch of the wavelengths of light to be measured by the second light-receiving element array in combination with the second splitting means is larger than that of the light to be measured by the first light-receiving element array in combination with the first splitting means;

an analog-to-digital converter for converting the spectral light intensity values for each wavelength output from both the first and second light-receiving element arrays into digital form; and calculating means for calculating the ratios of the spectral light intensity values for each wavelength from the first light-receiving element array to the spectral light intensity values for each wavelength from the second light-receiving element array.

2. A spectrophotometer claimed in claim 1, further comprising interpolating means for calculating values of light intensity of the light source for each wavelength by the same pitch as the light from the test piece.

* * * * *